United States Patent
Page et al.

(10) Patent No.: US 9,006,238 B2
(45) Date of Patent: *Apr. 14, 2015

(54) PYRAZOLO PYRIDINE DERIVATIVES AS NADPH OXIDASE INHIBITORS

(71) Applicant: Genkyotex SA, Plan-les-Ouates (CH)

(72) Inventors: Patrick Page, Saint-Julien-en-Genevois (FR); Mike Orchard, Oxon (GB); Benoit Laleu, Collonges-sous-Salève (FR); Francesca Gaggini, Geneva (CH)

(73) Assignee: Genkyotex SA, Plan-les-Ouates (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/755,617

(22) Filed: Jan. 31, 2013

(65) Prior Publication Data

US 2013/0158027 A1 Jun. 20, 2013

Related U.S. Application Data

(63) Continuation of application No. 13/120,438, filed as application No. PCT/IB2009/054155 on Sep. 22, 2009, now Pat. No. 8,455,486.

(30) Foreign Application Priority Data

Sep. 23, 2008 (EP) .................................. 08164849

(51) Int. Cl.
| | |
|---|---|
| A61K 31/5377 | (2006.01) |
| A61K 31/496 | (2006.01) |
| A61K 31/497 | (2006.01) |
| A61K 31/437 | (2006.01) |
| C07D 413/14 | (2006.01) |
| C07D 401/14 | (2006.01) |
| C07D 471/04 | (2006.01) |
| A61K 31/444 | (2006.01) |
| A61K 31/4545 | (2006.01) |
| A61K 45/06 | (2006.01) |

(52) U.S. Cl.
CPC .......... *A61K 31/5377* (2013.01); *C07D 471/04* (2013.01); *A61K 31/437* (2013.01); *A61K 31/444* (2013.01); *A61K 31/4545* (2013.01); *A61K 31/496* (2013.01); *A61K 45/06* (2013.01)

(58) Field of Classification Search
CPC ............ A61K 31/5377; A61K 31/437; A61K 31/444; A61K 31/4545; A61K 31/496; C07D 471/04
USPC ......... 514/234.2, 252.1, 255.05, 303
See application file for complete search history.

(56) References Cited

U.S. PATENT DOCUMENTS

| | | | |
|---|---|---|---|
| 3,931,407 A | 1/1976 | Richard et al. | |
| 4,909,827 A | 3/1990 | Gehring et al. | |
| 5,869,516 A | 2/1999 | Arlt et al. | |
| 6,107,306 A | 8/2000 | Carpino et al. | |
| 6,624,309 B1 | 9/2003 | Lloyd et al. | |
| 8,288,432 B2 | 10/2012 | Page et al. | |
| 8,389,518 B2 * | 3/2013 | Page et al. ................ | 514/234.2 |
| 8,404,742 B2 | 3/2013 | Wierzbicki et al. | |
| 8,455,485 B2 * | 6/2013 | Page et al. ................ | 514/234.2 |
| 8,481,562 B2 | 7/2013 | Page et al. | |
| 8,748,456 B2 | 6/2014 | Page et al. | |
| 8,865,758 B2 | 10/2014 | Page et al. | |
| 2007/0014739 A1 | 1/2007 | Eldridge et al. | |
| 2007/0037883 A1 | 2/2007 | Dusting et al. | |
| 2007/0082910 A1 | 4/2007 | Yamamoto et al. | |
| 2008/0176934 A1 | 7/2008 | Verbeuren et al. | |
| 2009/0099179 A1 | 4/2009 | Klein et al. | |
| 2009/0163452 A1 | 6/2009 | Schwartz | |
| 2010/0048560 A1 | 2/2010 | Page et al. | |
| 2010/0120749 A1 | 5/2010 | Page et al. | |
| 2011/0172266 A1 | 7/2011 | Page et al. | |
| 2011/0178081 A1 | 7/2011 | Page et al. | |
| 2011/0269757 A1 | 11/2011 | Page et al. | |
| 2012/0172352 A1 | 7/2012 | Page et al. | |
| 2012/0316163 A1 | 12/2012 | Page et al. | |
| 2012/0316380 A1 | 12/2012 | Page et al. | |
| 2013/0123256 A1 | 5/2013 | Page et al. | |
| 2013/0143879 A1 | 6/2013 | Page et al. | |
| 2013/0296362 A1 | 11/2013 | Page et al. | |
| 2014/0323500 A1 | 10/2014 | Brandes et al. | |

FOREIGN PATENT DOCUMENTS

| | | |
|---|---|---|
| DE | 102005048897 | 10/2005 |
| EP | 0274642 A | 7/1988 |
| EP | 1175900 A2 | 1/2002 |
| EP | 1 291 017 | 3/2003 |
| EP | 1396493 | 3/2004 |
| EP | 1505068 A | 2/2005 |

(Continued)

OTHER PUBLICATIONS

Bedard, K. et al. "The NOX Family of ROS-Generating NADPH Oxidases: Physiology and Pathophysiology" *Physiological Reviews*, Jan. 2007, pp. 245-313, vol. 87.

Ferrara, N. et al. "Angiogenesis as a therapeutic target" *Nature*, Dec. 15, 2005, pp. 967-974, vol. 438.

Folkman, J. "Angiogenesis" *Annu. Rev. Med.*, 2006, pp. 1-18, vol. 57.

Griendling, K. K. et al. "NAD(P)H Oxidase: Role in Cardiovascular Biology and Disease" *Circulation Research*, 2000, pp. 494-501, vol. 86.

Ray, R. et al. "NADPH oxidase and endothelial cell function" *Clinical Science*, 2005, pp. 217-226, vol. 109.

Wu, D. et al. "NADPH oxidase mediates oxidative stress in the 1-methyl-4-phenyl-1,2,3,6-tetrahydropyridine model of Parkinson's disease" *PNAS*, May 13, 2003, pp. 6145-6150, vol. 100, No. 10.

(Continued)

*Primary Examiner* — Samantha Shterengarts

(74) *Attorney, Agent, or Firm* — Saliwanchik, Lloyd & Eisenschenk

(57) ABSTRACT

The present invention is related to pyrazolo pyridine derivatives of Formula (I), pharmaceutical composition thereof and to their use for the treatment and/or prophylaxis of disorders or conditions related to Nicotinamide adenine dinucleotide phosphate oxidase (NADPH Oxidase).

23 Claims, No Drawings

(56) References Cited

FOREIGN PATENT DOCUMENTS

| | | |
|---|---|---|
| EP | 2002835 A | 12/2008 |
| WO | WO 97/19679 | 6/1997 |
| WO | WO 02/088122 | 11/2002 |
| WO | WO 2004/005267 | 1/2004 |
| WO | WO 2005/080378 | 9/2005 |
| WO | WO 2006/041874 | 4/2006 |
| WO | WO 2006/094187 | 9/2006 |
| WO | WO 2008/113856 | 9/2008 |
| WO | WO 2008/116926 | 10/2008 |
| WO | WO 2009/072643 | 6/2009 |
| WO | WO 2010/035217 | 4/2010 |
| WO | WO 2010/035219 | 4/2010 |
| WO | WO 2010/035221 | 4/2010 |
| WO | WO 2011/036651 | 3/2011 |
| WO | WO 2011/085293 | 7/2011 |
| WO | WO 2011/101804 | 8/2011 |
| WO | WO 2012/068972 | 5/2013 |

OTHER PUBLICATIONS

Garrido-Urbani, S. et al. "Targeting Vascular NADPH Oxidase 1 Blocks Tumor Angiogenesis through a PPARα Mediated Mechanism" *PLoS ONE*, Feb. 2011, pp. 1-13, vol. 6, Issue 2.

Abdelrahman, M. et al. "Inhibitors of NADPH Oxidase Reduce the Organ Injury in Hemorrhagic Shock" *Shock*, 2005, pp. 107-114, vol. 23, No. 2.

Anantharam, V. et al. "Pharmacological inhibition of neuronal NADPH oxidase protects against 1-methyl-4-phenylpyridinium (MPP$^+$)-induced oxidative stress and apoptosis in mesencephalic dopaminergic neuronal cells" *NeuroToxicology*, 2007, pp. 988-997, vol. 28.

Baker, M. A. et al. "Reactive oxygen species in spermatozoa: methods for monitoring and significance for the origins of genetic disease and infertility" *Reproductive Biology and Endocrinology*, 2005, pp. 1-9, vol. 3, No. 67.

Chen, P. et al. "Role of NADPH oxidase and ANG II in diabetes-induced retinal leukostasis" *Am. J. Physiol. Reul. Integr. Comp. Physiol.*, 2007, pp. R1619-R1629, vol. 293.

Cucoranu, I. et al. "NAD(P)H Oxidase 4 Mediates Transforming Growth Factor-b1-Induced Differentiation of Cardiac Fibroblasts Into Myofibroblasts" *Circulation Research*, 2005, pp. 900-907, vol. 97.

El Benna, J. et al. "NADPH Oxidase Priming and p47phox Phosphorylation in Neutrophils from Synovial Fluid of Patients with Rheumatoid Arthritis and Spondylarthropathy" *Inflammation*, Dec. 2002, pp. 273-278, vol. 26, No. 6.

Ellis E. A. et al. "Time Course of NADH Oxidase, Inducible Nitric Oxide Synthase and Peroxynitrite in Diabetic Retinopathy in the BBZ/WOR Rat" *Nitric Oxide: Biology and Chemistry*, 2002, pp. 295-304, vol. 6, No. 3.

Fukuyama, M. et al. "Overexpression of a novel superoxide-producing enzyme, NADPH oxidase 1, in adenoma and well differentiated adenocarcinoma of the human colon" *Cancer Letters*, 2005, pp. 97-104, vol. 221.

Gavazzi, G. et al. "NOX1 Deficiency Protects from Aortic Dissection in Response to Angiotensin II" *Hypertension*, 2007, pp. 189-196, vol. 50.

Gukovskaya, A. S. et al. "Neutrophils and NADPH Oxidase Mediate Intrapancreatic Trypsin Activation in Murine Experimental Acute Pancreatitis" *Gastroenterology*, 2002, pp. 974-984, vol. 122.

Hausmann, M. et al. "Subtractive screening reveals up-regulation of NADPH oxidase expression in Crohn's disease intestinal macrophages" *Clin. Exp. Immunol.*, 2001, pp. 4855, vol. 125.

Hoidal, J. R. et al. "The Role of Endogenous NADPH Oxidases in Airway and Pulmonary Vascular Smooth Muscle Function" *Antioxidants & Redox Signaling*, 2003, pp. 751-758, vol. 5.

Inoguchi, T. et al. "NAD(P)H Oxidase Activation: A Potential Target Mechanism for Diabetic Vascular Complications, Progressive β-Cell Dysfunction and Metabolic Syndrome" *Current Drug Targets*, 2005, pp. 495-501, vol. 6.

Jin, L. et al. "NADPH oxidase: recent evidence for its role in erectile dysfunction" *Asian J. Androl.*, Jan. 2008, pp. 6-13, vol. 10.

Kawai, Y. et al. "Relationship of Intracellular Calcium and Oxygen Radicals to Cisplatin-Related Renal Cell Injury" *J. Pharmacol. Sci.*, 2006, pp. 65-72, vol. 100.

Klees, R. F. et al. "Apocynin Derivatives Interrupt Intracellular Signaling Resulting in Decreased Migration in Breast Cancer Cells" *Journal of Biomedicine and Biotechnology*, 2006, pp. 1-10, vol. 2006.

Krijnen, P. A. et al. "Increased Nox2 expression in human cardiomyocytes after acute myocardial infarction" *J. Clin. Pathol.*, 2003, pp. 194-199, vol. 56.

Lanone S. et al. "Bilirubin decreases NOS2 expression via inhibition of NAD(P)H oxidase: implications for protection against endotoxic shock in rats" *The FASEB Journal*, 2005, pp. 1-26.

Lee, N. K. et al. "A crucial role for reactive oxygen species in RANKL-induced osteoclast differentiation" *Blood*, 2005, pp. 852-859, vol. 106.

Liu, Y. et al. "Suppression of Microglial Inflammatory Activity by Myelin Phagocytosis: Role of p47-PHOX-Mediated Generation of Reactive Oxygen Species" *The Journal of Neuroscience*, Dec. 13, 2006, pp. 12904-12913, vol. 26, No. 50.

Nibali, L. et al. "NADPH oxidase (CYBA) and FcγR polymorphisms as risk factors for aggressive periodontitis" *J. Clin. Periodontol*, 2006, pp. 529-539, vol. 33.

Patel, C. et al. "Prolonged Reactive Oxygen Species Generation and Nuclear Factor-κB Activation after a High-Fat, High-Carbohydrate Meal in the Obese" *The Journal of Clinical Endocrinology & Metabolism*, 2007, pp. 4476-4479, vol. 92, No. 111.

Patel, M. et al. "Activation of NAPDH oxidase and extracellular superoxide production in seizure-induced hippocampal damage" *Journal of Neurochemistry*, 2005, pp. 123-131, vol. 92.

Puntambekar, P. et al. "Essential Role of Rac1/NADPH oxidase in nerve growth factor induction of TRPV1 expression" *Journal of Neurochemistry*, 2005, pp. 1689-1703, vol. 95.

Qian, L. et al. "Sinomenine, a natural dextrorotatory morphinan analog, is anti-inflammatory and neuroprotective through inhibition of microglial NADPH oxidase" *Journal of Neuroinflammation*, 2007, pp. 1-14, vol. 4, No. 23.

Ritsick, D. R. et al. "Spring brings breezes, wheezes, and pollen oxidases" *The Journal of Clinical Investigation*, Aug. 2005, vol. 115, No. 8.

Sato, K. et al. "In vivo lipid-derived free radical formation by NADPH oxidase in acute lung injury induced by lipopolysaccharide: a model for ARDS" *FASEB J.*, 2002, pp. 1713-1720, vol. 16.

Satoh, M. et al. "NAD(P)H oxidase and uncoupled nitric oxide synthase are major sources of glomerular superoxide in rats with experimental diabetic nephropathy" *Am. J. Physiol Renal Physiol*, 2005, pp. F1144-F1152, vol. 288.

Sharma, K. et al. "TGF-β impairs renal autoregulation via generation of ROS" *Am. J. Physiol Renal Physiol*, 2005, pp. F1069-F1079, vol. 288.

Sirker, A. et al. "Involvement of NADPH Oxidases in Cardiac Remodelling and Heart Failure" *Am. J. Nephrol*, 2007, pp. 649-660, vol. 27.

Sonta, T. et al. "Evidence for Contribution of Vascular NAD(P)H Oxidase to Increased Oxidative Stress in Animal Models of Diabetes and Obesity" *Free Radical Biology & Medicine*, 2004, pp. 115-123, vol. 37, No. 1.

Vaquero, V. C. et al. "Reactive Oxygen Species Produced by NAD(P)H Oxidase Inhibit Apoptosis in Pancreatic Cancer Cells" *The Journal of Biological Chemistry*, Aug. 13, 2004, pp. 34643-34654, vol. 279, No. 33.

Kerbel, R. S. "Tumor Angiogenesis" *N. Engl J Med*, May 8, 2008, pp. 2039-2049, vol. 358.

Hougee, S. et al. "Oral administration of the NADPH-oxidase inhibitor apocynin partially restores diminished cartilage proteoglycan synthesis and reduces inflammation in mice" *European Journal of Pharmacology*, 2006, pp. 264-269, vol. 531.

Chang, G. et al. "Specific Inhibition of NADP(H) Oxidase (NOX) Abrogates the Tumorigenic Phenotype of Renal Cancer Cells" Poster at Annual Meeting of the Society of Basic Urology, Nov. 2009, New Orleans, USA, p. 1.

(56) References Cited

OTHER PUBLICATIONS

Jain, V. K. et al. "NADPH Oxidase and Myeloperoxidase Activity in Psoriasis Leukocytes" *The Journal of Dermatology*, 1985, pp. 425-428, vol. 12.
Lambeth, J. D. et al. "NOX enzymes as novel targets for drug development" *Semin Immunopathol*, 2008, pp. 339-363, vol. 30.
Sturrock, A. et al. "Nox4 mediates TGF-β1-induced retinoblastoma protein phosphorylation, proliferaton, and hypertrophy in human airway smooth muscle cells" *Am. J Physiol. Lung. Cell Mol. Physiol.*, 2007, pp. L1543-1555. vol. 292, No. 6.
Ushio-Fukai, M. et al. "Reactive oxygen species and angiogenesis: NADPH oxidase as target for cancer therapy" *Cancer Letters*, 2008, pp. 37-52, vol. 266.
Banfi, B. et al. "NOX3, a Superoxide-generating NADPH Oxidase of the Inner Ear" *The Journal of Biological Chemistry*, Oct. 29, 2004, pp. 46065-46072, vol. 279, No. 44.
Wu, D.-C. et al. "The inflammatory NADPh oxidase enzyme modulates motor neuron degeneration in amyotrophic lateral sclerosis mice" *PNAS*, Aug. 8, 2006, pp. 12132-12137, vol. 103, No. 32.
Rao, P. V. et al. "Expression of nonphagocytic NADPH oxidase system in the ocular lens" *Molecular Vision*, 2004, pp. 112-121, vol. 10.
Nunomura, A. et al. "Oxidative Damage is the Earliest Event in Alzheimer Disease" *Journal of Neuropathology and Experimental Neurology*, Aug. 2001, pp. 759-767, vol. 60, No. 8.
Chemcats Accession No. 2029347921, Jun. 13, 2008, XP-002514328, p. 1.
Written Opinion in International Application No. PCT/IB2009/054148, Oct. 12, 2009, pp. 1-8.
Dornow, A. et al. "Darstellung and Umsetzung einiger substituierter 3-Nitro-pyridine" *Chem. Ber.*, 1966, pp. 244-253, vol. 99.
Junker, L. M. et al. "High-Throughput Screens for Small-Molecule Inhibitors of *Pseudomonas aeruginosa* Biofilm Development" *Antimicrobial Agents and Chemotherapy*, Oct. 2007, pp. 3582-3590, vol. 51, No. 10.
Written Opinion in International Application No. PCT/IB2009/054150, Oct. 13, 2010, pp. 1-11.
Chemcats Accession No. 2049339652, Jun. 13, 2008, XP-002514424, pp. 1-6.
Database CA [Online] Chemical Abstracts Service, Accession No. 2007:341007, 2007, XP-002558729, p. 1.
Database CA [Online] Chemical Abstracts Service, Accession No. 2004:14711, 2003, XP-002558730, pp. 1-2.
Written Opinion in International Application No. PCT/IB2009/054156, Mar. 3, 2010, pp. 1-10.
Office Action dated Apr. 17, 2012 in U.S. Appl. No. 13/120,436.
Hua, C. et al. "The vascular NAD(P)H oxidases as therapeutic targets in cardiovascular diseases" *TRENDS in Pharmacological Sciences*, Sep. 2003, pp. 471-478, vol. 24, No. 9.
Klein, C. et al. CAS:147:427219, 2007, Accession No. 2007:1146277, pp. 1-4.
Slade, R. et al. CAS:144:412361, 2006, Accession No. 2006:361235, pp. 1-4.
Cancer [online], retrieved on Jul. 6, 2007, retrieved from the internet, URL: http://www.nim.nih.gov/medlineplus/cancer.html, pp. 1-10.
Lala, P. K. et al. "Role of nitric oxide in tumor progression: Lessons from experimental tumors" *Cancer and Metastasis Reviews*, 1998, pp. 91-106, vol. 17.
Golub, T. R. et al. "Molecular Classification of Cancer: Class Discovery and Class Prediction by Gene Expression Monitoring" *Science*, Oct. 15, 1999, pp. 531-537, vol. 286.
Wolff, M. E. et al. "Burger's Medicinal Chemistry and Drug Discovery", 1994 Wiley-Interscience, Fifth Edition, vol. I: Principles and Practice, pp. 975-977.
"Derivative." Merriam-Webster Online Dictionary, 2010, accessed Apr. 20, 2010, http://merriam-webster.com/dictionary/derivative.
Office Action dated Mar. 19, 2012 in U.S. Appl. No. 12/532,567.
Office Action dated Oct. 13, 2010 in U.S. Appl. No. 12/532,336.
Office Action dated Mar. 29, 2011 in U.S. Appl. No. 12/532,336.
Office Action dated Jun. 18, 2012 in U.S. Appl. No. 12/532,336.
Cai, H. et al. "The vascular NAD(P)H oxidases as therapeutic targets in cardiovascular diseases" *TRENDS in Pharmacological Sciences*, Sep. 2003, pp. 471-478, vol. 24, No. 9.
Thabut, G. et al. "Tumor Necrosis Factor-α Increases Airway Smooth Muscle Oxidants Production through a NADPH Oxidase-like System to Enhance Myosin Light Chain Phosphorylation and Contractility" *The Journal of Biological Chemistry*, Jun. 21, 2002, pp. 22814-22821, vol. 277, No. 25.
Djordjevic, T. et al. "Human Urotensin II is a Novel Activator of NADPH Oxidase in Human Pulmonary Artery Smooth Muscle Cells" *Arteriosclerosis, Thrombosis, and Vascular Biology*, Mar. 2005, pp. 519-525, vol. 25.
Yang, S. et al. "Characterization of Interferon Gamma Receptors on Osteoclasts: Effect of Interferon Gamma on Osteoclastic Superoxide Generation" *Journal of Cellular Biochemistry*, 2002, pp. 645-654, vol. 84.
Ellis, E. A. et al. "Increased $H_2O_2$, Vascular Endothelial Growth Factor and Receptors in the Retina of the BBZ/WOR Diabetic Rat" *Free Radical Biology & Medicine*, 2000, pp. 91-191, vol. 28, No. 1.
Saxena, U. et al. "New approaches for treatment of diabetic nephropathy: the endothelium as a target for drug discovery" *Expert Opinion Ther. Targets*, 2001, pp. 539-545, vol. 5, No. 5.
Shi, Y. et al. "Increased NAD(P)H Oxidase and Reactive Oxygen Species in Coronary Arteries After Balloon Injury"*Arteriosclerosis, Thrombosis, and Vascular Biology*, May 2001, pp. 739-745, vol. 21.
Laleu, B. et al. "First in Class, Potent, and Orally Bioavailable NADPH Oxidase Isoform 4 (Nox4) Inhibitors for the Treatment of Idiopathic Pulmonary Fibrosis" *Journal of Medical Chemistry*, 2010, pp. 7715-7730, vol. 53.
Sedeek. M. et al. "Critical role of Nox4-based NADPH oxidase in glucose-induced oxidative stress in the kidney: implications in type 2 diabetic nephropathy" *American Journal of Physiology Renal Physiology*, Jul. 14, 2010, pp. F1348-F1358, vol. 299.
Vendrov, A. E. et al. "NADPH Oxidases Regulate CD44 and Hyaluronic Acid Expression in Thrombin-treated Vascular Smooth Muscle Cells and in Atherosclerosis" *The Journal of Biological Chemistry*, Aug. 20, 2010, pp. 26545-26557, vol. 285, No. 34.
Written Opinion in International Application No. PCT/IB2009/054155, Nov. 6, 2010, pp. 1-7.
Asaba, K. et al. "Effects of NADPH oxidase inhibitor in diabetic nephropathy" *Kidney International*, 2005, pp. 1890-1898, vol. 67.
Baumer, A. T. et al. "The NAD(P)H Oxidase Inhibitor Apocynin Improves Endothelial NO/Superoxide Balance and Lowers Effectively Blood Pressure in Spontaneously Hypertensive Rats: Comparison to Calcium Channel Blockade" *Clinical and Experimental Hypertension*, 2007, pp. 287-299, vol. 29.
Chirino, Y. I. et al. "Protective effects of apocynin against cisplatin-induced oxidative stress and nephrotoxicity" *Tosicology*, 2008, pp. 18-23, vol. 245.
Chan, E. C. et al. "Regulationof cell proliferation by NADPH oxidase-mediated signaling: Potential roles in tissue repair, regenerative medicine and tissue engineering" *Pharmacology & Therapeutics*, 2009, pp. 97-108, vol. 122.
Jarman, E. R. et al. "An inhibitor of NADPH oxidase-4 attenuates established pulmonary fibrosis in a rodent disease model" *AJRCMB Articles in Press*, Aug. 26, 2013, pp. 1-30.
Lafeber, F. P. J. G. et al. "Apocynin, a plant-derived, cartilage-saving drug, might be useful in the treatment of rheumatoid arthritis" *Rheumatology*, 1999, pp. 1088-1093, vol. 38.
Peters, E. A. et al. "Effect of Apocynin on Ozone-Induced Airway Hyperresponsiveness to Methacholine in Asthmatics" *Free Radical Biology & Medicine*, 2001, pp. 1442-1447, vol. 31, No. 11.
Rachmilewitz, D. et al. "Sulphydryl blocker induced small intestinal inflammation in rats: a new model mimicking Crohn's disease" *Gut*, 1997, pp. 358-365, vol. 41.
Tang, X. N. et al. "Apocynin Improves Outcome in Experimental Stroke with a Narrow Dose Range" *Neuroscience*, 2008, pp. 556-562, vol. 154.
Wang, W. et al. "Effect of the NADPH Oxidase Inhibitor Apocynin on Septic Lung Injury in Guinea Pigs" *American Journal of Respiratory and Critical Care Medicine*, 1994, pp. 1449-1452, vol. 150.
Zhao, W. et al. "Kidney Fibrosis in Hypertensive Rats: Role of Oxidative Stress" *Am J Nephrol*, 2008, pp. 548-554, vol. 28.

(56) References Cited

OTHER PUBLICATIONS

Written Opinion in International Application No. PCT/EP2008/053390, Jul. 21, 2008, pp. 1-6.
Written Opinion in International Application No. PCT/EP2008/053704, Jul. 7, 2008, pp. 1-7.
Office Action dated Dec. 22, 2014 in U.S. Appl. No. 14/357,605.
STN on the Web, File Registry, RN=727370-48-1 (Aug. 16, 2004), 890865-63-1 (Jul. 6, 2006), p. 1.
Englert, S. M. et al. "Pyrazolones Derived from the Carbethoxypiperidones" *Journal of American Chemical Society*, Mar. 1934, pp. 700-702, vol. 56.
Carpino, P. et al. "Pyrazolinone-piperidine Dipeptide Growth Hormone Secretagogues (GHSs): Discovery of Capromorelin" *Bioorganic & Medicinal Chemistry*, Feb. 20, 2003, pp. 581-590, vol. 11, No. 4.
Carpino, P. et al. "Discovery and Biological Characterization of Capromorelin Analogues with Extended Half-Lives" *Bioorganic & Medicinal Chemistry Letters*, Nov. 18, 2002, pp. 3279-3282, vol. 12, No. 22.
Guillou, S. et al. "N-arylation of 3-alkoxypyrazoles, the case of the pyridines" *Tetrahedron*, Feb. 10, 010, pp. 2654-2663, vol. 66, No. 14.
Pillarsetti, S. et al. "Role of oxidative stress and inflammation in the origin of Type 2 diabetes—a paradigm shift" Expert Opinion on Therapeutic Targets, 2004, pp. 401-408, vol. 8, No. 5.
Brigham, K. "Role of Free Radicals in Lung Injury" *Chest*, Jun. 1986, pp. 859-863, vol. 89, No. 6.
Liu, J. et al. "Extracellular superoxide enhances 5-HT-induced murine pulmonary artery vasoconstriction" *American Journal of Physiology—Lung Cellular and Molecular Physiology*, 2004, pp. L111-L118, vol. 287.
Girouard, H. et al. "Neurovascular coupling in the normal brain and in hypertension, stroke, and Alzheimer disease" *Journal of Applied Physiology*, 2006, pp. 328-335, vol. 100.
Leto, T. L. et al. "Role of Nox Family NADPH Oxidases in Host Defense" *Antioxidants & Redox Signaling*, 2006, pp. 1549-1561, vol. 8, Nos. 9-10.
Cheng, G. et al. "Homologs of gp91phox: cloning and tissue expression of Nox3, Nox4, and Nox5" *Gene*, 2001, pp. 131-140, vol. 269.
Written Opinion in International Application No. PCT/IB2011/050668, Jul. 11, 2011, pp. 1-9.
Krehan, D. et al. "Aza-THIP and Related Analogues of THIP as GABA$_c$ Antagonists" *Bioorganic & Medicinal Chemistry*, Jan. 1, 2003, pp. 4891-4896, vol. 11.
Database CA [Online], Chemical Abstract Accession No. 1977:155590, Ozdowska, Z. "New derivatives of N-benzyl-4-carbethoxy-3-piperidone" *Roczniki Chemii*, 1976, pp. 1-2, vol. 50, No. 10, XP-002598501.
Briones, A. M. et al. "Differential regulation of Nox1, Nox2 and Nox4 in vascular smooth muscle cells from WKY and SHR" *Journal of the American Society of Hypertension*, 2011, pp. 137-153, vol. 5, No. 3.
Musset, B. et al. "NOX5 in Human Spermatozoa" *The Journal of Biological Chemistry*, Mar. 16, 2012, pp. 9376-9388, vol. 287, No. 12.
Sedeek, M. et al. "Renoprotective effects of a novel Nox1/4 inhibitor in a mouse model of Type 2 diabetes" *Clinical Science*, 2013, pp. 191-202, vol. 124.
ACS on STN Tokyo, Registry, RN=955327-56-7 (Nov. 21, 2007), 955327-53-4 (Nov. 21, 2007), 955327-50-1 (Nov. 21, 2007), 955327-47-6 (Nov. 21, 2007), 955285-61-7 (Nov. 21, 2007), 955285-55-9 (Nov. 21, 2007), 955285-49-1 (Nov. 21, 2007), 955265-43-5 (Nov. 21, 2007), 955272-06-7 (Nov. 21, 2007), 955285-37-7 (Nov. 21, 2007) pp. 1-6.
STN on the Web, File Registry, RN=914071-42-4 (Nov. 28, 2006), 909372-43-6 (Oct. 3, 2006), 908551-37-1 (Sep. 26, 2006), 906780-88-9 (Sep. 15, 2006), 906212-76-8 (Sep. 10, 2006), 906212-74-6 (Sep. 10, 2006), 906212-70-2 (Sep. 10, 2006), 906212-05-3 (Sep. 10, 2006), 899030-77-4 (Aug. 6, 2006), 899030-70-7 (Aug. 6, 2006), 899030-63-8 (Aug. 6, 2006), 899030-57-0 (Aug. 6, 2006), 899026-88-1 (Aug. 6, 2006), 899026-83-6 (Aug. 6, 2006), 899026-78-9 (Aug. 6, 2006), 899026-67-6 (Aug. 6, 2006), 899026-57-4 (Aug. 6, 2006), 899026-52-9 (Aug. 6, 2006), 899026-47-2 (Aug. 6, 2006), 899026-42-7 (Aug. 6, 2006), 899026-37-0 (Aug. 6, 2006), 899026-32-5 (Aug. 6, 2006), 899026-19-8 (Aug. 6, 2006), 897547-95-4 (Jul. 31, 2006), 897547-93-2 (Jul. 31, 2006), 897547-92-1 (Jul. 31, 2006), 897547-91-0 (Jul. 31, 2006), 897547,90-9 (Jul. 31, 2006), 896654-25-4 (Jul. 28, 2006), 896654-23-2 (Jul. 28, 2006), 896654-21-0 (Jul. 28, 2006), 896654-19-6 (Jul. 28, 2006), 896056-52-3 (Jul. 25, 2006), 896056-49-8 (Jul. 25, 2006), 896056-46-5 (Jul. 25, 2006), 895991-49-8 (Jul. 25, 2006), 895991-44-3 (Jul. 25, 2006, 895991-40-9 (Jul. 25, 2006), pp. 1-18.
STN on the Web, File Registry, RN=895991-35-2 (Jul. 25, 2006),895991-30-7 (Jul. 25, 2006),895991-25-0 (Jul. 25, 2006),895991-20-5 (Jul. 25, 2006),895991-15-8 (Jul. 25, 2006),895991-02-3 (Jul. 25, 2006),895990-97-3 (Jul. 25, 2006),895990-92-8 (Jul. 25, 2006),895990-73-5 (Jul. 25, 2006),895990-68-8 (Jul. 25, 2006),895990-54-2 (Jul. 25, 2006),895990-49-5 (Jul. 25, 2006),895990-40-6 (Jul. 25, 2006),890865-63-1 (Jul. 6, 2006), 885906-56-9 (May 29, 2006),885906-51-4 (May 29, 2006),885906-35-4 (May 29, 2006), 885906-31-0 (May 29, 2006),885906-27-4 (May 29, 2006),885906-21-8 (May 29, 2006),885890-49-3 (May 29, 2006),885888-49-3 (May 29, 2006),847586-98-5 (Mar. 30, 2005),847586-96-3 (Mar. 30, 2005),847586-86-1 (Mar. 30, 2005),847586-83-8 (Mar. 30, 2005),847586-82-7 (Mar. 30, 2005),847586-81-6 (Mar. 30, 2005),847586-74-7 (Mar. 30, 2005),847586-72-5 (Mar. 30, 2005),847586-69-0 (Mar. 30, 2005),847586-56-5 (Mar. 30, 2005),847586-51-0 (Mar. 30, 2005),847586-49-6 (Mar. 30, 2005),847586-42-9 (Mar. 30, 2005),847586-38-3 (Mar. 30, 2005),847586-37-2 (Mar. 30, 2005),847586-36-1 (Mar. 30, 2005), pp. 1-20.
STN on the Web, File Registry, RN=847586-32-7 (Mar. 30, 2005),847586-30-5 (Mar. 30, 2005),847586-24-7 (Mar. 30, 2005),847586-23-6 (Mar. 30, 2005),847573-56-2 (Mar. 30, 2005),847573-45-9 (Mar. 30, 2005),847573-43-7 (Mar. 30, 2005),847573-41-5 (Mar. 30, 2005),847573-40-4 (Mar. 30, 2005),847573-35-7 (Mar. 30, 2005),847573-31-3 (Mar. 30, 2005),847573-25-5 (Mar. 30, 2005),847573-23-3 (Mar. 30, 2005),847573-13-1 (Mar. 30, 2005),847573-07-3 (Mar. 30, 2005),847572-88-7 (Mar. 30, 2005),847572-77-4 (Mar. 30, 2005),847572-75-2 (Mar. 30, 2005),847572-66-1 (Mar. 30, 2005),847572-61-6 (Mar. 30, 2005),847572-60-5 (Mar. 30, 2005),847572-57-0 (Mar. 30, 2005),847572-51-4 (Mar. 30, 2005),847572-38-7 (Mar. 30, 2005),847572-35-4 (Mar. 30, 2005),847572-33-2 (Mar. 30, 2005),727370-48-1 (Aug. 16, 2004),669753-72-4 (Apr. 1, 2004),669753-67-7 (Apr. 1, 2004),669753-62-2 (Apr. 1, 204),516455-29-1 (May 16, 2003), pp. 1-16.
Block, K. et al. "Subcellular localization of Nox4 and regulation in diabetes" *PNAS*, Aug. 25, 2009, pp. 14385-14390, vol. 106, No. 34.
De Minicis, S. et al. "Oxidative stress in alcoholic liver disease: Role of NADPH oxidase complex" *Journal of Gastroenterology and Hepatology*, 2008, pp. S98-S103, Supp 1, No. 23.
Forbes, J. M. et al. "Diabetic Nephropathy: Where Hemodynamics Meets Metabolism" *Exp Clin Endocrinol Diabetes*, 2007, pp. 1-16.
Gorin, Y. et al. "Nox4 NAD(P)H Oxidase Mediates Hypertrophy and Fibronectin Expression in the Diabetic Kidney" *The Journal of Biological Chemistry*, Nov. 25, 2005, pp. 39616-39626, vol. 280, No. 47.
Guichard, C. et al. "NOX family NADPH oxidases in liver and in pancreatic islets: a role in the metabolic syndrome and diabetes?" *Biochemical Society Transactions*, 2008, pp. 920-929, vol. 36.
Jiang, J. et al. "Apoptotic body engulfment by hepatic stellate cells promotes their survival by the JAK/STAT and Akt/NF-κB-dependent pathways" *J Hepatol.*, Jul. 2009, pp. 139-148, vol. 51. No. 1.
Kakehi, T. et al. "NOX enzymes and diabetic complications" *Semin Immunopathol*, 2008, pp. 301-314, vol. 30.
Lambeth, D. "Nox Enzymes, ROS, and Chronic Disease: An Example of Antagonistic Pleiotropy" *Free Radic Biol Med.*, Aug. 2007, pp. 332-347, vol. 43, No. 3.
Nam, S. M. et al. "Effects of NADPH oxidase inhibitor on diabetic nephropathy in OLEFT rats: The role of reducing oxidative stress in its protective property" *Diabetes Research and Clinical Practice*, 2009, pp. 176-182, vol. 83.

(56) References Cited

OTHER PUBLICATIONS

Tojo, A. et al. "Suppressing renal NADPH oxidase to treat diabetic nephropathy" *Expert Opin. Ther. Targets*, 2007, pp. 1011-1018, vol. 11, No. 8.
Allowed claims of U.S. Appl. No. 13/734,205, 2014.
Currently pending claims of U.S. Appl. No. 13/755,387, 2013.
Currently pending claims of U.S. Appl. No. 13/120,440, 2014.
Currently pending claims of U.S. Appl. No. 13/394,904, 2014.
Vernet, P. et al. "Analysis of Reactive Oxygen Species Generating Systems in Rat Epididymal Spermatozoa" *Biology of Reproduction*, 2001, pp. 1102-1113, vol. 65.
Written Opinion in International Application No. PCT/IB2011/050667, Jun. 22, 2011, pp. 1-8.
Gaggini, F. et al. "Design, synthesis and biological activity of original pyrazolo-pyrido-diazepine, -pyrazine and -oxazine dione derivatives as novel dual Nox4/Nox1 inhibitors" *Bioorganic & Medicinal Chemistry*, 2011, pp. 6989-6999, vol. 19.
Written Opinion in International Application No. PCT/IB2010/054329, Mar. 1, 2011, pp. 18.
Fujita, M. et al. "Pyrroloquinolones and pyrazoloquinolones as potential antibacterial agents. Synthesis and antibacterial activity" *European Journal of Medicinal Chemistry*, 1996, pp. 981-988, vol. 31.
Allowed claims of U.S. Appl. No. 13/935,667, 2014.
Borbely, G. et al. "Small-Molecule Inhibitors of NADPH Oxidase 4" *J. Med. Chem.*, 2010, pp. 6758-6762, vol. 53.
Kim, J.-E. et al. "NADPH Oxidase inhibitors: a patent review" *Expert Opinion of Therapeutic Patents*, Aug. 2011, pp. 1147-1158, vol. 21, No. 8.
Huang, W. et al. "Simvastatin protects osteoblast against $H_2O_2$-induced oxidative damage via inhibiting the upregulation of Nox4" *Mol Cell Biochem*, 2012, pp. 71-77, vol. 360.
Bao, X. et al. "Atorvastatin inhibits homocysteine-induced oxidative stress and apoptosis in endothelial progenitor cells involving Nox4 and p38MAPK" *Atherosclerosis*, 2010, pp. 114-121, vol. 210.
Yang, S. et al. "Nox4 Participates in Superoxide Production During Osteoclast Differentiation and Bone Resorption" *Journal of Bone and Mineral Research*, Oct. 1, 2004, p. SA314, vol. 19, abstract only.
Yang, S. et al. "A New Superoxide-generating Oxidase in Murine Osteoclasts" *The Journal of Biological Chemistry*, Feb. 23, 2001, pp. 5452-5458, vol. 276, No. 8.
Yang, S. et al. "Expression of Nox4 in Osteoclasts" *Journal of Cellular Biochemistry*, 2004, pp. 238-248, vol. 92.
Chen, J.-R. et al. "Inhibition of NADPH Oxidases Prevents Chronic Ethanol-Induced Bone Loss in Female Rats" *The Journal of Pharmacology and Experimental Therapeutics*, Mar. 2011, pp. 734-742, vol. 336, No. 3.
Sturrock, A. et al. "Transforming growth factor-β1 induces Nox4 NAD(P)H oxidase and reactive oxygen species-dependent proliferation in human pulmonary artery smooth muscle cells" *Am J Physiol Lung Cell Mol Physiol*, 2006, pp. L661-L673, vol. 290.
Maruotti, N. et al. "Osteoclastogenesis and arthritis" *Clin Exp Med*, 2011, pp. 137-145, vol. 11.
Silvestris, F. et al. "Cell Fusion and Hyperactive Osteoclastogenesis in Multiple Myeloma" *Adv Exp Med Biol.*, 2011, pp. 113-128, vol. 714.
Wang, Z. et al. "Osteoclasts and odontoclasts: signaling pathways to development and disease" *Oral Diseases*, 2011, pp. 129-142, vol. 17.

Takac, I. et al. "The E-loop is Involved in Hydrogen Peroxide Formation by the NADPH Oxidase Nox4" *J. Biol. Chem.*, Apr. 15, 2011, pp. 13304-13313, vol. 286, No. 15.
Helmcke, I. et al. "Identification of Structural Elements in Nox1 and Nox4 Controlling Localization and Activity" *Antioxidants & Redox Signaling*, 2009, pp. 1279-1287, vol. 11, No. 6.
Sasaki, H. et al. "Receptor activator of nuclear factor-κB ligand-induced mouse osteoclast differentiation is associated with switching between NADPH oxidase homologues" *Free Radical Biology & Medicine*, 2009, pp. 189-199, vol. 47.
Sasaki, H. et al. "NADPH oxidase-derived reactive oxygen species are essential for differentiation of a mouse macrophage cell line (RAW264.7) into osteoclasts" *J. Med. Invest.*, Feb. 2009, pp. 33-41, vol. 56.
Goettsch, C. et al. "NADPH oxidase 4 limits bone mass by promoting osteoclastogenesis" *The Journal of Clinical Investigation*, Nov. 2013, pp. 4731-4738, vol. 123, No. 11.
Written Opinion in International Application No. PCT/IB2012/056286, Jan. 22, 2013, pp. 1-10.
Hecker, L. et al. "Reversal of Persistent Fibrosis in Aging by Targeting Nox4-Nrf2 Redox Imbalance" *Sci Transl Med*, Apr. 9, 2014, pp. 1-12, vol. 6, No. 231.
Di Marco, E. et al. "Pharmacological inhibition of NOX reduces atherosclerotic lesions, vascular ROS and immune—inflammatory responses in diabetic $Apoe^{-/-}$ mice" *Diabetologia*, 2014, pp. 633-642, vol. 57.
Jha, J. et al. "Genetic Targeting or Pharmacologic Inhibition of NADPH Oxidase Nox4 Provides Renoprotection in Long-Term Diabetic Nephropathy" *J Am Soc Nephrol*, 2014, pp. 1-18, vol. 25.
STN on the Web, File Registry, RN= 1040710-09-5, 1040708-33-5, 1040708-03-9, 1040703-20-5, 1040701-29-8. 1040699-70-4, 1040693-37-5, 1040691-81-3 (the above, registered on Aug. 13, 2008); 1029773-59-8 (registered on Jun. 22, 2008); 1013978-57-8 (registered on Apr. 13, 2008); 1010935-30-4, 1010935-27-9, 1010915-05-5, 1010896-75-9, 1010892-94-0, 1010886-89-1, 1010882-92-4, 1010878-48-4, 1010876-16-0 (the above, registered on Mar. 30, 2008); 1006654-90-5, 1006498-67-4 (the above, registered on Mar. 4, 2008); 956282-84-1 (registered on Nov. 29, 2007); 890865-63-1 (registered on Jul. 6, 2006); 727370-48-1 (registered on Aug. 16, 2004); 669753-62-2 (registered on Apr. 1, 2004). pp. 1-3.
Aoyama, T. et al. "Nicotinamide Adenine Dinucleotide Phosphate Oxidase in Experimental Liver Fibrosis: GKT137831 as a Novel Potential Therapeutic Agent" *Hepatology*, 2012, pp. 2316-2327, vol. 56, No. 6.
Jiang, J. X. et al. "Liver fibrosis and hepatocyte apoptosis are attenuated by GKT137831, a novel NOX4/NOX1 inhibitor in vivo" *Free Radical Biology and Medicine*, 2012, pp. 289-296, vol. 53.
Green, D. E. et al. "The Nox4 Inhibitor GKT137831 Attenuates Hypoxia-Induced Pulmonary Vascular Cell Proliferation" *American Journal of Respiratory Cell and Molecular Biology*, Nov. 2012, pp. 718-726, vol. 47, Issue 5.
Gray, S. P. et al. "*NADPH* Oxidase 1 Plays a Key Role in Diabetes Mellitus—Accelerated Atherosclerosis" *Circulation*, May 7, 2013, pp. 1888-1902.
Wilkinson-Berka, J. et al. "NADPH Oxidase, NOX1, Mediates Vascular Injury in Ischemic Retinopathy" *Antioxidants & Redox Signaling*, 2013, pp. 1-15.
Office Action dated Sep. 17, 2014 in U.S. Appl. No. 13/120,440.

\* cited by examiner

PYRAZOLO PYRIDINE DERIVATIVES AS NADPH OXIDASE INHIBITORS

CROSS-REFERENCE TO RELATED APPLICATIONS

This application is a continuation of U.S. Ser. No. 13/120,438, filed Mar. 23, 2011 which is the U.S. national stage application of International Patent Application No. PCT/IB2009/054155, filed Sep. 22, 2009, the disclosure of which is hereby incorporated by reference in its entirety, including all figures, tables and amino acid or nucleic acid sequences.

FIELD OF THE INVENTION

The present invention relates to pyrazolo pyridine derivatives of Formula (I), pharmaceutical composition thereof and to their use for the preparation of a medicament for the treatment and/or prophylaxis of cardiovascular diseases, respiratory disorders, disorders affecting the metabolism, skin and/or bone diseases, neurodegenerative diseases, kidney diseases, reproduction disorders, inflammatory disorders and cancers. Specifically, the present invention is related to pyrazolo pyridine derivatives useful for the preparation of a pharmaceutical formulation for the modulation, notably the inhibition of the activity or function of the Nicotinamide adenine dinucleotide phosphate oxidase (NADPH Oxidase).

BACKGROUND OF THE INVENTION

NADPH oxidases (NOX) are proteins that transfer electrons across biological membranes. In general, the electron acceptor is oxygen and the product of the electron transfer reaction is superoxide. The biological function of NOX enzymes is therefore the generation of reactive oxygen species (ROS) from oxygen. Reactive oxygen species (ROS) are oxygen-derived small molecules, including oxygen radicals (super-oxide anion [$^\bullet O_2^-$], hydroxyl [$HO^\bullet$], peroxyl [$ROO^\bullet$], alkoxyl [$RO^\bullet$.] and hydroperoxyl [$HOO^\bullet$]) and certain non-radicals that are either oxidizing agents and/or are easily converted into radicals. Nitrogen-containing oxidizing agents, such as nitric oxide are also called reactive nitrogen species (RNS). ROS generation is generally a cascade of reactions that starts with the production of superoxide. Superoxide rapidly dismutates to hydrogen peroxide either spontaneously, particularly at low pH or catalyzed by superoxide dismutase. Other elements in the cascade of ROS generation include the reaction of superoxide with nitric oxide to form peroxynitrite, the peroxidase-catalyzed formation of hypochlorous acid from hydrogen peroxide, and the iron-catalyzed Fenton reaction leading to the generation of hydroxyl radical.

ROS avidly interact with a large number of molecules including other small inorganic molecules as well as DNA, proteins, lipids, carbohydrates and nucleic acids. This initial reaction may generate a second radical, thus multiplying the potential damage. ROS are involved not only in cellular damage and killing of pathogens, but also in a large number of reversible regulatory processes in virtually all cells and tissues. However, despite the importance of ROS in the regulation of fundamental physiological processes, ROS production can also irreversibly destroy or alter the function of the target molecule. Consequently, ROS have been increasingly identified as major contributors to damage in biological organisms, so-called "oxidative stress".

During inflammation, NADPH oxidase is one of the most important sources of ROS production in vascular cells under inflammatory conditions (Thabut et al., 2002, J. Biol. Chem., 277:22814-22821).

In the lung, tissues are constantly exposed to oxidants that are generated either endogenously by metabolic reactions (e.g. by mitochondrial respiration or activation of recruited inflammatory cells) or exogenously in the air (e.g. cigarette smoke or air pollutants). Further, the lungs, constantly exposed to high oxygen tensions as compared to other tissues, have a considerable surface area and blood supply and are particularly susceptible to injury mediated by ROS (Brigham, 1986, Chest, 89(6): 859-863). NADPH oxidase-dependent ROS generation has been described in pulmonary endothelial cells and smooth muscle cells. NADPH oxidase activation in response to stimuli has been thought to be involved in the development of respiratory disorders such as pulmonary hypertension and enhancement of pulmonary vasoconstriction (Djordjevic et al., 2005, Arterioscler. Thromb. Vasc. Biol., 25, 519-525; Liua et al., 2004, Am. J. Physiol. Lung, Cell. Mol. Physiol., 287: L111-118). Further, pulmonary fibrosis has been characterized by lung inflammation and excessive generation of ROS.

Osteoclasts, which are macrophage-like cells that play a crucial role in bone turn-over (e.g. bone resorption), generate ROS through NADPH oxidase-dependent mechanisms (Yang et al., 2002, J. Cell. Chem. 84, 645-654).

Diabetes is known to increase oxidative stress (e.g. increased generation of ROS by auto-oxidation of glucose) both in humans and animals and increased oxidative stress has been said to play an important role in the development of diabetic complications. It has been shown that increased peroxide localization and endothelial cell dysfunction in the central retina of diabetic rats coincides with the areas of NADPH oxidase activity in the retinal endothelial cells (Ellis et al., 2000, Free Rad. Biol. Med., 28:91-101). Further, it has been suggested that controlling oxidative stress (ROS) in mitochondria and/or inflammation may be a beneficial approach for the treatment of diabetes (Pillarisetti et al., 2004, Expert Opin. Ther. Targets, 8(5):401-408).

ROS are also strongly implicated in the pathogenesis of atherosclerosis, cell proliferation, hypertension and reperfusion injury cardiovascular diseases in general (Cai et al., 2003, Trends Pharmacol. Sci., 24:471-478). Not only is superoxide production, for example in the arterial wall, increased by all risk factors for atherosclerosis, but ROS also induce many "proatherogenic" in vitro cellular responses. An important consequence of the formation of ROS in vascular cells is the consumption of nitric oxide (NO). NO inhibits the development of vascular diseases, and loss of NO is important in the pathogenesis of cardiovascular diseases. The increase in NADPH oxidase activity in vascular wall after balloon injury has been reported (Shi et al., 2001, Thromb. Vasc. Biol., 2001, 21, 739-745).

It is believed that oxidative stress or free radical damage is also a major causative factor in neurodegenerative diseases. Such damages may include mitochondrial abnormalities, neuronal demyelination, apoptosis, neuronal death and reduced cognitive performance, potentially leading to the development of progressive neurodegenerative disorders (Nunomura et al., 2001, J. Neuropathol. Exp. Neurol., 60:759-767; Girouard, 2006, J. Appl. Physiol. 100:328-335).

Further, the generation of ROS by sperm has been demonstrated in a large number of species and has been suggested to be attributed to an NADPH oxidase within spermatozoa (Vernet et al., Biol. Reprod., 2001, 65:1102-1113). Excessive ROS generation has been suggested to be implicated in sperm pathology, including male infertility and also in some penile disorders and prostate cancer.

NADPH oxidases are multi-subunit enzymes made up of a membrane-bound cytochrome b558 domain and three cytosolic protein subunits, p47phox, p67phox and a small GTPase, Rac. Seven isoforms of NOX enzymes have been identified including NOX1, NOX2, NOX3, NOX4, NOX5, DUOX1 and DUOX2 (Leto et al., 2006, *Antioxid Redox Signal,* 8(9-10):1549-61; Cheng et al., 2001, *Gene,* 16; 269(1-2):131-40).

Thus, ROS derived from NADPH contribute to the pathogenesis of numerous diseases, especially cardiovascular diseases or disorders, respiratory disorder or disease, disease or disorder affecting the metabolism, bone disorders, neurodegenerative diseases, inflammatory diseases, reproduction disorder or disease, pain, cancer and disease or disorders of the gastrointestinal system. Therefore, it would be highly desirable to develop new active agents focusing on the ROS signalling cascade, especially on NADPH oxidases (NOX).

SUMMARY OF THE INVENTION

The present invention is directed towards new molecules useful in the treatment and/or prophylaxis of Nicotinamide adenine dinucleotide phosphate oxidase (NADPH Oxidase) related disorders such as cardiovascular diseases, respiratory disorders, disorders affecting the metabolism, skin and/or bone diseases, neurodegenerative diseases, kidney diseases, reproduction disorders, inflammatory disorders, cancers, allergic disorders, traumatisms, septic, hemorrhagic and anaphylactic shock, diseases or disorders of the gastrointestinal system and angiogenesis and angiogenesis-dependent. Notably, the invention is related to new molecules useful in the inhibition or reduction of ROS production in cells.

A first aspect of the invention provides a pyrazolo pyridine derivative according to Formula (I), wherein $G_1$, $G_2$, $G_3$, $G_4$ and $G_5$ are as defined below, as well as pharmaceutically acceptable salts and pharmaceutically active derivative thereof.

A second aspect of the invention relates to a pyrazolo pyridine derivative according to Formula (I), wherein $G_1$, $G_2$, $G_3$, $G_4$ and $G_5$ are as defined below, as well as pharmaceutically acceptable salts and pharmaceutically active derivative thereof for use as a medicament.

A third aspect of the invention relates to a pharmaceutical composition containing at least one a pyrazolo pyridine derivative according to the invention, as well as pharmaceutically acceptable salts and pharmaceutically active derivative thereof and a pharmaceutically acceptable carrier, diluent or excipient thereof.

A fourth aspect of the invention resides in a use of a pyrazolo pyridine derivative according to the invention as well as pharmaceutically acceptable salts and pharmaceutically active derivative thereof for the preparation of a pharmaceutical composition for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system, angiogenesis and angiogenesis-dependent and/or other diseases and disorders associated with Nicotinamide adenine dinucleotide phosphate oxidase (NADPH Oxidase).

A fifth aspect of the invention relates to a method for treating a patient suffering from a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system, angiogenesis and angiogenesis-dependent and other diseases and/or disorders associated with Nicotinamide adenine dinucleotide phosphate oxidase (NADPH Oxidase). The method comprises administering a pyrazolo pyridine derivative according to Formula (I), wherein $G_1$, $G_2$, $G_3$, $G_4$ and $G_5$ are as defined below, as well as pharmaceutically acceptable salts and pharmaceutically active derivative thereof in a patient in need thereof.

A sixth aspect of the invention relates to a pyrazolo pyridine derivative according to Formula (I), wherein $G_1$, $G_2$, $G_3$, $G_4$ and $G_5$ are as defined below, as well as pharmaceutically acceptable salts and pharmaceutically active derivative thereof, for the treatment of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system, angiogenesis and angiogenesis-dependent and other diseases and/or disorders associated with Nicotinamide adenine dinucleotide phosphate oxidase (NADPH Oxidase).

Other features and advantages of the invention will be apparent from the following detailed description.

DETAILED DESCRIPTION OF THE INVENTION

The following paragraphs provide definitions of the various chemical moieties that make up the compounds according to the invention and are intended to apply uniformly through-out the specification and claims, unless an otherwise expressly set out definition provides a broader definition.

The term "alkyl" when used alone or in combination with other terms, comprises a straight chain or branched $C_1$-$C_{20}$ alkyl which refers to monovalent alkyl groups having 1 to 20 carbon atoms. This term is exemplified by groups such as methyl, ethyl, n-propyl, i-propyl, n-butyl, s-butyl, i-butyl, t-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, n-heptyl, 2-methylhexyl, 3-methylhexyl, 4-methylhexyl, 5-methylhexyl, n-heptyl, n-octyl, n-nonyl, n-decyl, tetrahydrogeranyl, n-dodecyl, n-tridecyl, n-tetradecyl, n-pentadecyl, n-hexadecyl, n-octadecyl, n-nonadecyl, and n-eicosanyl and the like. Preferably, these include $C_1$-$C_9$ alkyl, more preferably $C_1$-$C_6$ alkyl, especially preferably $C_1$-$C_4$ alkyl, which, by analogy, refer respectively to monovalent alkyl groups having 1 to 9 carbon atoms, monovalent alkyl groups having 1 to 6 carbon atoms and monovalent alkyl groups having 1 to 4 carbon atoms. Particularly, those include $C_1$-$C_6$ alkyl.

The term "alkenyl" when used alone or in combination with other terms, comprises a straight chain or branched $C_2$-$C_{20}$ alkenyl. It may have any available number of double bonds in any available positions, and the configuration of the double bond may be the (E) or (Z) configuration. This term is exemplified by groups such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 1-heptenyl, 1-octenyl, geranyl, 1-decenyl, 1-tetradecenyl, 1-octadecenyl, 9-octadecenyl, 1-eicosenyl, and 3,7,11,15-tetramethyl-1-hexadecenyl, and the like. Preferably, these include $C_2$-$C_8$ alkenyl, more preferably $C_2$-$C_6$ alkenyl. Among others, especially preferred are vinyl or ethenyl (—CH=$CH_2$), n-2-propenyl (allyl, —$CH_2$CH=$CH_2$), isopropenyl, 1-propenyl, 2-methyl-1-propenyl, 1-butenyl, 2-butenyl, and 3-methyl-2-butenyl and the like.

The term "alkynyl" when used alone or in combination with other terms, comprises a straight chain or branched $C_2$-$C_{20}$ alkynyl. It may have any available number of triple bonds in any available positions. This term is exemplified by groups such as alkynyl groups that may have a carbon number of 2-20, and optionally a double bond, such as ethynyl (—C≡CH), 1-propynyl, 2-propynyl (propargyl: —$CH_2$C≡CH), 2-butynyl, 2-pentene-4-ynyl, and the like. Particularly, these include $C_2$-$C_8$ alkynyl, more preferably $C_2$-$C_6$ alkynyl and the like. Preferably those include $C_2$-$C_6$ alkynyl which refers to groups having 2 to 6 carbon atoms and having at least 1 or 2 sites of alkynyl unsaturation.

The term "heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl and the like.

The term "aryl" refers to an unsaturated aromatic carbocyclic group of from 6 to 14 carbon atoms having a single ring (e.g., phenyl) or multiple condensed rings (e.g., indenyl, naphthyl). Aryl include phenyl, naphthyl, anthryl, phenanthrenyl and the like.

The term "$C_1$-$C_6$ alkyl aryl" refers to aryl groups having an $C_1$-$C_6$ alkyl substituent, including methyl phenyl, ethyl phenyl and the like.

The term "aryl $C_1$-$C_6$ alkyl" refers to $C_1$-$C_6$ alkyl groups having an aryl substituent, including 3-phenylpropanyl, benzyl and the like.

The term "heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro] benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

The term "$C_1$-$C_6$ alkyl heteroaryl" refers to heteroaryl groups having a $C_1$-$C_6$ alkyl substituent, including methyl furyl and the like.

The term "heteroaryl $C_1$-$C_6$ alkyl" refers to $C_1$-$C_6$ alkyl groups having a heteroaryl substituent, including furyl methyl and the like.

The term "$C_2$-$C_6$ alkenyl aryl" refers to an aryl groups having a $C_2$-$C_6$ alkenyl substituent, including vinyl phenyl and the like.

The term "aryl $C_2$-$C_6$ alkenyl" refers to a $C_2$-$C_6$ alkenyl groups having an aryl substituent, including phenyl vinyl and the like.

The term "$C_2$-$C_6$ alkenyl heteroaryl" refers to heteroaryl groups having a $C_2$-$C_6$ alkenyl substituent, including vinyl pyridinyl and the like.

The term "heteroaryl $C_2$-$C_6$ alkenyl" refers to $C_1$-$C_6$ alkenyl groups having a heteroaryl substituent, including pyridinyl vinyl and the like.

The term "$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl includes cyclopentyl, cyclohexyl, norbornyl and the like.

The term "heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidinyl, piperidinyl, piperazinyl, morpholinyl, tetrahydrofuranyl and the like.

The term "$C_1$-$C_6$ alkyl $C_3$-$C_8$-cycloalkyl" refers to $C_3$-$C_8$-cycloalkyl groups having a $C_1$-$C_6$ alkyl substituent, including methyl cyclopentyl and the like.

The term "$C_3$-$C_8$-cycloalkyl $C_1$-$C_6$ alkyl" refers to $C_1$-$C_6$ alkyl groups having a $C_3$-$C_8$-cycloalkyl substituent, including 3-cyclopentyl propyl and the like.

The term "$C_1$-$C_6$ alkyl heterocycloalkyl" refers to heterocycloalkyl groups having a $C_1$-$C_6$ alkyl substituent, including 4-methylpiperidinyl and the like.

The term "heterocycloalkyl $C_1$-$C_6$ alkyl" refers to $C_1$-$C_6$ alkyl groups having a heterocycloalkyl substituent, including (1-methylpiperidin-4-yl)methyl and the like.

The term "carboxy" refers to the group —C(O)OH.

The term "carboxy $C_1$-$C_6$ alkyl" refers to $C_1$-$C_6$ alkyl groups having a carboxy substituent, including 2-carboxyethyl and the like.

The term "acyl" refers to the group —C(O)R where R includes H, "alkyl," preferably "$C_1$-$C_6$ alkyl," "aryl," "heteroaryl," "$C_3$-$C_8$-cycloalkyl," "heterocycloalkyl," "aryl $C_1$-$C_6$ alkyl," "heteroaryl $C_1$-$C_6$ alkyl," "$C_3$-$C_8$-cycloalkyl $C_1$-$C_6$ alkyl" or "heterocycloalkyl $C_1$-$C_6$ alkyl", including acetyl and the like.

The term "acyl $C_1$-$C_6$ alkyl" to $C_1$-$C_6$ alkyl groups having an acyl substituent, including 2-acetylethyl and the like.

The term "acyl aryl" refers to aryl groups having an acyl substituent, including 2-acetylphenyl and the like.

The term "acyloxy" refers to the group —OC(O)R where R includes H, "$C_1$-$C_6$ alkyl", "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", including acetyloxy and the like.

The term "acyloxy $C_1$-$C_6$ alkyl" refers to $C_1$-$C_6$ alkyl groups having an acyloxy substituent, including 2-(ethylcarbonyloxy)ethyl and the like.

The term "alkoxy" refers to the group —O—R where R includes "$C_1$-$C_6$ alkyl", "aryl", "heteroaryl", "aryl $C_1$-$C_6$ alkyl" or "heteroaryl $C_1$-$C_6$ alkyl". Preferred alkoxy groups include for example, methoxy, ethoxy, phenoxy and the like.

The term "alkoxy $C_1$-$C_6$ alkyl" refers to $C_1$-$C_6$ alkyl groups having an alkoxy substituent, including methoxyethyl and the like.

The term "alkoxycarbonyl" refers to the group —C(O)OR where R includes "$C_1$-$C_6$ alkyl", "aryl", "heteroaryl", "aryl $C_1$-$C_6$ alkyl", "heteroaryl $C_1$-$C_6$ alkyl" or "heteroalkyl".

The term "alkoxycarbonyl $C_1$-$C_6$ alkyl" refers to $C_1$-$C_6$ alkyl groups having an alkoxycarbonyl substituent, including 2-(benzyloxycarbonyl)ethyl and the like.

The term "aminocarbonyl" refers to the group —C(O)NRR' where R and R' are independently H, $C_1$-$C_6$ alkyl, aryl, heteroaryl, "aryl $C_1$-$C_6$ alkyl" or "heteroaryl $C_1$-$C_6$ alkyl," including N-phenyl carbonyl and the like.

The term "aminocarbonyl $C_1$-$C_6$ alkyl" refers to alkyl groups having an aminocarbonyl substituent, including 2-(dimethylaminocarbonyl)ethyl, N-ethyl acetamidyl, N,N-Diethyl-acetamidyl and the like.

The term "acylamino" refers to the group —NRC(O)R' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl", including acetylamino and the like.

The term "acylamino $C_1$-$C_6$ alkyl" refers to $C_1$-$C_6$ alkyl groups having an acylamino substituent, including 2-(propionylamino)ethyl and the like.

The term "ureido" refers to the group —NRC(O)NR'R" where R, R' and R" are independently H, "$C_1$-$C_6$ alkyl," "alkenyl," "alkynyl," "$C_3$-$C_8$-cycloalkyl," "heterocycloalkyl," "$C_1$-$C_6$ aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl," and where R' and R," together with the nitrogen atom to which they are attached, can optionally form a 3-8-membered heterocycloalkyl ring.

The term "ureido $C_1$-$C_6$ alkyl" refers to $C_1$-$C_6$ alkyl groups having an ureido substituent, including 2-(N'-methylureido) ethyl and the like.

The term "carbamate" refers to the group —NRC(O)OR' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "$C_1$-$C_6$ alkyl aryl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl" and optionally R can also be hydrogen.

The term "amino" refers to the group —NRR' where R and R' are independently H, "$C_1$-$C_6$ alkyl", "aryl", "heteroaryl", "$C_1$-$C_6$ alkyl aryl", "$C_1$-$C_6$ alkyl heteroaryl," "cycloalkyl," or "heterocycloalkyl," and where R and R', together with the nitrogen atom to which they are attached, can optionally form a 3-8-membered heterocycloalkyl ring.

The term "amino alkyl" refers to alkyl groups having an amino substituent, including 2-(1-pyrrolidinyl)ethyl and the like.

The term "ammonium" refers to a positively charged group —N+RR'R" where R, R' and R" are independently "$C_1$-$C_6$ alkyl", "$C_1$-$C_6$ alkyl aryl", "$C_1$-$C_6$ alkyl heteroaryl," "cycloalkyl," or "heterocycloalkyl," and where R and R', together with the nitrogen atom to which they are attached, can optionally form a 3-8-membered heterocycloalkyl ring.

The term "ammonium alkyl" refers to alkyl groups having an ammonium substituent, including 1-ethylpyrrolidinium and the like.

The term "halogen" refers to fluoro, chloro, bromo and iodo atoms.

The term "sulfonyloxy" refers to a group —OSO$_2$—R wherein R is selected from "$C_1$-$C_6$ alkyl," "$C_1$-$C_6$ alkyl" substituted with halogens, e.g., an —OSO$_2$—CF$_3$ group, "$C_2$-$C_6$ alkenyl," "alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl alkyl".

The term "sulfonyloxy $C_1$-$C_6$ alkyl" refers to alkyl groups having a sulfonyloxy substituent, including 2-(methylsulfonyloxy)ethyl and the like.

The term "sulfonyl" refers to group "—SO$_2$—R" wherein R is selected from "aryl," "heteroaryl," "$C_1$-$C_6$ alkyl," "$C_1$-$C_6$ alkyl" substituted with halogens, e.g., an —SO$_2$—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl".

The term "sulfonyl $C_1$-$C_6$ alkyl" refers to alkyl groups having a sulfonyl substituent, including 2-(methylsulfonyl)ethyl and the like.

The term "sulfinyl" refers to a group "—S(O)—R" wherein R is selected from "alkyl," "alkyl" substituted with halogens, e.g., a —SO—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfinyl alkyl" refers to alkyl groups having a sulfinyl substituent, including 2-(methylsulfinyl)ethyl and the like.

The term "sulfanyl" refers to groups —S—R where R includes H, "$C_1$-$C_6$ alkyl," "$C_1$-$C_6$ alkyl" substituted with halogens, e.g., a —S—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "alkynylheteroaryl," "cycloalkyl $C_1$-$C_6$ alkyl," or "heterocycloalkyl $C_1$-$C_6$ alkyl". Preferred sulfanyl groups include methylsulfanyl, ethylsulfanyl, and the like.

The term "sulfanyl $C_1$-$C_6$ alkyl" refers to $C_1$-$C_5$-alkyl groups having a sulfanyl substituent, including 2-(ethylsulfanyl)ethyl and the like.

The term "sulfonylamino" refers to a group —NRSO$_2$—R' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfonylamino $C_1$-$C_6$ alkyl" refers to alkyl groups having a sulfonylamino substituent, including 2-(ethylsulfonylamino)ethyl and the like.

The term "aminosulfonyl" refers to a group —SO$_2$—NRR' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", and where R and R', together with the nitrogen atom to which they are attached, can optionally form a 3-8-membered heterocycloalkyl ring. Aminosulfonyl groups include cyclohexylaminosulfonyl, piperidinylsulfonyl and the like.

The term "aminosulfonyl $C_1$-$C_6$ alkyl" refers to $C_1$-$C_6$ alkyl groups having an aminosulfonyl substituent, including 2-(cyclohexylaminosulfonyl)ethyl and the like.

Unless otherwise constrained by the definition of the individual substituent, all the above substituents should be understood as being all optionally substituted.

Unless otherwise constrained by the definition of the individual substituent, the term "substituted" refers to groups substituted with from 1 to 5 substituents selected from the group consisting of "$C_1$-$C_6$ alkyl," "$C_2$-$C_6$ alkenyl," "$C_2$-$C_6$ alkynyl," "$C_3$-$C_8$-cycloalkyl," "heterocycloalkyl," "$C_1$-$C_6$ alkyl aryl," "$C_1$-$C_6$ alkyl heteroaryl," "$C_1$-$C_6$ alkyl cycloalkyl," "$C_1$-$C_6$ alkyl heterocycloalkyl," "amino," "aminosulfonyl," "ammonium," "acyl amino," "amino carbonyl," "aryl," "heteroaryl," "sulfinyl," "sulfonyl," "alkoxy," "alkoxy carbonyl," "carbamate," "sulfanyl," "halogen," trihalomethyl, cyano, hydroxy, mercapto, nitro, and the like.

The term "pharmaceutically acceptable salts or complexes" refers to salts or complexes of the below-specified compounds of Formula (I). Examples of such salts include, but are not restricted to, base addition salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from two acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. The prodrug is a derivative of the compound according to the invention and presenting NADPH oxidase inhibiting activity that has a chemically or metabolically decomposable group, and a compound that may be converted into a pharmaceutically active compound in vivo by solvolysis under physiological conditions. The invention further encompasses any tautomers of the compounds according to the invention.

The term "cardiovascular disorder or disease" comprises atherosclerosis, especially diseases or disorders associated with endothelial dysfunction including but not limited to hypertension, cardiovascular complications of Type I or Type II diabetes, intimal hyperplasia, coronary heart disease, cerebral, coronary or arterial vasospasm, endothelial dysfunction, heart failure including congestive heart failure, peripheral artery disease, restenosis, trauma caused by a stent, stroke, ischemic attack, vascular complications such as after organ transplantation, myocardial infarction, hypertension, formation of atherosclerotic plaques, platelet aggregation, angina pectoris, aneurysm, aortic dissection, ischemic heart disease, cardiac hypertrophy, pulmonary embolus, thrombotic events including deep vein thrombosis, injury caused after ischemia by restoration of blood flow or oxygen delivery as in organ transplantation, open heart surgery, angioplasty, hemorrhagic shock, angioplasty of ischemic organs including heart, brain, liver, kidney, retina and bowel.

The term "respiratory disorder or disease" comprises bronchial asthma, bronchitis, allergic rhinitis, adult respiratory syndrome, cystic fibrosis, lung viral infection (influenza), pulmonary hypertension, idiopathic pulmonary fibrosis and chronic obstructive pulmonary diseases (COPD).

The term "allergic disorder" includes hay fever and asthma.

The term "traumatism" includes polytraumatism.

The term "disease or disorder affecting the metabolism" includes obesity, metabolic syndrome and Type II diabetes.

The term "skin disease" or disorder" includes psoriasis, eczema, dermatitis, wound healing and scar formation.

The term "bone disorder" includes osteoporosis, osteoporasis, osteosclerosis, periodontitis, and hyperparathyroidism.

The term "neurodegenerative disease or disorder" comprises a disease or a state characterized by a central nervous system (CNS) degeneration or alteration, especially at the level of the neurons such as Alzheimer's disease, Parkinson's disease, Huntington's disease, amyotrophic lateral sclerosis, epilepsy and muscular dystrophy. It further comprises neuroinflammatory and demyelinating states or diseases such as leukoencephalopathies, and leukodystrophies.

The term "demyelinating" is referring to a state or a disease of the CNS comprising the degradation of the myelin around the axons. In the context of the invention, the term demyelinating disease is intended to comprise conditions which comprise a process that demyelinate cells such as multiple sclerosis, progressive multifocal leukoencephalopathy (PML), myelopathies, any neuroinflammatory condition involving autoreactive leukocyte within the CNS, congenital metabolic disorder, a neuropathy with abnormal myelination, drug induced demyelination, radiation induced demyelination, a hereditary demyelinating condition, a prion induced demyelinating condition, encephalitis induced demyelination or a spinal cord injury. Preferably, the condition is multiple sclerosis.

The term "kidney disease or disorder" includes diabetic nephropathy, renal failure, glomerulonephritis, nephrotoxicity of aminoglycosides and platinum compounds and hyperactive bladder. In a particular embodiment, the term according to the invention includes chronic kidney diseases or disorders.

The term "reproduction disorder or disease" includes erectile dysfunction, fertility disorders, prostatic hypertrophy and benign prostatic hypertrophy.

The term "disease or disorder affecting the eye and/or the lens" includes cataract including diabetic cataract, re-opacification of the lens post cataract surgery, diabetic and other forms of retinopathy.

The term "conditions affecting the inner ear" includes presbyacusis, tinnitus, Meniere's disease and other balance problems, utriculolithiasis, vestibular migraine, and noise induced hearing loss and drug induced hearing loss (ototoxicity).

The term "inflammatory disorder or disease" means inflammatory bowel disease, sepsis, septic shock, adult respiratory distress syndrome, pancreatitis, shock induced by trauma, bronchial asthma, allergic rhinitis, rheumatoid arthritis, chronic rheumatoid arthritis, arteriosclerosis, intracerebral hemorrhage, cerebral infarction, heart failure, myocardial infarction, psoriasis, cystic fibrosis, stroke, acute bronchitis, chronic bronchitis, acute bronchiolitis, chronic bronchiolitis, osteoarthritis, gout, myelitis, ankylosing spondylitis, Reuter syndrome, psoriatic arthritis, spondylarthritis, juvenile arthritis or juvenile ankylosing spondylitis, reactive arthritis, infectious arthritis or arthritis after infection, gonococcal arthritis, syphilitic arthritis, Lyme disease, arthritis induced by "angiitis syndrome," polyarteritis nodosa, anaphylactic angiitis, Luegenec granulomatosis, rheumatoid polymyalgia, articular cell rheumatism, calcium crystal deposition arthritis, pseudogout, non-arthritic rheumatism, bursitis, tendosynovitis, epicondyle inflammation (tennis elbow), carpal tunnel syndrome, disorders by repetitive use (typing), mixed form of arthritis, neuropathic arthropathy, hemorrhagic arthritis, vascular peliosis, hypertrophic osteoarthropathy, multicentric reticulohistiocytosis, arthritis induced by specific diseases, blood pigmentation, sickle cell disease and other hemoglobin abnormality, hyperlipoproteinemia, dysgammaglobulinemia, hyperparathyroidism, acromegaly, familial Mediterranean fever, Bechet's disease, systemic autoimmune disease erythematosus, multiple sclerosis and Crohn's disease or diseases like relapsing polychondritis, chronic inflammatory bowel diseases (IBD) or the related diseases which require the administration to a mammal in a therapeutic effective dose of a compound expressed by Formula (I) in a sufficient dose to inhibit NADPH oxidase.

The term liver diseases or disorders include liver fibrosis, alcohol induced fibrosis, steatosis and non alcoholic steatohepatitis.

The term "arthritis" means acute rheumatic arthritis, chronic rheumatoid arthritis, chlamydial arthritis, chronic absorptive arthritis, chylous arthritis, arthritis based on bowel disease, filarial arthritis, gonorrheal arthritis, gouty arthritis, hemophilic arthritis, hypertrophic arthritis, juvenile chronic arthritis, Lyme arthritis, neonatal foal arthritis, nodular arthritis, ochronotic arthritis, psoriatic arthritis or suppurative arthritis, or the related diseases which require the administration to a mammal in a therapeutic effective dose of a compound expressed by Formula (I) in a sufficient dose to inhibit NADPH oxidase.

The term "pain" includes hyperalgesia associated with inflammatory pain.

The term "cancer" means carcinoma (e.g., fibrosarcoma, myxosarcoma, liposarcoma, chondrosarcoma, osteogenic sarcoma, chordoma, angiosarcoma, endothelium sarcoma, lymphangiosarcoma, lymphangioendothelioma, periosteoma, mesothelioma, Ewing's tumor, leiomyosarcoma, rhabdomyosarcoma, colon carcinoma, pancreatic cancer, breast cancer, ovarian cancer, renal cancer, prostatic carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, cholangiocarcinoma, choriocarcinoma, seminoma, embryonal carcinoma, Wilms' tumor, cervical cancer, orchioncus, lung cancer, small-cell lung cancer, lung adenocarcinoma, bladder cancer or epithelial cancer) or the related diseases which require the administration to a mammal in a therapeutic effective dose of a compound expressed by the Formula (I) in a sufficient dose to inhibit NADPH oxidase.

The term "disease or disorders of the gastrointestinal system", includes gastric mucosa disorders ischemic bowel disease management, enteritis/colitis, cancer chemotherapy, or neutropenia.

The term "angiogenesis" includes sprouting angiogenesis, intussusceptive angiogenesis, vasculogenesis, arteriogenesis and lymphangiogenesis. Angiogenesis is the formation of new blood vessels from pre-existing capillaries or post-capillary venules and occurs in pathological conditions such as cancers, arthritis and inflammation. A large variety of tissues, or organs comprised of organized tissues, can support angiogenesis in disease conditions including skin, muscle, gut, connective tissue, joints, bones and the like tissue in which blood vessels can invade upon angiogenic stimuli. As used herein, the term "angiogenesis-dependent condition" is intended to mean a condition where the process of angiogenesis or vasculogenesis sustains or augments a pathological condition. Vasculogenesis results from the formation of new blood vessels arising from angioblasts which are endothelial cell precursors. Both processes result in new blood vessel formation and are included in the meaning of the term angiogenesis-dependent conditions. Similarly, the term "angiogenesis" as used herein is intended to include de novo formation of vessels such as those arising from vasculogenesis as well as those arising from branching and sprouting of existing vessels, capillaries and venules.

The term "angiogenesis inhibitory," means that which is effective in the decrease in the extent, amount, or rate of neovascularization. Effecting a decrease in the extent, amount, or rate of endothelial cell proliferation or migration in the tissue is a specific example of inhibiting angiogenesis. Angiogenesis inhibitory activity is particularly useful in the treatment of any cancers as it targets tumor growth process and in the absence of neovascularization of tumor tissue, the tumor tissue does not obtain the required nutrients, slows in growth, ceases additional growth, regresses and ultimately becomes necrotic resulting in killing of the tumor. Further, an angiogenesis inhibitory activity is particularly useful in the treatment of any cancers as it is particularly effective against the formation of metastases because their formation also requires vascularization of a primary tumor so that the metastatic cancer cells can exit the primary tumor and their establishment in a secondary site requires neovascularization to support growth of the metastases.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions.

The term "subject" as used herein refers to mammals. For examples, mammals contemplated by the present invention include human, primates, domesticated animals such as cattle, sheep, pigs, horses and the like.

The term "inhibitor" used in the context of the invention is defined as a molecule that inhibits completely or partially the activity of NADPH oxidase and/or inhibit or reduce the generation of reactive oxygen species (ROS).

Compounds According to the Invention

In one embodiment, the invention provides a pyrazolo pyridine derivative according to Formula (I):

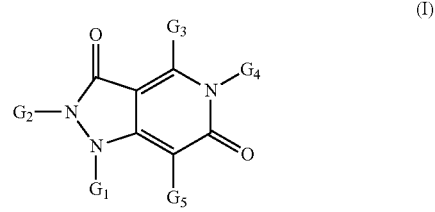

(I)

wherein $G_1$ is selected from H; optionally substituted acyl; optionally substituted acyl $C_1$-$C_6$ alkyl, optionally substituted alkyl such as aminocarbonyl alkyl (e.g. phenylacetamide), optionally substituted $C_3$-$C_8$-cycloalkyl alkyl, optionally substituted heterocycloalkyl alkyl, optionally substituted aryl alkyl such as optionally substituted phenyl alkyl like optionally substituted phenyl methyl (e.g. phenyl methyl or 3-methyl phenyl methyl or 4-fluorobenzyl or 2-chlorobenzyl or 4-chlorobenzyl or 4-methyl benzyl or 4-bromobenzyl); and optionally substituted heteroaryl alkyl such as optionally substituted pyridine alkyl like pyridine-2-yl methyl; $G_2$ is selected from —$CHR^1R^2$ and an optionally substituted saturated ring system selected from optionally substituted $C_3$-$C_8$-cycloalkyl such as optionally substituted cyclohexyl and optionally substituted heterocycloalkyl such as optionally substituted piperidine (e.g. 1-methylpiperidin-4yl); $R^1$ and $R^2$ are independently selected from H; optionally substituted alkoxy; optionally substituted alkoxy $C_1$-$C_6$ alkyl such as optionally substituted methoxy (e.g. 2-methoxy methyl or 2-methoxy 4-chlorophenyl); optionally substituted amino; optionally substituted aminoalkyl such as optionally substituted amino methyl (e.g. 2-diethylamino methyl); optionally substituted acyl; optionally substituted $C_1$-$C_6$ alkyl such as methyl, optionally substituted propyl (e.g. isopropyl); optionally substituted $C_2$-$C_6$ alkenyl; optionally substituted $C_2$-$C_6$ alkynyl; optionally substituted aryl such as optionally substituted phenyl (e.g. phenyl, 4-chlorophenyl or 2,5 dichlorophenyl or 2-chloro 4-fluorophenyl); optionally substituted $C_1$-$C_6$ alkyl aryl; optionally substituted aryl $C_1$-$C_6$ alkyl such as optionally substituted phenyl $C_1$-$C_6$ alkyl (e.g. optionally substituted phenyl methyl like 2-phenyl methyl); optionally substituted heteroaryl; optionally substituted $C_1$-$C_6$ alkyl heteroaryl; optionally substituted heteroaryl $C_1$-$C_6$ alkyl such as optionally substituted morpholinyl $C_1$-$C_6$ alkyl (e.g. 2-morpholin-4-ylethyl); optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl such as optionally substituted cyclohexyl (e.g. cyclohexyl); optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl such as optionally substituted morpholinyl $C_1$-$C_6$ alkyl (e.g. optionally substituted morpholinyl methyl such as 2-morpholin-4yl methyl); or —$CHR^1R^2$ form together an optionally substituted ring selected from optionally substituted $C_3$-$C_8$-cycloalkyl such as an optionally substituted cyclohexyl (e.g. cyclohexyl) and optionally substituted heterocycloalkyl such as an optionally substituted piperidine (e.g. 1-methyl piperidine 4-yl) or an optionally substituted pyrrolidine; $G_3$ is selected from H; optionally substituted amino; optionally substituted aminoalkyl such as benzyl(methyl)amino methyl; optionally substituted aminocarbonyl; optionally substituted alkoxy; optionally substituted alkoxy $C_1$-$C_6$ alkyl such as an optionally substituted phenoxy $C_1$-$C_6$ alkyl (e.g. 4-fluorophenoxy methyl or 4-chlorophenoxy methyl or 3-phenoxy propyl or 4-benzyloxy methyl); optionally substituted acyl; optionally substituted $C_1$-$C_6$ alkyl such as methyl, ethyl, butyl (e.g. 4-butyl); optionally substituted $C_2$-$C_6$ alkenyl; optionally substituted $C_2$-$C_6$ alkynyl; optionally substituted aryl such as optionally substituted phenyl (e.g. phenyl, 3-chlorophenyl, 3,4 dichlorophenyl or 4-chlorophenyl or 3,5 dichlorophenyl); optionally substituted $C_1$-$C_6$ alkyl aryl; optionally substituted aryl $C_1$-$C_6$ alkyl such as optionally substituted phenyl $C_1$-$C_6$ alkyl like optionally substituted benzyl (e.g. 3-methoxy benzyl); optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl such as optionally substituted piperidin (e.g. methyl piperidine-1-carboxylate); optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl such as optionally substituted morpholinyl $C_1$-$C_6$ alkyl (e.g. morpholin-4ylmethyl); $G_4$ is selected from H; optionally substituted acyl; optionally substituted acyl amino; optionally substituted acyl $C_1$-$C_6$ alkyl such as optionally substituted acyl methyl (e.g. morpholino 4-acetyl-, piperazine 1-acetyl-4-(phenylmethyl)-; optionally substituted $C_1$-$C_6$ alkyl such as optionally substituted methyl (e.g. methyl) or optionally substituted pentyl (e.g. isopentyl) or optionally substituted acyl amino $C_1$-$C_6$ alkyl such as optionally substituted benzamide $C_1$-$C_6$ alkyl (e.g. 4-fluorobenzamide ethyl) or optionally substituted heteroalkyl such as substituted alkoxy $C_1$-$C_6$ alkyl like optionally substituted methoxy $C_1$-$C_6$ alkyl (e.g. 2-methoxyethyl), optionally substituted ethoxy $C_1$-$C_6$ alkyl (e.g. 3-ethoxy propyl), optionally substituted phenoxy $C_1$-$C_6$ alkyl (e.g. 3-phenoxy propyl); optionally substituted $C_2$-$C_6$ alkenyl; optionally substituted $C_2$-$C_6$ alkynyl; optionally substituted aryl, such as optionally substituted phenyl (e.g. trifluoromethoyxyphenyl or phenyl acetamide); optionally substituted $C_1$-$C_6$ alkyl aryl; optionally substituted aryl $C_1$-$C_6$ alkyl such as optionally substituted phenyl methyl (e.g. benzoic acid methyl or benzyl (e.g. 2-benzyl) or dimethoxy benzyl or 3,5 dimethoxy benzyl or 3-methoxy benzyl or 4-methoxy benzyl or 4-chlorobenzyl or morpholin-4-ylmethyl benzyl or phenyl acetamide methyl) or optionally substituted phenyl ethyl (e.g. 2-phenyl ethyl, 4-methoxyphenyl ethyl); optionally substituted heteroaryl such as optionally substituted dihydroindenyl (e.g. 2,3-dihydro-1H-inden-1-yl); optionally substituted $C_1$-$C_6$ alkyl heteroaryl; optionally substituted heteroaryl $C_1$-$C_6$ alkyl such as optionally substituted thiophenyl $C_1$-$C_6$ alkyl like optionally substituted thiophenyl methyl (e.g. thiophen-2-yl methyl) or optionally substituted imidazolyl $C_1$-$C_6$ alkyl like optionally substituted imidazolyl ethyl (e.g. imidazol-4-yl ethyl) or optionally substituted indolyl $C_1$-$C_6$ alkyl like optionally substituted indolyl ethyl (e.g. indol-3-yl ethyl) or optionally substituted furanyl $C_1$-$C_6$ alkyl like optionally substituted furanyl methyl (e.g. furan-2-yl methyl) or optionally substituted benzodioxolyl $C_1$-$C_6$ alkyl like optionally substituted benzodioxolyl methyl (e.g. 1,3-benzodioxol-5-yl methyl) or optionally substituted pyridinyl $C_1$-$C_6$ alkyl like optionally substituted pyridinyl methyl (e.g. pyridine-3-yl methyl or pyridin-2-yl methyl or 1-acetylpiperidin-4-yl methyl or tert-butyl piperidine-1-carboxylate methyl) or like optionally substituted pyridinyl ethyl (e.g. pyridin-2-yl ethyl) or optionally substituted morpholinyl $C_1$-$C_6$ alkyl like optionally substituted morpholinyl methyl (e.g. 4-benzylmorpholin-2yl methyl) or optionally substituted pyrrolidin $C_1$-$C_6$ alkyl like optionally substituted pyrrolidin methyl (e.g. 5-oxopyrrolidin-3-yl methyl); optionally substituted $C_2$-$C_6$ alkenyl aryl; optionally substituted aryl $C_2$-$C_6$ alkenyl; optionally substituted alkenyl heteroaryl; optionally substituted heteroaryl $C_2$-$C_6$ alkenyl; optionally substituted $C_3$-$C_8$-cycloalkyl; optionally substituted heterocycloalkyl such as optionally substituted morpholinyl (e.g. 5-morpholin-4-yl) or optionally substituted piperazinyl (e.g. 4-methyl piperazinyl) or optionally substituted piperidinyl (e.g. 4-methylbenzyl)piperidin-4-yl); optionally substituted $C_1$-$C_6$ alkyl $C_3$-$C_8$-cycloalkyl; optionally substituted $C_3$-$C_8$- cycloalkyl $C_1$-$C_6$ alkyl; optionally substituted $C_1$-$C_6$ alkyl heterocycloalkyl and optionally substituted heterocycloalkyl $C_1$-$C_6$ alkyl such as optionally substituted morpholinyl $C_1$-$C_6$ alkyl like optionally substituted morpholinyl propyl (e.g. 3-(morpholin-4-yl)propyl)) optionally substituted morpholinyl ethyl (e.g. 2-morpholin-4-ylethyl); or optionally substituted piperazinyl $C_1$-$C_6$ alkyl like optionally substituted piperazinyl ethyl (e.g. 2-(4-acetylpiperazin-1-yl)ethyl or 2-(4-hexanoyl piperazin-1-yl)ethyl) or optionally substituted pyrrolidinyl $C_1$-$C_6$ alkyl like optionally substituted pyrrolidinyl propyl (e.g. 3-(2-oxopyrrolidin-1-yl)propyl) or optionally substituted tetrahydrofuranyl $C_1$-$C_6$ alkyl like optionally substituted tetrahydrofuranyl methyl (e.g. tetrahydrofuran-2-yl methyl); $G_5$ is selected from H; optionally substituted $C_1$-$C_6$ alkyl; optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; as well as pharmaceutically acceptable salts and pharmaceutically active derivative thereof.

Compositions

The invention provides pharmaceutical or therapeutic agents as compositions and methods for treating a patient, preferably a mammalian patient, and most preferably a human patient who is suffering from a medical disorder, and in particular a disorder mediated by NADPH oxidase, such as a cardiovascular disorder or disease, a respiratory disorder or disease, a disease or disorder affecting the metabolism, a skin disorder, a bone disorder, a neuroinflammatory disorder, a neurodegenerative disorder, a kidney disease, a reproduction disorder, a disease or disorder affecting the eye and/or the lens, a condition affecting the inner ear, an inflammatory disorder or disease, a liver disease, pain, a cancer, angiogenesis, angiogenesis-dependent conditions and/or a disease or disorders of the gastrointestinal system.

Pharmaceutical compositions of the invention can contain one or more pyrazolo pyridine derivative in any form described herein. Compositions of this invention may further comprise one or more pharmaceutically acceptable additional ingredient(s), such as alum, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. Compositions according to the invention are preferably injectable.

Compositions of this invention may also be liquid formulations, including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives, including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in Part 5 of *Remington's Pharmaceutical Sciences, 21st Edition, 2005, University of the Sciences in Philadelphia, Lippincott Williams & Wilkins*, which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides. Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration, including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the stratum corneum, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting compounds across the stratum corneum.

The compounds of this invention can also be administered in sustained release forms or from sustained release drug delivery systems. A description of representative sustained release materials can also be found in the incorporated materials in *Remington's Pharmaceutical Sciences*.

Mode of Administration

Compositions of this invention may be administered in any manner, including, but not limited to, orally, parenterally, sublingually, transdermally, rectally, transmucosally, topically, via inhalation, via buccal or intranasal administration, or combinations thereof. Parenteral administration includes, but is not limited to, intravenous, intra-arterial, intra-peritoneal, subcutaneous, intramuscular, intra-thecal, and intra-articular. The compositions of this invention may also be administered in the form of an implant, which allows slow release of the compositions as well as a slow controlled i.v. infusion. In a preferred embodiment, pyrazolo pyridine derivatives according to the invention are administered intravenously or subcutaneously.

This invention is further illustrated by the following examples that are not intended to limit the scope of the invention in any way.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Combination

According to one embodiment of the invention, the compounds according to the invention and pharmaceutical formulations thereof can be administered alone or in combination with a co-agent useful in the treatment of cancer, such as substances used in conventional chemotherapy directed against solid tumors and for control of establishment of metastases or substances used in hormonotherapy or any other molecule that act by triggering programmed cell death e.g. for example a co-agent selected from the category of drugs that stop the synthesis of pre DNA molecule building blocks such as methotrexate (Abitrexate®), fluorouracil (Adrucil®), hydroxyurea (Hydrea®), and mercaptopurine (Purinethol®), e.g. for example a co-agent selected from the category of drugs that directly damage the DNA in the nucleus of the cell such as cisplatin (Platinol®) and antibiotics—daunorubicin (Cerubidine®), doxorubicin (Adriamycin®), and etoposide (VePesid®), e.g. for example a co-agent selected from the category of drugs that effect the synthesis or breakdown of the mitotic spindles such as Vinblastine (Velban®), Vincristine (Oncovin®) and Pacitaxel (Taxol®).

According to another embodiment of the invention, the compounds according to the invention and pharmaceutical formulations thereof can be administered in combination with agents targeting cell-surface proteins such as gene transfer of cytokine receptor chain and receptor-targeted cytotoxin administration.

According to another embodiment of the invention, the compounds according to the invention and pharmaceutical formulations thereof can be administered in combination with radiation therapy.

The invention encompasses the administration of a compound according to the invention or of a pharmaceutical formulation thereof, wherein the compound according to the invention or the pharmaceutical formulation thereof is administered to an individual prior to, simultaneously or sequentially with other therapeutic regimens or co-agents useful in the treatment of cancers (e.g. multiple drug regimens), in a therapeutically effective amount. Compounds according to the invention or the pharmaceutical formulations thereof that are administered simultaneously with said co-agents can be administered in the same or different composition(s) and by the same or different route(s) of administration.

In another particular embodiment, the compounds and methods of the invention are contemplated for use in the treatment of cancers wherein the administration of a compound according to the invention is typically conducted during or after chemotherapy, hormonotherapy or radiotherapy.

In another particular embodiment, the compounds and methods of the invention are contemplated for use in the treatment of cancers wherein the administration of a compound according to the invention is typically conducted after a regimen of chemotherapy, hormonotherapy or radiotherapy at times where the tumor tissue will be responding to the toxic assault by inducing angiogenesis to recover by the provision of a blood supply and nutrients to the tumor tissue.

In another embodiment, the administration of a compound according to the invention is performed after surgery where solid tumors have been removed as a prophylaxis against metastases.

Patients

In an embodiment, patients according to the invention are patients suffering from a cardiovascular disorder or disease.

In another embodiment, patients according to the invention are patients suffering from a respiratory disorder or disease.

In another embodiment, patients according to the invention are patients suffering from a disease or disorder affecting the metabolism.

In another embodiment, patients according to the invention are patients suffering from a skin disorder.

In another embodiment, patients according to the invention are patients suffering from a bone disorder.

In another embodiment, patients according to the invention are patients suffering from a neuroinflammatory disorder and/or a neurodegenerative disorder.

In another embodiment, patients according to the invention are patients suffering from a kidney disease.

In another embodiment, patients according to the invention are patients suffering from a reproduction disorder.

In another embodiment, patients according to the invention are patients suffering from a disease or disorder affecting the eye and/or the lens and/or a condition affecting the inner ear.

In another embodiment, patients according to the invention are patients suffering from an inflammatory disorder or disease.

In another embodiment, patients according to the invention are patients suffering from a liver disease.

In another embodiment, patients according to the invention are patients suffering from pain, such as inflammatory pain.

In another embodiment, patients according to the invention are patients suffering from a cancer.

In another embodiment, patients according to the invention are suffering from angiogenesis or an angiogenesis-dependent condition.

In another embodiment, patients according to the invention are patients suffering from allergic disorders.

In another embodiment, patients according to the invention are patients suffering from traumatisms.

In another embodiment, patients according to the invention are patients suffering from septic, hemorrhagic and anaphylactic shock.

In another embodiment, patients according to the invention are patients suffering from a disease or disorders of the gastrointestinal system.

Use According to the Invention

In another embodiment, the invention provides a pyrazolo pyridine derivative according to Formula (I); as well as pharmaceutically acceptable salts and pharmaceutically active derivative thereof for use as a medicament.

In a further embodiment, the invention provides a pyrazolo pyridine derivative according to the invention wherein $G_1$ is H.

In a further embodiment, the invention provides a pyrazolo pyridine derivative according to the invention wherein $G_1$ is optionally substituted acyl.

In a further embodiment, the invention provides a pyrazolo pyridine derivative according to the invention wherein $G_2$ is —$CHR^1R^2$; $R^1$ and $R^2$ are as defined in the detailed description.

In a further embodiment, the invention provides a pyrazolo pyridine derivative according to the invention wherein $G_2$ is an optionally substituted saturated ring system.

In another further embodiment, the invention provides a pyrazolo pyridine derivative according to the invention wherein $G_2$ is —$CHR^1R^2$; $R^1$ is H; $R^2$ is as defined in the detailed description.

In another further embodiment, the invention provides a pyrazolo pyridine derivative according to the invention wherein $G_2$ is —$CHR^1R^2$; $R^1$ is optionally substituted $C_1$-$C_6$ alkyl; $R^2$ is as defined in the detailed description.

In another further embodiment, the invention provides a pyrazolo pyridine derivative according to the invention wherein $G_2$ is —$CHR^1R^2$; $R^1$ is optionally substituted aryl; $R^2$ is as defined in the detailed description.

In another further embodiment, the invention provides a pyrazolo pyridine derivative according to the invention wherein $G_2$ is —$CHR^1R^2$; $R^1$ is optionally substituted amino $C_1$-$C_6$ alkyl; $R^2$ is as defined in the detailed description.

In another further embodiment, the invention provides a pyrazolo pyridine derivative according to the invention wherein $G_2$ is —$CHR^1R^2$; $R^1$ is optionally substituted $C_2$-$C_6$-cycloalkyl; $R^2$ is as defined in the detailed description.

In another further embodiment, the invention provides a pyrazolo pyridine derivative according to the invention wherein $G_2$ is —$CHR^1R^2$; $R^1$ is optionally substituted heterocycloalkyl; $R^2$ is as defined in the detailed description.

In another further embodiment, the invention provides a pyrazolo pyridine derivative according to the invention wherein $G_2$ is —$CHR^1R^2$; $R^1$ is optionally substituted heterocycloalkyl $C_1$-$C_6$ alkyl; $R^2$ is as defined in the detailed description.

In another further embodiment, the invention provides a pyrazolo pyridine derivative according to the invention wherein $G_2$ is —$CHR^1R^2$; $R^1$ is optionally substituted alkoxy $C_1$-$C_6$ alkyl; $R^2$ is as defined in the detailed description.

In a further embodiment, the invention provides a pyrazolo pyridine derivative according to the invention wherein $G_2$ is —$CHR^1R^2$; $R^2$ is H; $R^2$ is as defined in the detailed description.

In a further embodiment, the invention provides a pyrazolo pyridine derivative according to the invention wherein $G_2$ is —$CHR^1R^2$; $R^1$ and $R^2$ are H.

In another further embodiment, the invention provides a pyrazolo pyridine derivative according to the invention wherein $G_2$ is —$CHR^1R^2$; —$CHR^1R^2$ form together an optionally substituted ring selected from an optionally substituted $C_3$-$C_8$-cycloalkyl and an optionally substituted heterocycloalkyl.

In another further embodiment, the invention provides a pyrazolo pyridine derivative according to the invention wherein $G_3$ is optionally substituted $C_1$-$C_6$ alkyl.

In another further embodiment, the invention provides a pyrazolo pyridine derivative according to the invention wherein $G_3$ is optionally substituted amino.

In another further embodiment, the invention provides a pyrazolo pyridine derivative according to the invention wherein $G_3$ is optionally substituted amino $C_1$-$C_6$ alkyl.

In another further embodiment, the invention provides a pyrazolo pyridine derivative according to the invention wherein $G_3$ is optionally substituted aminocarbonyl.

In another further embodiment, the invention provides a pyrazolo pyridine derivative according to the invention wherein $G_3$ is optionally substituted acyl.

In another further embodiment, the invention provides a pyrazolo pyridine derivative according to the invention wherein $G_3$ is optionally substituted alkoxy.

In another further embodiment, the invention provides a pyrazolo pyridine derivative according to the invention wherein $G_3$ is optionally substituted alkoxy $C_1$-$C_6$ alkyl.

In another further embodiment, the invention provides a pyrazolo pyridine derivative according to the invention wherein $G_3$ is optionally substituted aryl.

In another further embodiment, the invention provides a pyrazolo pyridine derivative according to the invention wherein $G_3$ is optionally substituted heteroaryl.

In another further embodiment, the invention provides a pyrazolo pyridine derivative according to the invention wherein $G_3$ is selected from optionally substituted heterocycloalkyl and $C_2$-$C_6$ cycloalkyl.

In another further embodiment, the invention provides a pyrazolo pyridine derivative according to the invention wherein $G_4$ is selected from optionally substituted $C_1$-$C_6$ alkyl; optionally substituted $C_2$-$C_6$ alkenyl and optionally substituted $C_2$-$C_6$ alkynyl.

In another further embodiment, the invention provides a pyrazolo pyridine derivative according to the invention wherein $G_4$ is optionally substituted acyl amino $C_1$-$C_6$ alkyl.

In another further embodiment, the invention provides a pyrazolo pyridine derivative according to the invention wherein $G_4$ is optionally substituted alkoxy $C_1$-$C_6$ alkyl.

In another further embodiment, the invention provides a pyrazolo pyridine derivative according to the invention wherein $G_4$ is selected optionally substituted aryl.

In another further embodiment, the invention provides a pyrazolo pyridine derivative according to the invention wherein $G_4$ is selected from optionally substituted optionally substituted aryl $C_1$-$C_6$ alkyl and substituted heteroaryl $C_1$-$C_6$ alkyl.

In another further embodiment, the invention provides a pyrazolo pyridine derivative according to the invention wherein G₄ is optionally substituted optionally substituted C₃-C₈-cycloalkyl C₁-C₆ alkyl and optionally substituted heterocycloalkyl C₁-C₆ alkyl.

In another further embodiment, the invention provides a pyrazolo pyridine derivative according to the invention wherein G₄ is optionally substituted acyl.

In another further embodiment, the invention provides a pyrazolo pyridine derivative according to the invention wherein G₄ is optionally substituted acyl amino.

In another further embodiment, the invention provides a pyrazolo pyridine derivative according to the invention wherein G₄ is optionally substituted acyl C₁-C₆ alkyl.

In another further embodiment, the invention provides a pyrazolo pyridine derivative according to the invention wherein G₅ is H.

In another embodiment, the invention provides a use of a pyrazolo pyridine derivative according to Formula (I) wherein G₁, G₂, G₃, G₄ and G₅ are as defined in the detailed description as well as pharmaceutically acceptable salts and pharmaceutically active derivative thereof for the preparation of a pharmaceutical composition for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, disorders of the gastrointestinal system, angiogenesis, angiogenesis-dependent conditions and other diseases and disorders associated with Nicotinamide adenine dinucleotide phosphate oxidase (NADPH Oxidase).

In another embodiment, the invention provides a pyrazolo pyridine derivative according to Formula (I) wherein G₁, G₂, G₃, G₄ and G₅ are as defined in the detailed description, as well as pharmaceutically acceptable salts and pharmaceutically active derivative thereof for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, disorders of the gastrointestinal system, angiogenesis, angiogenesis-dependent conditions and other diseases and disorders associated with Nicotinamide adenine dinucleotide phosphate oxidase (NADPH Oxidase).

Compounds of the present invention include in particular those selected from the following group:
2-benzyl-4-methyl-5-(pyridin-2-ylmethyl)-1H-pyrazolo[4,3-c]pyridine-3,6(2H,5H)-dione;
2-(4-chlorobenzyl)-4-methyl-5-(pyridin-2-ylmethyl)-1H-pyrazolo[4,3-c]pyridine-3,6(2H,5H)-dione;
2-benzyl-4-methyl-5-[3-(trifluoromethoxy)phenyl]-1H-pyrazolo[4,3-c]pyridine-3,6(2H,5H)-dione;
2,4-dimethyl-5-(pyridin-2-ylmethyl)-1H-pyrazolo[4,3-c]pyridine-3,6(2H,5H)-dione;
2,4,5-trimethyl-1H-pyrazolo[4,3-c]pyridine-3,6(2H,5H)-dione;
5-(furan-2-ylmethyl)-2,4-dimethyl-1H-pyrazolo[4,3-c]pyridine-3,6(2H,5H)-dione;
5-(4-chlorobenzyl)-2,4-dimethyl-1H-pyrazolo[4,3-c]pyridine-3,6(2H,5H)-dione;
4-butyl-5-(4-chlorobenzyl)-2-methyl-1H-pyrazolo[4,3-c]pyridine-3,6(2H,5H)-dione;
4-butyl-2-methyl-5-(pyridin-2-ylmethyl)-1H-pyrazolo[4,3-c]pyridine-3,6(2H,5H)-dione;
5-(4-chlorobenzyl)-4-methyl-2-(2-morpholin-4-ylethyl)-1H-pyrazolo[4,3-c]pyridine-3,6(2H,5H)-dione;
2-benzyl-4-butyl-5-(3,5-dimethoxybenzyl)-1H-pyrazolo[4,3-c]pyridine-3,6(2H,5H)-dione;
2-benzyl-4-butyl-5-(pyridin-2-ylmethyl)-1H-pyrazolo[4,3-c]pyridine-3,6(2H,5H)-dione;
2-cyclohexyl-4-methyl-5-[2-(morpholin-4-ylmethyl)benzyl]-1H-pyrazolo[4,3-c]pyridine-3,6(2H,5H)-dione;
2,4-dimethyl-5-(2-pyridin-2-ylethyl)-1H-pyrazolo[4,3-c]pyridine-3,6(2H,5H)-dione;
2-(2-methoxyethyl)-4-methyl-5-(2-pyridin-2-ylethyl)-1H-pyrazolo[4,3-c]pyridine-3,6(2H,5H)-dione; and
2,4-dimethyl-5-(2-morpholin-4-ylethyl)-1H-pyrazolo[4,3-c]pyridine-3,6(2H,5H)-dione.

Compounds of the present invention further include in particular those selected from the following group:
5-(2-methoxyethyl)-4-methyl-2-(2-phenylethyl)-1H-pyrazolo[4,3-c]pyridine-3,6(2H,5H)-dione;
2-(2-methoxyethyl)-4-methyl-5-[2-(morpholin-4-ylmethyl)benzyl]-1H-pyrazolo[4,3-c]pyridine-3,6(2H,5H)-dione;
N-{3-[2-(2-methoxyethyl)-4-methyl-3,6-dioxo-1,2,3,6-tetrahydro-5H-pyrazolo[4,3-c]pyridin-5-yl]phenyl}acetamide;
2-(2-methoxyethyl)-4-methyl-5-(2-morpholin-4-yl-2-oxoethyl)-1H-pyrazolo[4,3-c]pyridine-3,6(2H,5H)-dione;
2-benzyl-4-(3-methoxybenzyl)-5-(pyridin-2-ylmethyl)-1H-pyrazolo[4,3-c]pyridine-3,6 (2H,5H)-dione;
2-benzyl-4-(3-methoxybenzyl)-5-(2-methoxyethyl)-1H-pyrazolo[4,3-c]pyridine-3,6 (2H,5H)-dione;
2-(2,5-dichlorobenzyl)-5-(2-methoxyethyl)-4-methyl-1H-pyrazolo[4,3-c]pyridine-3,6 (2H,5H)-dione;
2-[2-(4-chlorophenoxy)ethyl]-4-methyl-5-(pyridin-2-ylmethyl)-1H-pyrazolo[4,3-c]pyridine-3,6(2H,5H)-dione;
2-(2,5-dichlorobenzyl)-4-methyl-5-(2-morpholin-4-ylethyl)-1H-pyrazolo[4,3-c]pyridine-3,6 (2H,5H)-dione;
2-(2,5-dichlorobenzyl)-4-methyl-5-[2-(morpholin-4-ylmethyl)benzyl]-1H-pyrazolo[4,3-c]pyridine-3,6(2H,5H)-dione;
5-(3,5-dimethoxybenzyl)-2-(2-methoxyethyl)-4-methyl-1H-pyrazolo[4,3-c]pyridine-3,6 (2H,5H)-dione;
N-(3-{[4-methyl-3,6-dioxo-2-(2-phenylethyl)-1,2,3,6-tetrahydro-5H-pyrazolo[4,3-c]pyridin-5-yl]methyl}phenyl)acetamide;
4-methyl-5-(2-morpholin-4-ylethyl)-2-(2-phenylethyl)-1H-pyrazolo[4,3-c]pyridine-3,6(2H,5H)-dione;
4-methyl-5-[2-(morpholin-4-ylmethyl)benzyl]-2-(2-phenylethyl)-1H-pyrazolo[4,3-c]pyridine-3,6(2H,5H)-dione;
2-(2-methoxyethyl)-4-methyl-5-(pyridin-2-ylmethyl)-1H-pyrazolo[4,3-c]pyridine-3,6 (2H,5H)-dione;
N-[2-(2-benzyl-4-methyl-3,6-dioxo-1,2,3,6-tetrahydro-5H-pyrazolo[4,3-c]pyridin-5-yl)ethyl]-4-fluorobenzamide;
N-[3-(2-benzyl-4-methyl-3,6-dioxo-1,2,3,6-tetrahydro-5H-pyrazolo[4,3-c]pyridin-5-yl)phenyl]acetamide;
N-(3-{[2-(2-chloro-4-fluorobenzyl)-4-methyl-3,6-dioxo-1,2,3,6-tetrahydro-5H-pyrazolo[4,3-c]pyridin-5-yl]methyl}phenyl)acetamide;
5-[2-(4-benzylpiperazin-1-yl)-2-oxoethyl]-2-(2-methoxyethyl)-4-methyl-1H-pyrazolo[4,3-c]pyridine-3,6(2H,5H)-dione;
2-(2,5-dichlorobenzyl)-4-methyl-5-(pyridin-2-ylmethyl)-1H-pyrazolo[4,3-c]pyridine-3,6 (2H,5H)-dione;

2-(2-chloro-4-fluorobenzyl)-4-methyl-5-[2-(morpholin-4-ylmethyl)benzyl]-1H-pyrazolo[4,3-c]pyridine-3,6(2H,5H)-dione;

2-(2,5-dichlorobenzyl)-4-methyl-5-(2-morpholin-4-yl-2-oxoethyl)-1H-pyrazolo[4,3-c]pyridine-3,6(2H,5H)-dione;

4-methyl-2-(2-phenylethyl)-5-(pyridin-2-ylmethyl)-1H-pyrazolo[4,3-c]pyridine-3,6 (2H,5H)-dione;

2-(2-chloro-4-fluorobenzyl)-4-methyl-5-(pyridin-2-ylmethyl)-1H-pyrazolo[4,3-c]pyridine-3,6(2H,5H)-dione;

4-fluoro-N-{2-[2-(2-methoxyethyl)-4-methyl-3,6-dioxo-1,2,3,6-tetrahydro-5H-pyrazolo[4,3-c]pyridin-5-yl]ethyl}benzamide;

5-[2-(4-benzylpiperazin-1-yl)-2-oxoethyl]-2-(2-chloro-4-fluorobenzyl)-4-methyl-1H-pyrazolo[4,3-c]pyridine-3,6 (2H,5H)-dione;

5-benzyl-4-methyl-2-(1-methylpiperidin-4-yl)-1H-pyrazolo[4,3-c]pyridine-3,6(2H,5H)-dione;

4-methyl-2-(2-methylpropyl)-5-(pyridin-3-ylmethyl)-1H-pyrazolo[4,3-c]pyridine-3,6 (2H,5H)-dione;

4-methyl-2-(2-methylpropyl)-5-(2-morpholin-4-ylethyl)-1H-pyrazolo[4,3-c]pyridine-3,6 (2H,5H)-dione;

5-(2,5-dichlorobenzyl)-4-methyl-2-(2-methylpropyl)-1H-pyrazolo[4,3-c]pyridine-3,6 (2H,5H)-dione;

5-(2,4-dichlorobenzyl)-4-methyl-2-(2-methylpropyl)-1H-pyrazolo[4,3-c]pyridine-3,6 (2H,5H)-dione;

5-(2,3-dihydro-1H-inden-1-yl)-4-methyl-2-(2-methylpropyl)-1H-pyrazolo[4,3-c]pyridine-3,6(2H,5H)-dione;

4-(3-chlorophenyl)-5-(2-morpholin-4-ylethyl)-2-(2-phenylethyl)-1H-pyrazolo[4,3-c]pyridine-3,6(2H,5H)-dione;

2-benzyl-4-(3-chlorophenyl)-5-(2-methoxyethyl)-1H-pyrazolo[4,3-c]pyridine-3,6(2H,5H)-dione;

5-(4-chlorobenzyl)-4-[(4-fluorophenoxy)methyl]-2-(2-morpholin-4-ylethyl)-1H-pyrazolo[4,3-c]pyridine-3,6(2H,5H)-dione;

4-[(4-fluorophenoxy)methyl]-5-(2-methoxyethyl)-2-(2-morpholin-4-ylethyl)-1H-pyrazolo[4,3-c]pyridine-3,6 (2H,5H)-dione;

5-(4-chlorobenzyl)-4-(3-chlorophenyl)-2-(2-morpholin-4-ylethyl)-1H-pyrazolo[4,3-c]pyridine-3,6(2H,5H)-dione;

4-(3-chlorophenyl)-2-(2-morpholin-4-ylethyl)-5-(pyridin-2-ylmethyl)-1H-pyrazolo[4,3-c]pyridine-3,6(2H,5H)-dione;

5-(4-chlorobenzyl)-4-(4-chlorophenyl)-2-(2-morpholin-4-ylethyl)-1H-pyrazolo[4,3-c]pyridine-3,6(2H,5H)-dione;

4-(4-chlorophenyl)-5-(4-methoxybenzyl)-2-(2-morpholin-4-ylethyl)-1H-pyrazolo[4,3-c]pyridine-3,6(2H,5H)-dione;

4-(4-chlorophenyl)-5-(3-methoxybenzyl)-2-(2-morpholin-4-ylethyl)-1H-pyrazolo[4,3-c]pyridine-3,6(2H,5H)-dione;

4-(4-chlorophenyl)-2,5-bis(2-methoxyethyl)-1H-pyrazolo[4,3-c]pyridine-3,6(2H,5H)-dione;

5-(4-chlorobenzyl)-4-(4-chlorophenyl)-2-(2-methoxyethyl)-1H-pyrazolo[4,3-c]pyridine-3,6 (2H,5H)-dione;

4-(4-chlorophenyl)-5-(2-methoxyethyl)-2-methyl-1H-pyrazolo[4,3-c]pyridine-3,6(2H,5H)-dione;

4-[(4-fluorophenoxy)methyl]-5-(4-methoxybenzyl)-2-(2-morpholin-4-ylethyl)-1H-pyrazolo[4,3-c]pyridine-3,6 (2H,5H)-dione;

4-[(4-fluorophenoxy)methyl]-2-(2-morpholin-4-ylethyl)-5-(pyridin-2-ylmethyl)-1H-pyrazolo[4,3-c]pyridine-3,6 (2H,5H)-dione;

4-(4-chlorophenyl)-5-(2-morpholin-4-ylethyl)-2-(2-phenylethyl)-1H-pyrazolo[4,3-c]pyridine-3,6(2H,5H)-dione;

4-(4-chlorophenyl)-5-(3-methoxybenzyl)-2-(2-methoxyethyl)-1H-pyrazolo[4,3-c]pyridine-3,6(2H,5H)-dione;

4-(4-chlorophenyl)-2-(2-methoxyethyl)-5-[2-(morpholin-4-ylmethyl)benzyl]-1H-pyrazolo[4,3-c]pyridine-3,6(2H,5H)-dione;

4-(4-chlorophenyl)-2-(2-methoxyethyl)-5-(pyridin-2-ylmethyl)-1H-pyrazolo[4,3-c]pyridine-3,6(2H,5H)-dione;

4-(4-chlorophenyl)-5-(3-ethoxypropyl)-2-(2-morpholin-4-ylethyl)-1H-pyrazolo[4,3-c]pyridine-3,6(2H,5H)-dione;

5-(2-methoxyethyl)-4-methyl-2-(2-morpholin-4-ylethyl)-1H-pyrazolo[4,3-c]pyridine-3,6 (2H,5H)-dione;

4-(4-chlorophenyl)-5-(2-methoxyethyl)-2-(2-morpholin-4-ylethyl)-1H-pyrazolo[4,3-c]pyridine-3,6(2H,5H)-dione;

4-(3,4-dichlorophenyl)-2-(2-methoxyethyl)-5-(pyridin-2-ylmethyl)-1H-pyrazolo[4,3-c]pyridine-3,6(2H,5H)-dione;

4-(3,4-dichlorophenyl)-5-(2-methoxyethyl)-2-methyl-1H-pyrazolo[4,3-c]pyridine-3,6 (2H,5H)-dione;

4-(4-chlorophenyl)-5-methyl-2-(2-morpholin-4-ylethyl)-1H-pyrazolo[4,3-c]pyridine-3,6 (2H,5H)-dione;

5-methyl-2-(2-morpholin-4-ylethyl)-4-(3-phenoxypropyl)-1H-pyrazolo[4,3-c]pyridine-3,6 (2H,5H)-dione;

5-(2-methoxyethyl)-2-(2-morpholin-4-ylethyl)-4-(3-phenoxypropyl)-1H-pyrazolo[4,3-c]pyridine-3,6(2H,5H)-dione;

4-[(4-fluorophenoxy)methyl]-2-(2-methoxyethyl)-5-(pyridin-2-ylmethyl)-1H-pyrazolo[4,3-c]pyridine-3,6(2H,5H)-dione;

4-[(4-chlorophenoxy)methyl]-5-(2-methoxyethyl)-2-(2-morpholin-4-ylethyl)-1H-pyrazolo[4,3-c]pyridine-3,6 (2H,5H)-dione;

4-(4-chlorophenyl)-2-(2-methoxyethyl)-5-methyl-1H-pyrazolo[4,3-c]pyridine-3,6(2H,5H)-dione;

4-(4-chlorophenyl)-2-(2-morpholin-4-ylethyl)-5-(pyridin-2-ylmethyl)-1H-pyrazolo[4,3-c]pyridine-3,6(2H,5H)-dione;

4-[(4-fluorophenoxy)methyl]-5-(3-methoxybenzyl)-2-(2-methoxyethyl)-1H-pyrazolo[4,3-c]pyridine-3,6(2H,5H)-dione;

4-methyl-2-(2-morpholin-4-ylethyl)-5-(pyridin-2-ylmethyl)-1H-pyrazolo[4,3-c]pyridine-3,6(2H,5H)-dione;

4-(4-chlorophenyl)-5-methyl-2-(1-methylpiperidin-4-yl)-1H-pyrazolo[4,3-c]pyridine-3,6 (2H,5H)-dione;

4-(4-chlorophenyl)-2-[2-(dimethylamino)ethyl]-5-(pyridin-2-ylmethyl)-1H-pyrazolo[4,3-c]pyridine-3,6(2H,5H)-dione;

5-(3-methoxybenzyl)-4-methyl-2-(2-morpholin-4-ylethyl)-1H-pyrazolo[4,3-c]pyridine-3,6 (2H,5H)-dione;

2-(2-morpholin-4-ylethyl)-4-(3-phenoxypropyl)-5-(pyridin-2-ylmethyl)-1H-pyrazolo[4,3-c]pyridine-3,6(2H,5H)-dione;

4-(3-chlorophenyl)-5-(3-ethoxypropyl)-2-(2-morpholin-4-ylethyl)-1H-pyrazolo[4,3-c]pyridine-3,6(2H,5H)-dione;

4-[(4-fluorophenoxy)methyl]-5-methyl-2-(2-morpholin-4-ylethyl)-1H-pyrazolo[4,3-c]pyridine-3,6(2H,5H)-dione;

4-[(4-chlorophenoxy)methyl]-5-(3-ethoxypropyl)-2-(2-morpholin-4-ylethyl)-1H-pyrazolo[4,3-c]pyridine-3,6 (2H,5H)-dione;

4-[(benzyloxy)methyl]-5-(3-methoxybenzyl)-2-(2-morpholin-4-ylethyl)-1H-pyrazolo[4,3-c]pyridine-3,6(2H,5H)-dione;

4-[(benzyloxy)methyl]-5-(3-ethoxypropyl)-2-(2-morpholin-4-ylethyl)-1H-pyrazolo[4,3-c]pyridine-3,6(2H,5H)-dione;

5-(3-ethoxypropyl)-4-[(4-fluorophenoxy)methyl]-2-(2-morpholin-4-ylethyl)-1H-pyrazolo[4,3-c]pyridine-3,6(2H,5H)-dione;

4-[(4-chlorophenoxy)methyl]-2-(2-morpholin-4-ylethyl)-5-(pyridin-2-ylmethyl)-1H-pyrazolo[4,3-c]pyridine-3,6 (2H,5H)-dione;

4-(4-chlorophenyl)-2-(2-morpholin-4-ylethyl)-5-(2-pyridin-2-ylethyl)-1H-pyrazolo[4,3-c]pyridine-3,6(2H,5H)-dione;

4-[(4-fluorophenoxy)methyl]-2-(2-morpholin-4-ylethyl)-5-(2-pyridin-2-ylethyl)-1H-pyrazolo[4,3-c]pyridine-3,6(2H,5H)-dione;

2,5-bis(2-methoxyethyl)-4-(3-phenoxypropyl)-1H-pyrazolo[4,3-c]pyridine-3,6(2H,5H)-dione;

4-[(4-chlorophenoxy)methyl]-5-(3-methoxybenzyl)-2-(2-morpholin-4-ylethyl)-1H-pyrazolo[4,3-c]pyridine-3,6(2H,5H)-dione;

4-(3,5-dichlorophenyl)-5-(2-methoxyethyl)-2-methyl-1H-pyrazolo[4,3-c]pyridine-3,6 (2H,5H)-dione;

5-[(4-benzylmorpholin-2-yl)methyl]-4-(4-chlorophenyl)-2-methyl-1H-pyrazolo[4,3-c]pyridine-3,6(2H,5H)-dione;

5-[(1-acetylpiperidin-4-yl)methyl]-4-(4-chlorophenyl)-2-methyl-1H-pyrazolo[4,3-c]pyridine-3,6(2H,5H)-dione;

tert-butyl 4-{[4-(4-chloro phenyl)-2-methyl-3,6-dioxo-1,2,3,6-tetrahydro-5H-pyrazolo[4,3-c]pyridin-5-yl]methyl}piperidine-1-carboxylate; and 4-(4-chlorophenyl)-2-methyl-5-[(5-oxopyrrolidin-3-yl)methyl]-1H-pyrazolo[4,3-c]pyridine-3,6(2H,5H)-dione.

In another embodiment, the invention provides a method for treating a patient suffering from a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers allergic disorders, traumatisms, septic, hemorrhagic and anaphylactic shock, disorders of the gastrointestinal system, angiogenesis, angiogenesis-dependent conditions and other diseases and disorders associated with Nicotinamide adenine dinucleotide phosphate oxidase (NADPH Oxidase). The method comprises administering a compound according to Formula (I) in a patient in need thereof.

In another embodiment, the invention provides a method for inhibiting angiogenesis in a patient in need thereof, wherein the method comprises administering an angiogenesis inhibiting dose of a compound of Formula (I) in a patient in need thereof.

In another embodiment, the invention provides a method of inhibiting tumor neovascularization by inhibiting tumor angiogenesis according to the present methods. Similarly, the invention provides a method for inhibiting tumor growth by practicing the angiogenesis-inhibiting methods.

In a particular embodiment, the compounds and methods of the invention are contemplated for use in treatment of a tumor tissue of a patient with a tumor, solid tumor, a metastasis, a cancer, a melanoma, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present compounds and methods include, but are not limited to, tumors of the skin, melanoma, lung, pancreas, breast, colon, laryngeal, ovarian, prostate, colorectal, head, neck, testicular, lymphoid, marrow, bone, sarcoma, renal, sweat gland, and the like tissues. Further examples of cancers treated are glioblastomas.

In another particular embodiment, the compounds and methods of the invention are contemplated for use in treatment of an inflamed tissue and the angiogenesis to be inhibited is inflamed tissue angiogenesis where there is neovascularization of inflamed tissue. In this case, the compound and method according to the invention contemplate the inhibition of angiogenesis in arthritic tissues, such as in a patient with chronic articular rheumatism, in immune or non-immune inflamed tissues, in psoriatic tissue and the like.

In embodiments, the invention contemplates inhibition of angiogenesis in a tissue. The extent of angiogenesis in a tissue, and therefore the extent of inhibition achieved by the present methods, can be evaluated by a variety of methods, such as are described herein.

In another embodiment, the invention provides a pharmaceutical composition containing at least one derivative pyrazolo pyridine according to Formula (I) and a pharmaceutically acceptable carrier, diluent or excipient thereof.

The compounds of invention have been named according to the IUPAC standards used in the program ACD/Name (product version 10.01).

Compounds according to the present invention comprise a compound according to Formula (I), its tautomers, its geometrical isomers, its optically active forms as enantiomers, diastereomers and its racemate forms, as well as pharmaceutically acceptable salts thereof. The derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention having been described, the following examples are presented by way of illustration, and not limitation.

Synthesis of Compounds of the Invention:

The novel derivatives according to Formula (I) can be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. The general synthetic approach for obtaining compounds of Formula (I) is depicted in Scheme 1 below.

i.e. of Formula (I) wherein $G_1$ is H, are isolated after cyclisation of intermediate compounds of Formula (VIII), preferably in protic solvents in presence of base such as sodium metha- Scheme 1

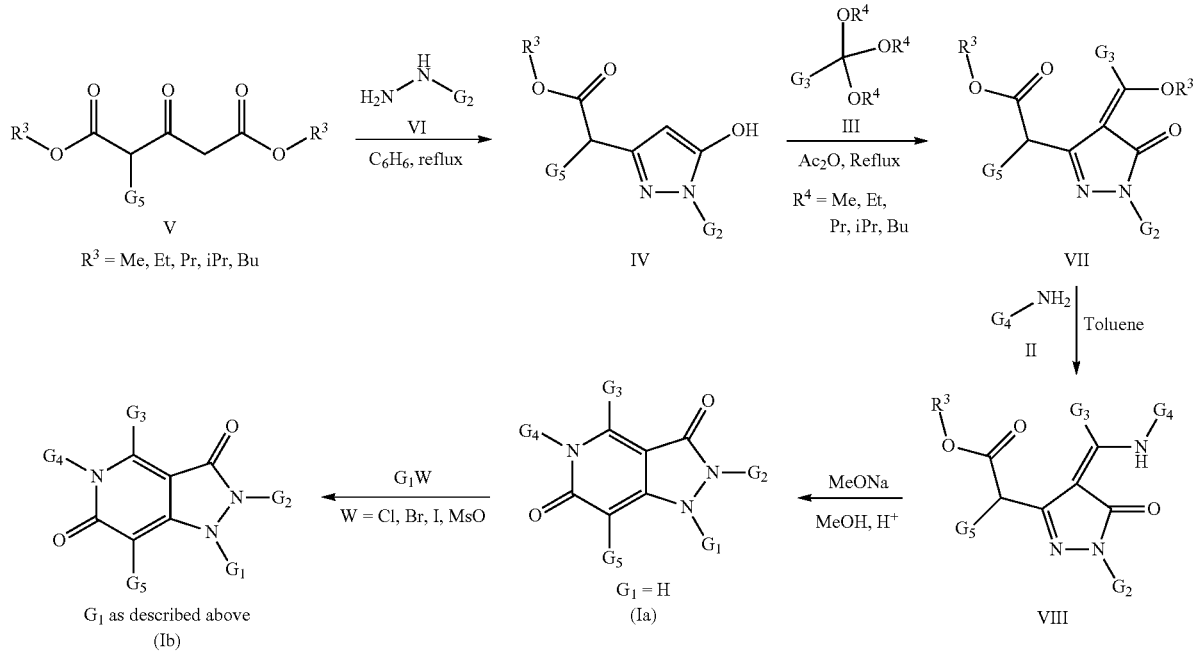

Pyrazolo pyridine derivatives according to Formula (I), whereby the substituents $G_1$, $G_2$, $G_3$, $G_4$ and $G_5$ are as above defined, may be prepared in three chemical steps, from custom made or commercially available substituted hydrazine derivatives according to Formula (VI), acetone dicarboxylate derivatives according to Formula (V), primary amine derivatives according to Formula (II) and trialkyl ortho ester derivatives according to Formula (III), following the synthetic protocol as outlined in Scheme 1 above. In a more specific method, a hydrazine derivative according to Formula (VI) wherein $G_2$ is defined as above is reacted with an acetone dicarboxylate derivative according to Formula (V) wherein $G_5$ and $R^3$ are defined as above, in neutral and under refluxing conditions in a suitable solvent like benzene, toluene or other unreactive solvents over time depending of the intrinsic reactivity of compounds according to Formula (VI) to give the corresponding 4-substituted 2-hydroxyl pyrazole derivatives according to Formula (IV). The intermediate compounds according to Formula (IV) are further reacted with trialkyl ortho ester derivatives according to Formula (III) wherein $G_3$ and $R^4$ are defined as above, to allow formation of an intermediate of Formula (VII) in presence of acetic acid and under refluxing conditions. Intermediate compounds of Formula (VII) are further treated with primary amine derivatives according to Formula (II) wherein $G_4$ is defined as above, in solvents such as toluene or benzene under refluxing conditions, to obtain the intermediate compounds of Formula (VIII). The pyrazolo derivatives according to Formula (Ia), nolate, sodium isopropanolate or the like, using standard refluxing conditions well known to the person skilled in the art as shown in Scheme 1.

This reaction may be performed in solvents like methanol, ethanol, isopropanol or other unreactive solvents at room temperature over time depending of the intrinsic reactivity of compounds according to Formula (VIII), but usually requires traditional thermal heating or microwave methods, using standard conditions well known to the person skilled in the art as shown in Scheme 1, above. In a subsequent step, the pyrazolo pyridine derivatives of Formula (Ia) were treated with an alkylating agent such as alkyl chlorides, bromides, iodides or mesylates, wherein $G_1$ is defined as above, in presence of a suitable base, e.g. Triethylamine, sodium hydride or potassium carbonate as a base in a suitable solvent, e.g. N,N-dimethylformamide or tetrahydrofuran, by traditional thermic method or using microwave technology. Alternatively, the pyrazolo pyridine derivatives of Formula (Ia) were treated with anhydrides, acyl chlorides, or carboxylic acids in presence of a coupling reagents, wherein $G_1$ is defined as above, in presence of a suitable base, e.g. Triethylamine, sodium acetate in a suitable solvent, e.g. N,N-dimethylformamide or tetrahydrofuran, dichloromethane by traditional thermic method or using microwave technology. Following this process, the pyrazolo pyridine derivatives according to Formula (Ib) are isolated, using standard conditions well known to the person skilled in the art as shown in the Scheme 1.

Scheme 2

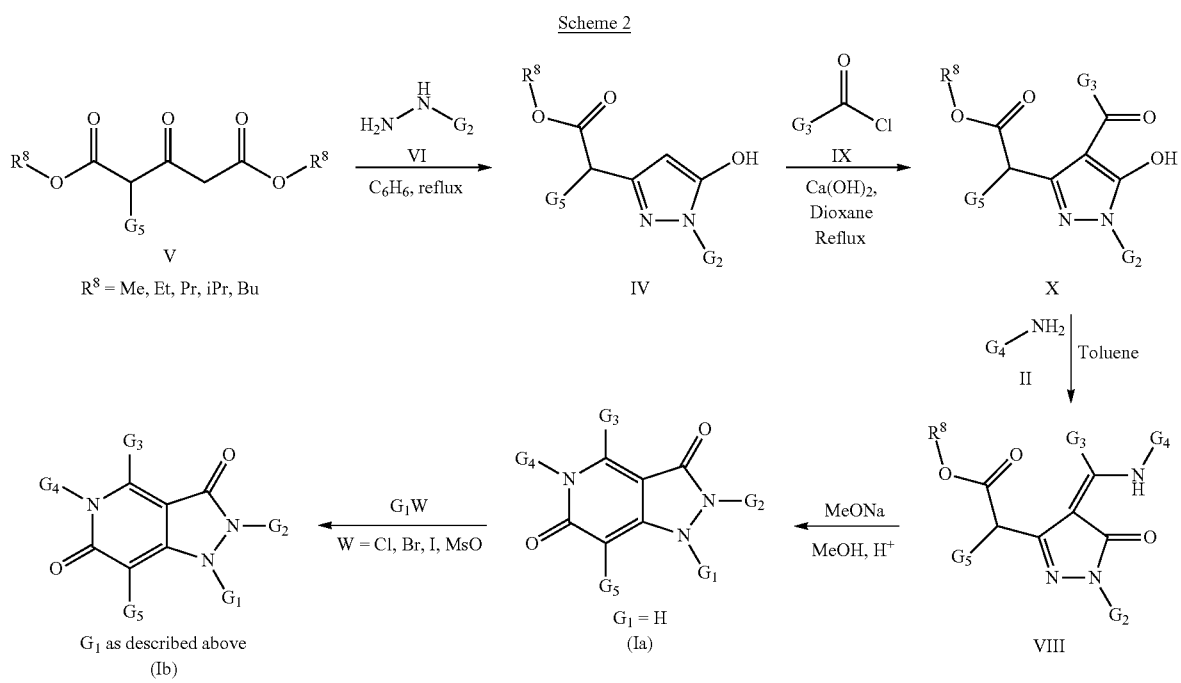

Pyrazolo pyridine derivatives according to Formula (I), whereby the substituents $G_1$, $G_2$, $G_3$, $G_4$ and $G_5$ are as above defined, may be prepared in four to five chemical steps, from custom made or commercially available substituted hydrazine derivatives according to Formula (VI), acetone dicarboxylate derivatives according to Formula (V), primary amine derivatives according to Formula (II) and acyl chloride derivatives according to Formula (IX), following the synthetic protocol outlined in Scheme 2 above. In a more specific method, a hydrazine derivative according to Formula (VI) wherein $G_2$ is defined above is reacted with an acetone dicarboxylate derivative according to Formula (V) wherein $G_5$ and $R^8$ are defined as above, in neutral and under refluxing conditions in a suitable solvents like benzene, toluene or other unreactive solvents over time depending of the intrinsic reactivity of compounds according to Formula (VI) to give the corresponding 4-substituted 2-hydroxyl pyrazole derivatives according to Formula (IV). The intermediate compounds according to Formula (IV) are further reacted with acyl chloride derivatives according to Formula (IX) wherein $G_3$ is defined as above, to allow formation of an intermediate of Formula (X) in presence of calcium hydroxide and under refluxing conditions. Intermediate compounds of Formula (X) are further treated with primary amine derivatives according to Formula (II) wherein $G_4$ is defined as above, in solvents such as toluene or benzene under refluxing conditions, to obtain the intermediate compounds of Formula (VIII). The pyrazolo derivatives according to Formula (Ia), i.e. of Formula (I) wherein $G_1$ is H, are isolated after cyclisation of intermediate compounds of Formula (VIII), preferably in protic solvents in presence of base such as sodium methanolate, sodium isopropanolate or the like, using standard refluxing conditions well known to the person skilled in the art as shown in Scheme 2.

In a subsequent step, the pyrazolo pyridine derivatives of Formula (Ia) were treated with an alkylating agent such as alkyl chlorides, bromides, iodides or mesylates, wherein $G_1$ is defined as above, in presence of a suitable base, e.g. triethylamine, sodium hydride or potassium carbonate as a base in a suitable solvent, e.g. N,N-dimethylformamide or tetrahydrofuran, by traditional thermic method or using microwave technology. Alternatively, the pyrazolo pyridine derivatives of Formula (Ia) were treated with anhydrides, acyl chlorides, or carboxylic acids in presence of a coupling reagents, wherein $G_1$ is defined as above, in presence of a suitable base, e.g. Triethylamine, sodium acetate in a suitable solvent, e.g. N,N-dimethylformamide or tetrahydrofuran, dichloromethane by traditional thermic method or using microwave technology. Following this process the pyrazolo pyridine derivatives according to Formula (Ib) are isolated, using standard conditions well known to the person skilled in the art as shown in Scheme 2.

These reactions may be performed in solvents like methanol, ethanol, isopropanol or other unreactive solvents at room temperature over time depending of the intrinsic reactivity of compounds according to Formula (VIII), but usually requires traditional thermal heating or microwave methods, using standard conditions well known to the person skilled in the art as shown in Schemes 1 or 2, above.

The Following Abbreviations Refer Respectively to the Definitions Below:

Å (Angström), $Ac_2O$ (Acetic anhydride), eq. (equivalent), min (minute), h (hour), g (gram), MHz (Megahertz), mL (milliliter), mm (millimeter), mmol (millimole), mM (millimolar), ng (nanogram), nm (nanometer), rt (room temperature), BLM (Bleomycine), BSA (Bovine serum albumin), DCF (2,7-dichlorodihydrofluorescein), DCM (dichloromethane), DIPEA (di-isopropyl ethylamine), DMSO (Dimethyl Sulfoxide), DMF (N,N-Dimethylformamide), DAPI (4,6 Diamidino-2-phenylindole), DPI (Diphenyl-iodonium), cHex (Cyclohexane), EDTA (ethylenediaminetetraacetic acid), EGF (Epidermal Growth Factor), EtOAc (Ethyl acetate), FC (Flash Chromatography on silica gel), HBSS (Hank's Buffered Salt Solution), HPLC (High performance liquid chromatography), $H_2DCF$-DA (2',7'-dichlorodihydrofluorescein diacetate), MEM (2-methoxyethoxymethyl), MS (Mass Spectrometry), NADPH (Nicotinamide adenine dinucleotide diphosphate reduced form), NBT (Nitroblue tetrazolium), NMR (Nuclear magnetic resonance), PBS (Phosphate Buffered Saline), PetEther (Petroleum ether), TEA (Triethyl amine), TFA (Trifluoroacetic acid), TGF-(Tumor Growth Factor beta), THF (Tetrahydrofuran), tBuOK (Potassium tert-butoxide), ROS (Reactive oxygen species), SOD (Superoxide dismutase), SPA (Scintillation proximity assay), TLC (Thin layer chromatography), UV (Ultraviolet).

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art. For all the protection and deprotection methods, see Philip J. Kocienski, in *"Protecting Groups", Georg Thieme Verlag Stuttgart,* 2005 and Theodora W. Greene and Peter G. M. Wuts in *"Protective Groups in Organic Synthesis", Wiley Interscience, 4th Edition* 2006.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not to be viewed as limiting the scope of the invention.

The HPLC, NMR and MS data provided in the examples described below are obtained as followed: HPLC: column Waters Symmetry C8 50×4.6 mm, Conditions: MeCN/$H_2O$, 5 to 100% (8 min), max plot 230-400 nm; Mass spectra: PE-SCIEX API 150 EX (APCI and ESI), LC/MS spectra: Waters ZMD (ES); $^1$H-NMR: Bruker DPX-300 MHz.

The preparative HPLC purifications are performed with HPLC Waters Prep LC 4000 System equipped with columns Prep Nova-Pak® HR C18 6 µm 60 Å, 40×30 mm (up to 100 mg) or with XTerra® Prep MS C8, 10 µm, 50×300 mm (up to 1 g). All the purifications are performed with a gradient of MeCN/$H_2O$ 0.09% TFA; UV detection at 254 nm and 220 nm; flow 20 mL/min (up to 50 mg). TLC Analysis is performed on Merck Precoated 60 $F_{254}$ plates. Purifications by flash chromatography are performed on $SiO_2$ support, using cyclohexane/EtOAc or DCM/MeOH mixtures as eluents.

Example 1

Formation of 2-Benzyl-4-Methyl-5-(Pyridin-2-Ylmethyl)-1H-Pyrazolo[4,3-c]Pyridine-3,6(2H,5H)-Dione (1)(Compound Ia, Scheme 1)

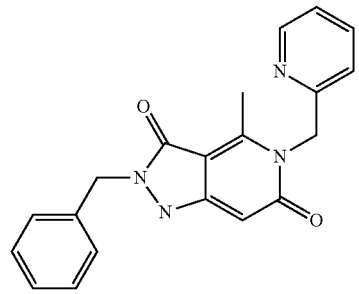 [SMILES: Cc1c2c(=O)n(Cc3ccccc3)[nH]c2cc(=O)n1Cc1ccccn1]

a) methyl(1-benzyl-5-hydroxy-1H-pyrazol-3-yl)acetate (Compound of Formula (IV), Scheme 1)

To a suspension of benzylamine dihydrochloride (1.000 g, 5.126 mmol, 1 equiv.) in anhydrous toluene (25 ml) were added successively diisopropylethylamine (1.32 ml, 10.252 mmol, 2 equiv) and dimethyl 3-oxopentanedioate (0.893 g, 5.126 mmol, 1 equiv.). The resulting mixture was heated at reflux for 18 h before being concentrated in vacuo. The resulting brown oil was purified by flash chromatography over $SiO_2$ ($CH_2Cl_2$:MeOH, 97:3). 0.810 g of pure methyl(1-benzyl-5-hydroxy-1H-pyrazol-3-yl)acetate was obtained as a white solid. Yield 64%. MS (ESI$^+$): 247.1; MS (ESI$^-$): 245.1.

b) methyl[(4E)-1-benzyl-4-(1-ethoxyethylidene)-5-oxo-4,5-dihydro-1H-pyrazol-3-yl]acetate (Compound of Formula (VII), Scheme 1)

The mixture of the above obtained methyl(1-benzyl-5-hydroxy-1H-pyrazol-3-yl)acetate (Compound of Formula (IV), 0.215 g, 0.873 mmol, 1 equiv.), glacial acetic acid (5 µl, 0.1 equiv.) and MeC(OEt)$_3$ (5.5 ml, 5.48 mmol, 6.3 equiv.) was heated at 75° C. for 1 h15. The resulting orange solution was concentrated in vacuo to afford an orange syrup that was washed with cyclohexane and then dried in vacuo. Due to its relative instability, no further purification of methyl[(4E)-1-benzyl-4-(1-ethoxyethylidene)-5-oxo-4,5-dihydro-1H-pyrazol-3-yl]acetate was conducted (0.276 g, quantitative yield). MS (ESI$^+$): 317.1.

c) methyl[(4E)-1-benzyl-5-oxo-4-{1-[(pyridin-2-ylmethyl)amino]ethylidene}-4,5-dihydro-1H-pyrazol-3-yl]acetate (Compound of Formula (VIII), Scheme 1)

The mixture of the above obtained methyl[(4E)-1-benzyl-4-(1-ethoxyethylidene)-5-oxo-4,5-dihydro-1H-pyrazol-3-yl]acetate (Compound of Formula (VII), 0.276 g, 0.873 mmol, 1 equiv.) and 1-pyridin-2-ylmethanamine (0.061 mL, 0.873 mmol, 1 equiv.) was stirred at room temperature in toluene (8.0 ml) for 15 min. The solvent was removed in vacuo. The resulting residue was dissolved in a minimum of $CH_2Cl_2$ and added dropwise to a stirred solution of 150 ml of cyclohexane resulting in the formation of a pale yellow precipitate that was filtered off. This precipitate was proved to be the pure methyl[(4E)-1-benzyl-5-oxo-4-{1-[(pyridin-2-ylmethyl)amino]ethylidene}-4,5-dihydro-1H-pyrazol-3-yl]acetate (0.278 g). Yield 84%. MS (ESI$^+$): 379.2.

d) 2-benzyl-4-methyl-5-(pyridin-2-ylmethyl)-1H-pyrazolo[4,3-c]pyridine-3,6(2H,5H)-dione (Compound of Formula (Ia), Scheme 1)

An isopropanolic solution of i-PrONa, obtained by dissolving of sodium (0.017 g, 0.713 mmol, 1 equiv) in i-PrOH (16 ml), was treated with methyl[(4E)-1-benzyl-5-oxo-4-{1-[(pyridin-2-ylmethyl)amino]ethylidene}-4,5-dihydro-1H-pyrazol-3-yl]acetate (Compound of Formula (VIII) (0.270 g, 0.713 mmol, 1 equiv.). The reaction mixture was refluxed for 1 h, then cooled and neutralized to pH 7 by addition of 0.12 ml of a 20% aqueous HCl solution. 15 ml of i-PrOH were removed in vacuo and 10 ml of $H_2O$ were added before placing the flask in the fridge overnight. The white precipitate formed was filtered off, washed with water (2×3 ml), then with cyclohexane and dried in vacuo. 0.240 g of pure product 2-benzyl-4-methyl-5-(pyridin-2-ylmethyl)-1H-pyrazolo[4,3-c]pyridine-3,6(2H,5H)-dione was obtained. Yield 97%. $^1$H NMR (500 MHz, DMSO-$d_6$, ppm) 2.78 (s, 3H), 4.81 (s, 2H), 5.37 (s, 2H), 5.59 (s, 1H), 7.31-7.26 (m, 5H), 7.36 (m, 2H), 7.76 (td, J 7.6, 1.9 Hz, 1H), 8.46 (dt, J 4.2, 1.6 Hz, 1H), 10.34 (s, 1H); MS (ESI$^+$)=347.2.

Example 2

Formation of 2-(4-Chlorobenzyl)-4-Methyl-5-(Pyridin-2-Ylmethyl)-1H-Pyrazolo[4,3-c]Pyridine-3,6(2H,5H)-Dione (2) (Compound Ia, Scheme 1)

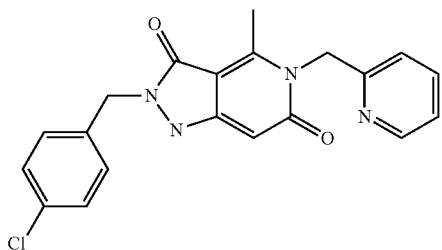 [SMILES: Cc1c2c(=O)n(Cc3ccc(Cl)cc3)[nH]c2cc(=O)n1Cc1ccccn1]

Following the general methods as outlined in Example 1, starting from (4-chlorobenzyl)hydrazine, dimethyl 3-oxopentanedioate, 1,1,1-triethoxyethane and 1-pyridin-2-ylmethanamine, the title compound (2) was isolated as a beige solid in 48% yield (99% purity by HPLC). MS (ESI$^+$): 381.5; MS (ESI$^-$): 379.8.

Example 3

Formation of 2-Benzyl-4-Methyl-5-[3-(Trifluoromethoxy)Phenyl]-1H-Pyrazolo[4,3-c]Pyridine-3,6(2H,5H)-Dione (3) (Compound Ia, Scheme 1)

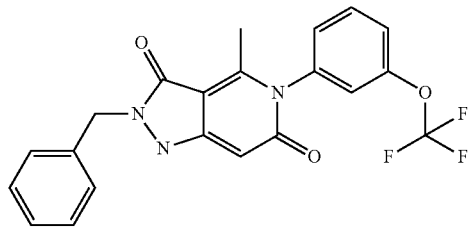 [SMILES: Cc1c2c(=O)n(Cc3ccccc3)[nH]c2cc(=O)n1-c1cccc(OC(F)(F)F)c1]

Following the general methods as outlined in Example 1, starting from benzylamine, dimethyl 3-oxopentanedioate, 1,1,1-triethoxyethane and 3-(trifluoromethoxy)aniline, the title compound (3) was isolated as a white solid in 43% yield (98% purity by HPLC). MS (ESI$^+$): 416.5; MS (ESI$^-$): 414.5.

Example 4

Formation of 2,4-Dimethyl-5-(Pyridin-2-Ylmethyl)-1H-Pyrazolo[4,3-c]Pyridine-3,6(2H,5H)-Dione (4) (Compound Ia, Scheme 1)

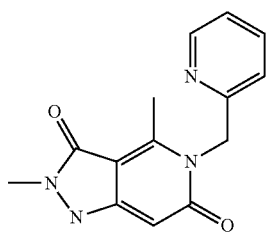 [SMILES: Cc1c2c(=O)n(C)[nH]c2cc(=O)n1Cc1ccccn1]

Following the general methods as outlined in Example 1, starting from methylhydrazine, dimethyl 3-oxopentanedioate, 1,1,1-triethoxyethane and 1-pyridin-2-ylmethanamine, the title compound (4) was isolated as a beige solid in 35% yield (99% purity by HPLC). MS (ESI$^+$): 271.3; MS (ESI$^-$): 269.5.

Example 5

Formation of 2,4,5-Trimethyl-1H-Pyrazolo[4,3-c]Pyridine-3,6(2H,5H)-Dione (5) (Compound Ia, Scheme 1)

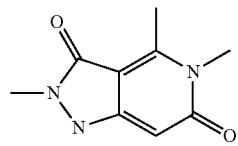

Following the general methods as outlined in Example 1, starting from methylhydrazine, dimethyl 3-oxopentanedioate, 1,1,1-triethoxyethane and methylamine, the title compound (5) was isolated as a beige solid in 40% yield (97% purity by HPLC). MS (ESI$^+$): 194.3; MS (ESI$^-$): 192.5.

Example 6

Formation of 5-(Furan-2-Ylmethyl)-2,4-Dimethyl-1H-Pyrazolo[4,3-c]Pyridine-3,6(2H,5H)-Dione (6) (Compound Ia, Scheme 1)

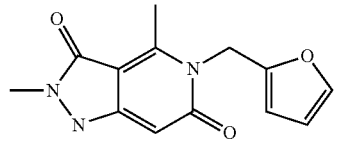 [SMILES: Cc1c2c(=O)n(C)[nH]c2cc(=O)n1Cc1ccco1]

Following the general methods as outlined in Example 1, starting from methylhydrazine, dimethyl 3-oxopentanedioate, 1,1,1-triethoxyethane and 1-furan-2-ylmethanamine, the

Example 7

Formation of 5-(4-Chlorobenzyl)-2,4-Dimethyl-1H-Pyrazolo[4,3-c]Pyridine-3,6 (2H,5H)-Dione (7) (Compound Ia, Scheme 1)

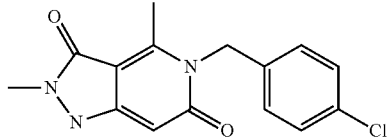 [SMILES: Cc1c2c(=O)n(C)[nH]c2cc(=O)n1Cc1ccc(Cl)cc1]

Following the general methods as outlined in Example 1, starting from methylhydrazine, dimethyl 3-oxopentanedioate, 1,1,1-triethoxyethane and para-chlorobenzylamine, the title compound (7) was isolated as a beige solid in 45% yield (97% purity by HPLC). MS (ESI$^+$): 304.8; MS (ESI$^-$): 302.7.

Example 8

Formation of 4-Butyl-5-(4-Chlorobenzyl)-2-Methyl-1H-Pyrazolo[4,3-c]Pyridine-3,6(2H,5H)-Dione (8) (Compound Ia, Scheme 1)

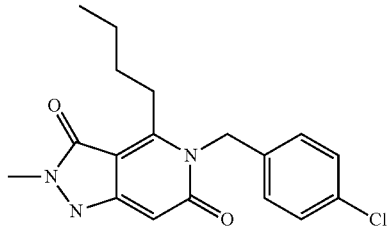 [SMILES: CCCCc1c2c(=O)n(C)[nH]c2cc(=O)n1Cc1ccc(Cl)cc1]

Following the general methods as outlined in Example 1, starting from methylhydrazine, dimethyl 3-oxopentanedioate, 1,1,1-triethoxypentane and para-chlorobenzylamine, the title compound (8) was isolated as a beige solid in 49% yield (98% purity by HPLC). MS (ESI$^+$): 346.8; MS (ESI$^-$): 344.6.

Example 9

Formation of 4-Butyl-2-Methyl-5-(Pyridin-2-Ylmethyl)-1H-Pyrazolo[4,3-c]Pyridine-3,6(2H,5H)-Dione (9) (Compound Ia, Scheme 1)

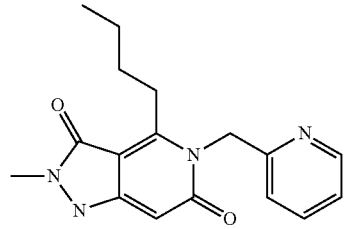 [SMILES: CCCCc1c2c(=O)n(C)[nH]c2cc(=O)n1Cc1ccccn1]

Following the general methods as outlined in Example 1, starting from methylhydrazine, dimethyl 3-oxopentanedioate, 1,1,1-triethoxypentane and 1-pyridin-2-ylmethanamine, the title compound (9) was isolated as a beige solid in 48% yield (96% purity by HPLC). MS (ESI$^+$): 313.5; MS (ESI$^-$): 311.4.

Example 10

Formation of 5-(4-Chlorobenzyl)-4-Methyl-2-(2-Morpholin-4-Ylethyl)-1H-Pyrazolo[4,3-c]Pyridine-3,6(2H,5H)-Dione (10) (Compound Ia, Scheme 1)

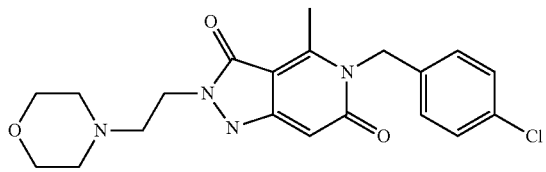 [SMILES: Cc1c2c(=O)n(CCN3CCOCC3)[nH]c2cc(=O)n1Cc1ccc(Cl)cc1]

Following the general methods as outlined in Example 1, starting from 4-(2-hydrazinoethyl)morpholine, dimethyl 3-oxopentanedioate, 1,1,1-triethoxyethane and para-chloro benzylamine, the title compound (10) was isolated as a white solid in 33% yield (95% purity by HPLC). MS (ESI$^+$): 403.9; MS (ESI$^-$): 401.8.

Example 11

Formation of 2-Benzyl-4-Butyl-5-(3,5-Dimethoxybenzyl)-1H-Pyrazolo[4,3-c]Pyridine-3,6(2H,5H)-Dione (11) (Compound Ia, Scheme 1)

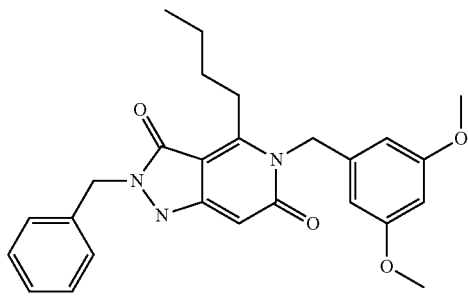 [SMILES: CCCCc1c2c(=O)n(Cc3ccccc3)[nH]c2cc(=O)n1Cc1cc(OC)cc(OC)c1]

Following the general methods as outlined in Example 1, starting from benzylhydrazine, dimethyl 3-oxopentanedioate, 1,1,1-triethoxypentane and 4,5-dimethoxy benzylamine, the title compound (11) was isolated as a beige solid in 31% yield (99% purity by HPLC). MS (ESI$^+$): 448.5; MS (ESI$^-$): 446.5.

Example 12

Formation of 2-Benzyl-4-Butyl-5-(Pyridin-2-Ylmethyl)-1H-Pyrazolo[4,3-c]Pyridine-3,6(2H,5H)-Dione (12) (Compound Ia, Scheme 1)

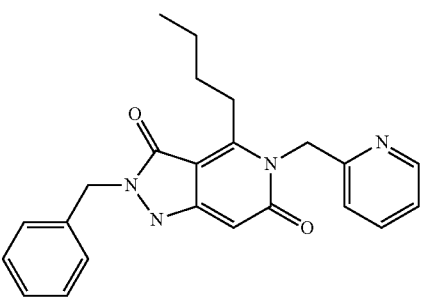 [SMILES: CCCCc1c2c(=O)n(Cc3ccccc3)[nH]c2cc(=O)n1Cc1ccccn1]

Following the general methods as outlined in Example 1, starting from benzylhydrazine, dimethyl 3-oxopentanedioate, 1,1,1-triethoxypentane and 1-pyridin-2-ylmethanamine, the title compound (12) was isolated as a white solid in 38% yield (98% purity by HPLC). MS (ESI$^+$): 389.5; MS (ESI$^-$): 387.6.

Example 13

Formation of 2-Cyclohexyl-4-Methyl-5-[2-(Morpholin-4-Ylmethyl)Benzyl]-1H-Pyrazolo[4,3-c]Pyridine-3,6(2H,5H)-Dione (13) (Compound Ia, Scheme 1)

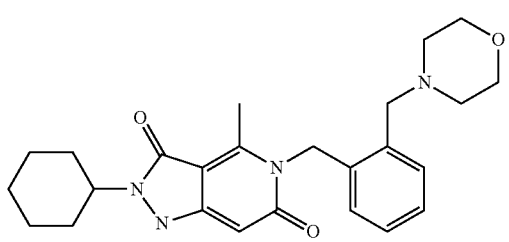 [SMILES: Cc1c2c(=O)n(C3CCCCC3)[nH]c2cc(=O)n1Cc1ccccc1CN1CCOCC1]

Following the general methods as outlined in Example 1, starting from cyclohexylhydrazine, dimethyl 3-oxopentanedioate, 1,1,1-triethoxyethane and 1-[2-(morpholin-4-ylmethyl)phenyl]methanamine, the title compound (13) was isolated as a beige solid in 31% yield (99% purity by HPLC). MS (ESI$^+$): 437.6; MS (ESI$^-$): 435.6.

Example 14

Formation of 2,4-Dimethyl-5-(2-Pyridin-2-Ylethyl)-1H-Pyrazolo[4,3-c]Pyridine-3,6(2H,5H)-Dione (14) (Compound Ia, Scheme 1)

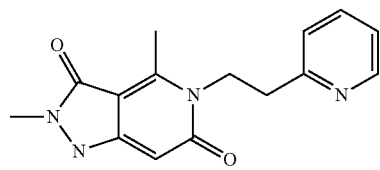 [SMILES: Cc1c2c(=O)n(C)[nH]c2cc(=O)n1CCc1ccccn1]

Following the general methods as outlined in Example 1, starting from methylhydrazine, dimethyl 3-oxopentanedioate, 1,1,1-triethoxyethane and 2-pyridin-2-ylethanamine, the title compound (14) was isolated as a yellowish solid in 43% yield (96% purity by HPLC). MS (ESI$^+$): 285.3; MS (ESI$^-$): 283.5.

Example 15

Formation of 2-(2-Methoxyethyl)-4-Methyl-5-(2-Pyridin-2-Ylethyl)-1H-Pyrazolo[4,3-c]Pyridine-3,6(2H,5H)-Dione (15) (Compound Ia, Scheme 1)

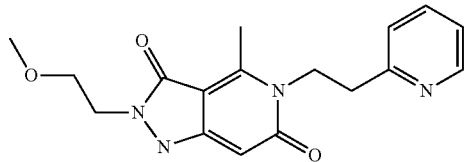 [SMILES: COCCn1[nH]c2cc(=O)n(CCc3ccccn3)c(C)c2c1=O]

Following the general methods as outlined in Example 1, starting from (2-methoxyethyl)hydrazine, dimethyl 3-oxopentanedioate, 1,1,1-triethoxyethane and 2-pyridin-2-ylethanamine, the title compound (15) was isolated as a beige solid in 47% yield (99% purity by HPLC). MS (ESI$^+$): 329.5; MS (ESI$^-$): 327.4.

Example 16

Formation of 2,4-Dimethyl-5-(2-Morpholin-4-Ylethyl)-1H-Pyrazolo[4,3-c]Pyridine-3,6(2H,5H)-Dione (16) (Compound Ia, Scheme 1)

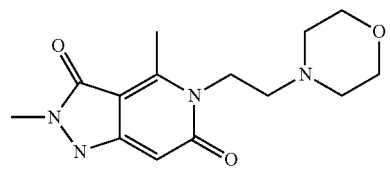 [SMILES: Cc1c2c(=O)n(C)[nH]c2cc(=O)n1CCN1CCOCC1]

Following the general methods as outlined in Example 1, starting from methylhydrazine, dimethyl 3-oxopentanedioate, 1,1,1-triethoxyethane and 2-morpholin-4-ylethanamine, the title compound (16) was isolated as a white solid in 43% yield (99% purity by HPLC). MS (ESI$^+$): 293.4; MS (ESI$^-$): 291.3.

Example 17

2-Benzyl-4-(3-Methoxybenzyl)-5-(Pyridin-2-Ylmethyl)-1H-Pyrazolo[4,3-c]Pyridine-3,6(2H,5H)-Dione (21)(Compound Ia, Scheme 2)

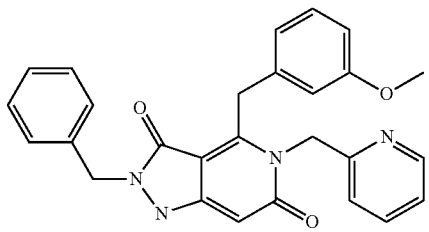 [SMILES: COc1cccc(Cc2c3c(=O)n(Cc4ccccc4)[nH]c3cc(=O)n2Cc2ccccn2)c1]

a) methyl(1-benzyl-5-hydroxy-1H-pyrazol-3-yl)acetate (Compound of Formula (IV), Scheme 2)

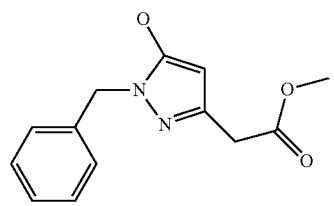 [SMILES: COC(=O)Cc1cc(O)n(Cc2ccccc2)n1]

To a suspension of benzylamine dihydrochloride (1.000 g, 5.126 mmol, 1 equiv.) in anhydrous toluene (25 ml) were added successively diisopropylethylamine (1.32 ml, 10.252 mmol, 2 equiv.) and dimethyl 3-oxopentanedioate (0.893 g, 5.126 mmol, 1 equiv.). The resulting mixture was heated at reflux for 18 h before being concentrated in vacuo. The resulting brown oil was purified by flash chromatography over SiO$_2$ (CH$_2$Cl$_2$:MeOH, 97:3). 0.810 g of pure methyl(1-benzyl-5-hydroxy-1H-pyrazol-3-yl)acetate was obtained as a white solid. Yield 64%. MS (ESI$^+$): 247.1; MS (ESI$^-$): 245.1.

b) methyl {1-benzyl-4-[(3-methoxyphenyl)acetyl]-5-oxo-4,5-dihydro-1H-pyrazol-3-yl}acetate (Compound of Formula (X), Scheme 2)

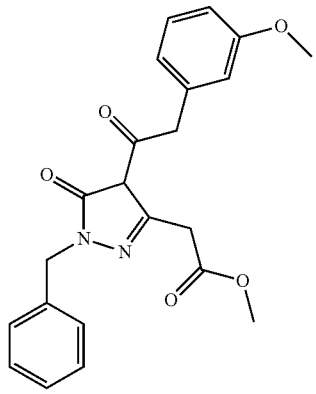 [SMILES: COC(=O)CC1=NN(Cc2ccccc2)C(=O)C1C(=O)Cc1cccc(OC)c1]

The mixture of the above obtained methyl(1-benzyl-5-hydroxy-1H-pyrazol-3-yl)acetate (Compound of Formula (IV), 1 g, 3.76 mmol, 1 eq.) and Ca(OH)$_2$ (2.78 g, 10 equiv.) was suspended in dioxane (30 mL). (3-methoxyphenyl)acetyl chloride 0.761 g, 1.1 equiv.) was added to the suspension under nitrogen. Then the mixture was heated at 100° C. for 45-60 minutes. The resulting red solution was concentrated in vacuo to afford a red syrup that was partitioned between ethylacetate and cold 0.1M HCl. Organic phases were washed with brine and dried over Na$_2$SO$_4$. Evaporation of solvent gave methyl methyl{1-benzyl-4-[(3-methoxyphenyl)acetyl]-5-oxo-4,5-dihydro-1H-pyrazol-3-yl}acetate as a pink solid (1.09 g, 70% yield, 89% HPLC purity). MS(ESI$^+$): 395.2; MS(ESI$^-$): 393.2.

c) methyl[(4Z)-1-benzyl-4-{2-(3-methoxyphenyl)-1-[(pyridin-2-ylmethyl)amino]ethylidene}-5-oxo-4,5-dihydro-1H-pyrazol-3-yl]acetate (Compound of Formula (VIII), Scheme 2)

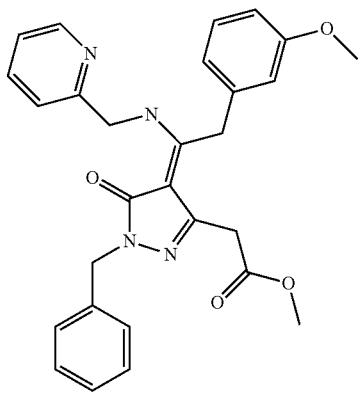 [SMILES: COC(=O)CC1=NN(Cc2ccccc2)C(=O)/C1=C(/Cc1cccc(OC)c1)NCc1ccccn1]

The mixture of the above obtained methyl{1-benzyl-4-[(3-methoxyphenyl)acetyl]-5-oxo-4,5-dihydro-1H-pyrazol-3-yl}acetate (Compound of Formula (X), 394 mg, 1 eq.) and 1-pyridin-2-ylmethanamine (119 mg, 1.1 eq.) and AcOH (60 mg, 1 eq.) were stirred at 80° C. under nitrogen in toluene/NMP(10/1)(10 mL) for 2 hours. The solvent was removed in vacuo. The resulting residue was portioned between ethylacetate and saturated solution of NaHCO$_3$. The organic phase was washed with brine and then dried over Na$_2$SO$_4$. Evaporation of solvent gave the pure methyl[(4Z)-1-benzyl-4-{2-(3-methoxyphenyl)-1-[(pyridin-2-ylmethyl)amino]ethylidene}-5-oxo-4,5-dihydro-1H-pyrazol-3-yl]acetate (160 mg, Yield: 33%) which was used in the following step without further purification.

d) 2-benzyl-4-(3-methoxybenzyl)-5-(pyridin-2-ylmethyl)-1H-pyrazolo[4,3-c]pyridine-3,6 (2H,5H)-dione (Compound of Formula (Ia), Scheme 2)

The above obtained methyl[(4Z)-1-benzyl-4-{2-(3-methoxyphenyl)-1-[(pyridin-2-yl methyl)amino]ethylidene}-5-oxo-4,5-dihydro-1H-pyrazol-3-yl]acetate (Compound of Formula (VIII) was treated with freshly prepared MeONa in MeOH (2M, 20 ml). The solution was stirred at room temperature until disappearance of the starting enamine (t=0.5-2 h). The reaction mixture was concentrated in vacuum to eliminate MeOH and the crude was dissolved in ethyl acetate (80 ml), extracted with water (30 ml*3). Then the combined inorganic layer was acidified to pH=6, extracted with ethyl acetate (30 ml*3), the combined organic layer was dried over Na$_2$SO$_4$, purified by TLC yielding the final product 2-benzyl-4-(3-methoxybenzyl)-5-(pyridin-2-ylmethyl)-1H-pyrazolo[4,3-c]pyridine-3,6(2H,5H)-dione as yellow oil (65 mg, yield: 43%). $^1$HNMR (400 MHz, DMSO-d6): 3.635 (s, 3H); 4.702 (s, 2H); 4.860 (s, 2H); 5.274 (s, 2H), 5.696 (s, 1H); 6.646-6.716 (m, 3H), 7.104-7.144 (m, 2H); 7.277-7.416 (m, 6H); 7.823-7.859 (t, 1H); 8.492-8.501 (d, 1H). MS(ESI$^+$): 453.2; MS(ESI$^-$): 451.2.

The structures of further compounds synthesised herein are listed in the following Table 1:

TABLE 1

| Compound | Structure | Name | Data | Method |
|---|---|---|---|---|
| 17 | 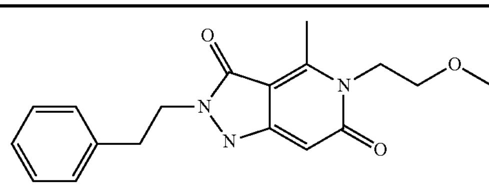 | 5-(2-methoxyethyl)-4-methyl-2-(2-phenylethyl)-1H-pyrazolo[4,3-c]pyridine-3,6(2H,5H)-dione | MS (ESI$^+$): 328.5 | Ex. 1, Scheme 1 |

TABLE 1-continued

| Compound | Structure | Name | Data | Method |
|---|---|---|---|---|
| 18 | 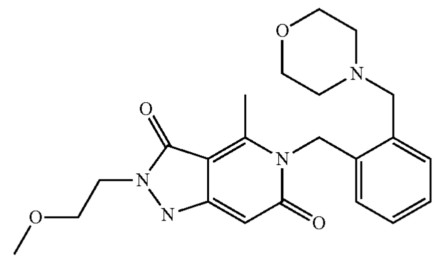 [SMILES: COCCn1[nH]c2cc(=O)n(Cc3ccccc3CN3CCOCC3)c(C)c2c1=O] | 2-(2-methoxyethyl)-4-methyl-5-[2-(morpholin-4ylmethyl)benzyl]-1H-pyrazolo[4,3-c]pyridine-3,6(2H,5H)-dione | MS (ESI+): 413.7 | Ex. 1, Scheme 1 |
| 19 | 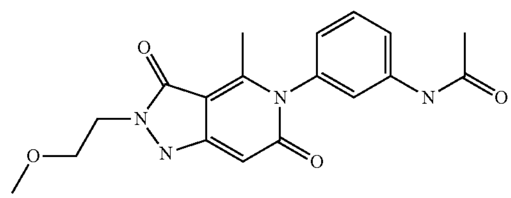 [SMILES: COCCn1[nH]c2cc(=O)n(-c3cccc(NC(C)=O)c3)c(C)c2c1=O] | N-{3-[2-(2-methoxyethyl)-4-methyl-3,6-dioxo-1,2,3,6-tetrahydro-5H-pyrazolo[4,3-c]pyridin-5-yl]phenyl}acetamide | MS (ESI+): 357.6 | Ex. 1, Scheme 1 |
| 20 | 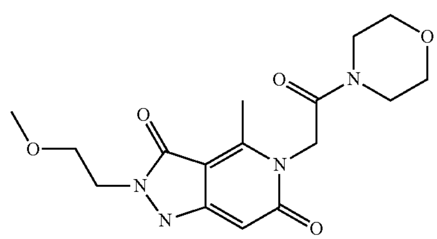 [SMILES: COCCn1[nH]c2cc(=O)n(CC(=O)N3CCOCC3)c(C)c2c1=O] | 2-(2-methoxyethyl)-4-methyl-5-(2-morpholin-4-yl-2-oxoethyl)-1H-pyrazolo 4,3-c]pyridine-3,6(2H,5H)-dione | MS (ESI+): 351.4 | Ex. 1, Scheme 1 |
| 21 | 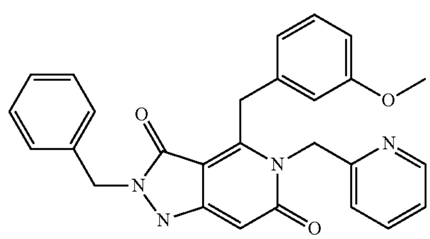 [SMILES: COc1cccc(Cc2c3c(=O)n(Cc4ccccc4)[nH]c3cc(=O)n2Cc2ccccn2)c1] | 2-benzyl-4-(3-methoxy benzyl)-5-(pyridin-2-yl methyl)-1H-pyrazolo[4,3-c]pyridine-3,6(2H,5H)-dione | MS (ESI+): 453.6 | Ex. 17, Scheme 2 |
| 22 | 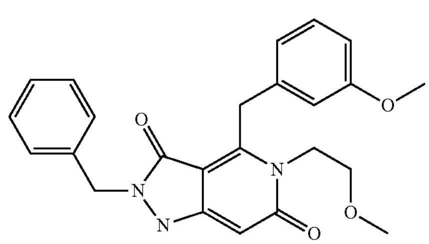 [SMILES: COCCn1c(Cc2cccc(OC)c2)c2c(=O)n(Cc3ccccc3)[nH]c2cc1=O] | 2-benzyl-4-(3-methoxy benzyl)-5-(2-methoxyethyl)-1H-pyrazolo[4,3-c]pyridine-3,6(2H,5H)-dione | MS (ESI+): 420.5 | Ex. 17, Scheme 2 |
| 23 | 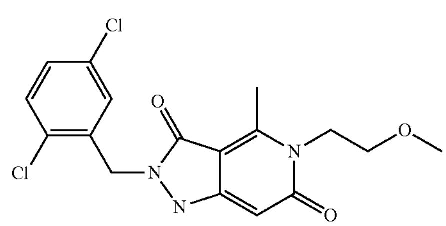 [SMILES: COCCn1c(C)c2c(=O)n(Cc3cc(Cl)ccc3Cl)[nH]c2cc1=O] | 2-(2,5-dichlorobenzyl)-5-(2-methoxyethyl)-4-methyl-1H-pyrazolo[4,3-c]pyridine-3,6(2H,5H)-dione | MS (ESI+): 383.4 | Ex. 1, Scheme 1 |

TABLE 1-continued

| Compound | Structure | Name | Data | Method |
|---|---|---|---|---|
| 24 | 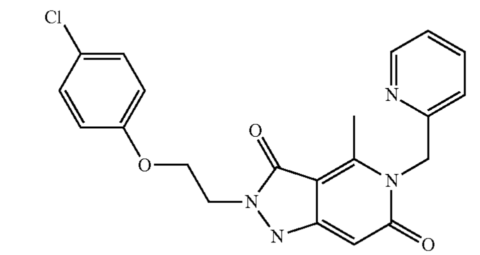 [SMILES: Cc1c2c(=O)n(CCOc3ccc(Cl)cc3)[nH]c2cc(=O)n1Cc1ccccn1] | 2-[2-(4-chlorophenoxy)ethyl]-4-methyl-5-(pyridin-2-yl methyl)-1H-pyrazolo[4,3-c]pyridine-3,6(2H,5H)-dione | MS (ESI+): 411.9 | Ex. 1, Scheme 1 |
| 25 | 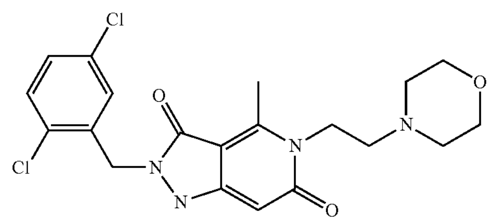 [SMILES: Cc1c2c(=O)n(Cc3cc(Cl)ccc3Cl)[nH]c2cc(=O)n1CCN1CCOCC1] | 2-(2,5-dichlorobenzyl)-4-methyl-5-(2-morpholin-4-ylethyl)-1H-pyrazolo[4,3-c]pyridine-3,6(2H,5H)-dione | MS (ESI+): 438.9 | Ex. 1, Scheme 1 |
| 26 | 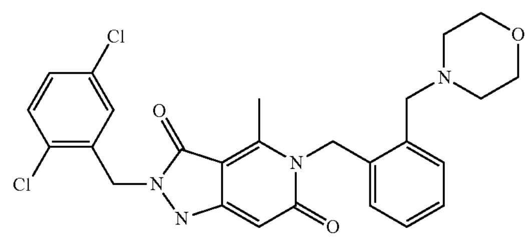 [SMILES: Cc1c2c(=O)n(Cc3cc(Cl)ccc3Cl)[nH]c2cc(=O)n1Cc1ccccc1CN1CCOCC1] | 2-(2,5-dichlorobenzyl)-4-methyl-5-[2-(morpholin-4-ylmethyl)benzyl]-1H-pyrazolo[4,3-c]pyridine-3,6(2H,5H)-dione | MS (ESI+): 514.6 | Ex. 1, Scheme 1 |
| 27 | 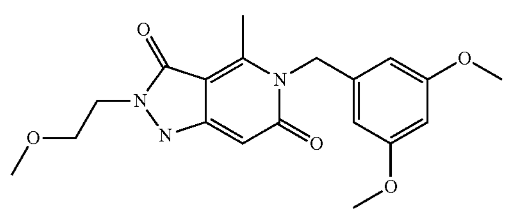 | 5-(3,5-dimethoxybenzyl)-2-(2-methoxyethyl)-4-methyl-1H-pyrazolo[4,3-c]pyridine-3,6(2H,5H)-dione | MS (ESI+): 374.6 | Ex. 1, Scheme 1 |
| 28 | 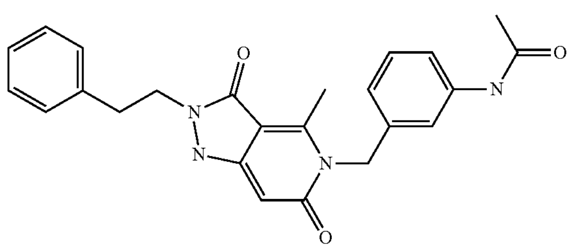 [SMILES: CC(=O)Nc1cccc(Cn2c(C)c3c(=O)n(CCc4ccccc4)[nH]c3cc2=O)c1] | N-(3-{[4-methyl-3,6-dioxo-2-(2-phenylethyl)-1,2,3,6-tetrahydro-5H-pyrazolo[4,3-c]pyridin-5-yl]methyl}phenyl)acetamide | MS (ESI+): 417.5 | Ex. 1, Scheme 1 |
| 29 | 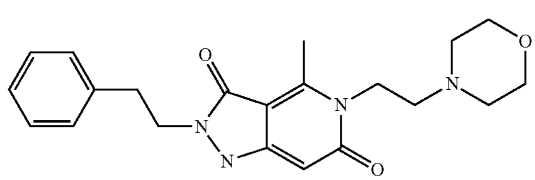 [SMILES: Cc1c2c(=O)n(CCc3ccccc3)[nH]c2cc(=O)n1CCN1CCOCC1] | 4-methyl-5-(2-morpholin-4-ylethyl)-2-(2-phenylethyl)-1H-pyrazolo[4,3-c]pyridine-3,6(2H,5H)-dione | MS (ESI+): 383.5 | Ex. 1, Scheme 1 |
| 30 | 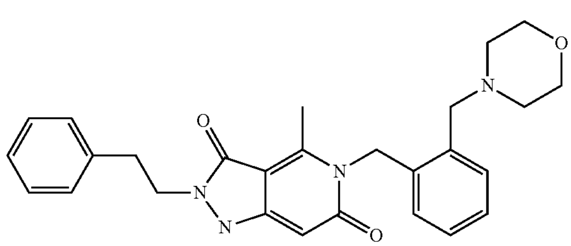 [SMILES: Cc1c2c(=O)n(CCc3ccccc3)[nH]c2cc(=O)n1Cc1ccccc1CN1CCOCC1] | 4-methyl-5-[2-(morpholin-4-ylmethyl)benzyl]-2-(2-phenyl ethyl)-1H-pyrazolo[4,3-c]pyridine-3,6(2H,5H)-dione | MS (ESI+): 459.7 | Ex. 1, Scheme 1 |

TABLE 1-continued

| Compound | Structure | Name | Data | Method |
|---|---|---|---|---|
| 31 | 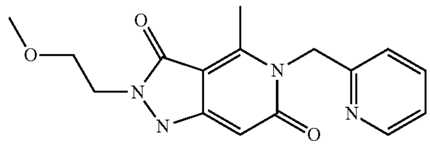 [SMILES: COCCn1[nH]c2cc(=O)n(Cc3ccccn3)c(C)c2c1=O] | 2-(2-methoxyethyl)-4-methyl-5-(pyridin-2-ylmethyl)-1H-pyrazolo[4,3-c]pyridine-3,6(2H,5H)-dione | MS (ESI+): 315.3 | Ex. 1, Scheme 1 |
| 32 | 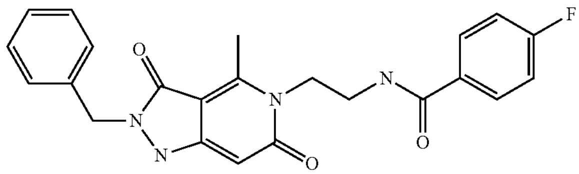 [SMILES: Cc1c2c(=O)n(Cc3ccccc3)[nH]c2cc(=O)n1CCNC(=O)c1ccc(F)cc1] | N-[2-(2-benzyl-4-methyl-3,6-dioxo-1,2,3,6-tetrahydro-5H-pyrazolo[4,3-c]pyridin-5-yl)ethyl]-4-fluorobenzamide | MS (ESI+): 421.4 | Ex. 1, Scheme 1 |
| 33 | 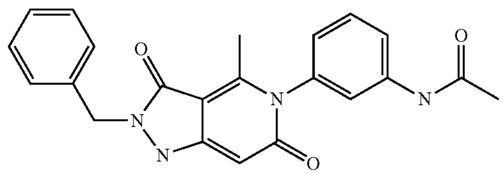 [SMILES: CC(=O)Nc1cccc(-n2c(C)c3c(=O)n(Cc4ccccc4)[nH]c3cc2=O)c1] | N-[3-(2-benzyl-4-methyl-3,6-dioxo-1,2,3,6-tetrahydro-5H-pyrazolo[4,3-c]pyridin-5-yl)phenyl]acetamide | MS (ESI+): 389.5 | Ex. 1, Scheme 1 |
| 34 | 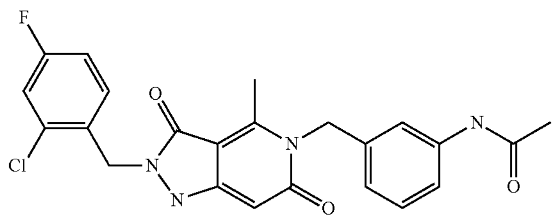 [SMILES: CC(=O)Nc1cccc(Cn2c(C)c3c(=O)n(Cc4ccc(F)cc4Cl)[nH]c3cc2=O)c1] | N-(3-{[2-(2-chloro-4-fluoro benzyl)-4-methyl-3,6-dioxo-1,2,3,6-tetrahydro-5H-pyrazolo[4,3-c]pyridin-5-yl]methyl}phenyl)acetamide | MS (ESI+): 456.0 | Ex. 1, Scheme 1 |
| 35 | 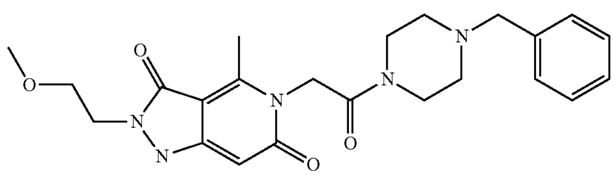 [SMILES: COCCn1[nH]c2cc(=O)n(CC(=O)N3CCN(Cc4ccccc4)CC3)c(C)c2c1=O] | 5-[2-(4-benzylpiperazin-1-yl)-2-oxoethyl]-2-(2-methoxy ethyl)-4-methyl-1H-pyrazolo[4,3-c]pyridine-3,6(2H,5H)-dione | MS (ESI+): 440.6 | Ex. 1, Scheme 1 |
| 36 | 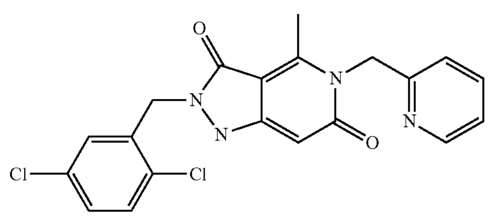 [SMILES: Cc1c2c(=O)n(Cc3cc(Cl)ccc3Cl)[nH]c2cc(=O)n1Cc1ccccn1] | 2-(2,5-dichlorobenzyl)-4-methyl-5-(pyridin-2-yl methyl)-1H-pyrazolo[4,3-c]pyridine-3,6(2H,5H)-dione | MS (ESI+): 416.4 | Ex. 1, Scheme 1 |
| 37 | 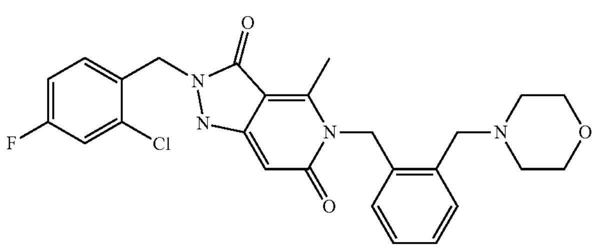 [SMILES: Cc1c2c(=O)n(Cc3ccc(F)cc3Cl)[nH]c2cc(=O)n1Cc1ccccc1CN1CCOCC1] | 2-(2-chloro-4-fluorobenzyl)-4-methyl-5-[2-(morpholin-4-ylmethyl)benzyl]-1H-pyrazolo[4,3-c]pyridine-3,6(2H,5H)-dione | MS (ESI+): 498.0 | Ex. 1, Scheme 1 |
| 38 | 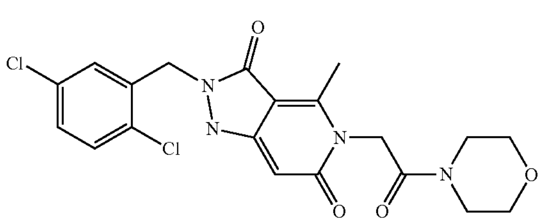 [SMILES: Cc1c2c(=O)n(Cc3cc(Cl)ccc3Cl)[nH]c2cc(=O)n1CC(=O)N1CCOCC1] | 2-(2,5-dichlorobenzyl)-4-methyl-5-(2-morpholin-4-yl-2-oxoethyl)-1H-pyrazolo[4,3-c]pyridine-3,6(2H,5H)-dione | MS (ESI+): 452.9 | Ex. 1, Scheme 1 |

TABLE 1-continued

| Compound | Structure | Name | Data | Method |
|---|---|---|---|---|
| 39 | 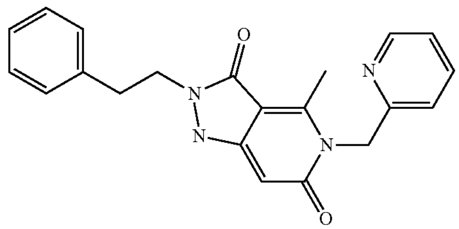 [SMILES: Cc1c2c(=O)n(CCc3ccccc3)[nH]c2cc(=O)n1Cc1ccccn1] | 4-methyl-2-(2-phenylethyl)-5-(pyridin-2-ylmethyl)-1H-pyrazolo[4,3-c]pyridine-3,6(2H,5H)-dione | MS (ESI+): 361.4 | Ex. 1, Scheme 1 |
| 40 | 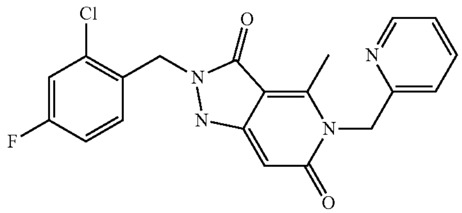 [SMILES: Cc1c2c(=O)n(Cc3ccc(F)cc3Cl)[nH]c2cc(=O)n1Cc1ccccn1] | 2-(2-chloro-4-fluorobenzyl)-4-methyl-5-(pyridin-2-yl methyl)-1H-pyrazolo[4,3-c]pyridine-3,6(2H,5H)-dione | MS (ESI+): 400.1 | Ex. 1, Scheme 1 |
| 41 | 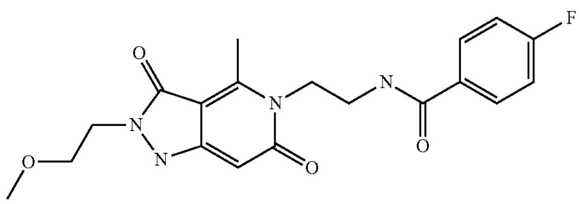 [SMILES: COCCn1[nH]c2cc(=O)n(CCNC(=O)c3ccc(F)cc3)c(C)c2c1=O] | 4-fluoro-N-{2-[2-(2-methoxy ethyl)-4-methyl-3,6-dioxo-1,2,3,6-tetrahydro-5H-pyrazolo[4,3-c]pyridin-5-yl]ethyl}benzamide | MS (ESI+): 389.5 | Ex. 1, Scheme 1 |
| 42 | 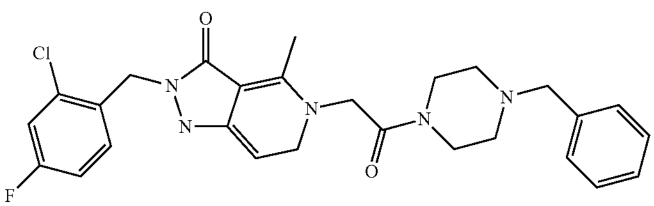 | 5-[2-(4-benzylpiperazin-1-yl)-2-oxoethyl]-2-(2-chloro-4-fluorobenzyl)-4-methyl-1H-pyrazolo[4,3-c]pyridine-3,6(2H,5H)-dione | MS (ESI+): 525.1 | Ex. 1, Scheme 1 |
| 43 | 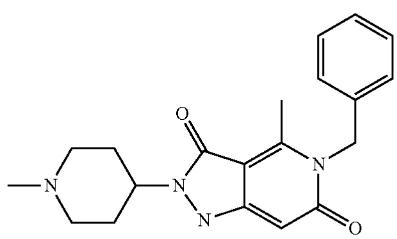 [SMILES: Cc1c2c(=O)n(C3CCN(C)CC3)[nH]c2cc(=O)n1Cc1ccccc1] | 5-benzyl-4-methyl-2-(1-methylpiperidin-4-yl)-1H-pyrazolo[4,3-c]pyridine-3,6(2H,5H)-dione | MS (ESI+): 353.5 | Ex. 1, Scheme 1 |
| 44 | 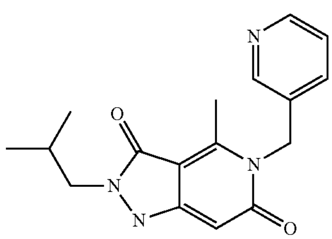 [SMILES: Cc1c2c(=O)n(CC(C)C)[nH]c2cc(=O)n1Cc1cccnc1] | 4-methyl-2-(2-methylpropyl)-5-(pyridin-3-ylmethyl)-1H-pyrazolo[4,3-c]pyridine-3,6(2H,5H)-dione | MS (ESI+): 313.5 | Ex. 1, Scheme 1 |
| 45 | 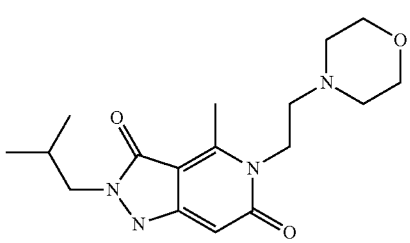 [SMILES: Cc1c2c(=O)n(CC(C)C)[nH]c2cc(=O)n1CCN1CCOCC1] | 4-methyl-2-(2-methylpropyl)-5-(2-morpholin-4-ylethyl)-1H-pyrazolo[4,3-c]pyridine-3,6(2H,5H)-dione | MS (ESI+): 335.6 | Ex. 1, Scheme 1 |

TABLE 1-continued

| Compound | Structure | Name | Data | Method |
|---|---|---|---|---|
| 46 | 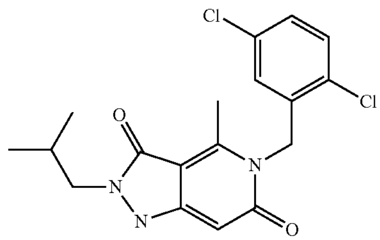 [SMILES: Cc1c2c(=O)n(CC(C)C)[nH]c2cc(=O)n1Cc1cc(Cl)ccc1Cl] | 5-(2,5-dichlorobenzyl)-4-methyl-2-(2-methylpropyl)-1H-pyrazolo[4,3-c]pyridine-3,6(2H,5H)-dione | MS (ESI+): 381.3 | Ex. 1, Scheme 1 |
| 47 | 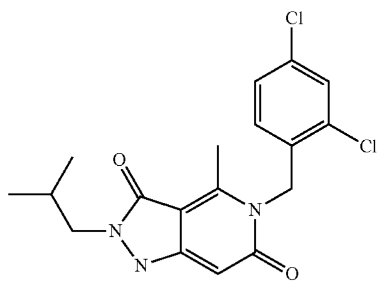 [SMILES: Cc1c2c(=O)n(CC(C)C)[nH]c2cc(=O)n1Cc1ccc(Cl)cc1Cl] | 5-(2,4-dichlorobenzyl)-4-methyl-2-(2-methylpropyl)-1H-pyrazolo[4,3-c]pyridine-3,6(2H,5H)-dione | MS (ESI+): 381.3 | Ex. 1, Scheme 1 |
| 48 | 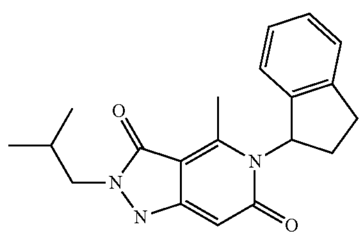 [SMILES: Cc1c2c(=O)n(CC(C)C)[nH]c2cc(=O)n1C1CCc2ccccc21] | 5-(2,3-dihydro-1H-inden-1-yl)-4-methyl-2-(2-methyl propyl)-1H-pyrazolo[4,3-c]pyridine-3,6(2H,5H)-dione | MS (ESI+): 338.5 | Ex. 1, Scheme 1 |
| 49 | 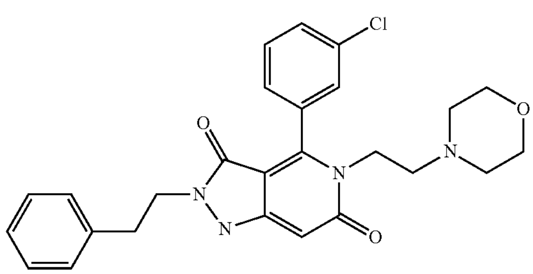 [SMILES: O=c1c2c(-c3cccc(Cl)c3)n(CCN3CCOCC3)c(=O)cc2[nH]n1CCc1ccccc1] | 4-(3-chlorophenyl)-5-(2-morpholin-4-ylethyl)-2-(2-phenylethyl)-1H-pyrazolo[4,3-c]pyridine-3,6(2H,5H)-dione | MS (ESI+): 480.2 | Ex. 17, Scheme 2 |
| 50 | 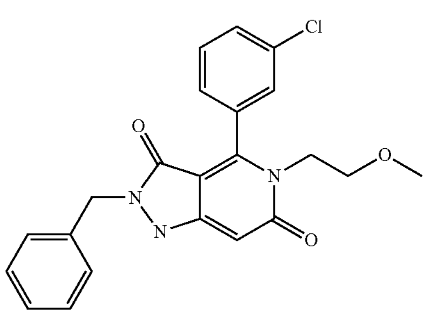 [SMILES: COCCn1c(-c2cccc(Cl)c2)c2c(=O)n(Cc3ccccc3)[nH]c2cc1=O] | 2-benzyl-4-(3-chlorophenyl)-5-(2-methoxyethyl)-1H-pyrazolo[4,3-c]pyridine-3,6(2H,5H)-dione | MS (ESI+): 411.1 | Ex. 17, Scheme 2 |

TABLE 1-continued

| Compound | Structure | Name | Data | Method |
|---|---|---|---|---|
| 51 | 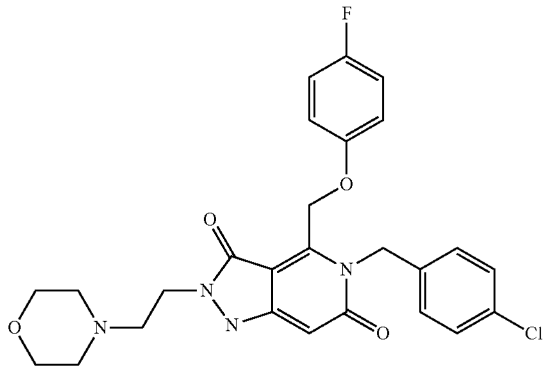 [SMILES: O=c1c2c(COc3ccc(F)cc3)n(Cc3ccc(Cl)cc3)c(=O)cc2[nH]n1CCN1CCOCC1] | 5-(4-chlorobenzyl)-4-[(4-fluorophenoxy)methyl]-2-(2-morpholin-4-ylethyl)-1H-pyrazolo[4,3-c]pyridine-3,6(2H,5H)-dione | MS (ESI+): 514.2 | Ex. 17, Scheme 2 |
| 52 | 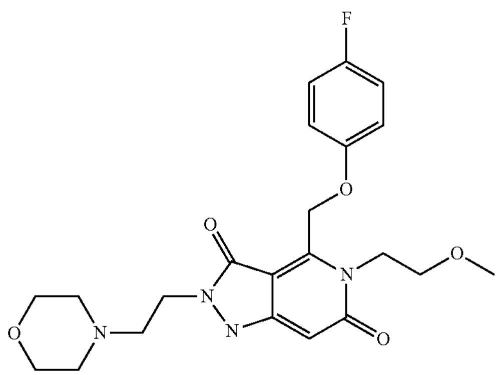 [SMILES: COCCn1c(COc2ccc(F)cc2)c2c(=O)n(CCN3CCOCC3)[nH]c2cc1=O] | 4-[(4-fluorophenoxy)methyl]-5-(2-methoxyethyl)-2-(2-morpholin-4-ylethyl)-1H-pyrazolo[4,3-c]pyridine-3,6(2H,5H)-dione | MS (ESI+): 447.6 | Ex. 17, Scheme 2 |
| 53 | 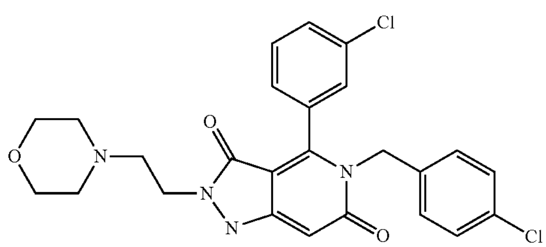 [SMILES: O=c1c2c(-c3cccc(Cl)c3)n(Cc3ccc(Cl)cc3)c(=O)cc2[nH]n1CCN1CCOCC1] | 5-(4-chlorobenzyl)-4-(3-chlorophenyl)-2-(2-morpholin-4-ylethyl)-1H-pyrazolo[4,3-c]pyridine-3,6(2H,5H)-dione | MS (ESI+): 500.8 | Ex. 17, Scheme 2 |
| 54 | 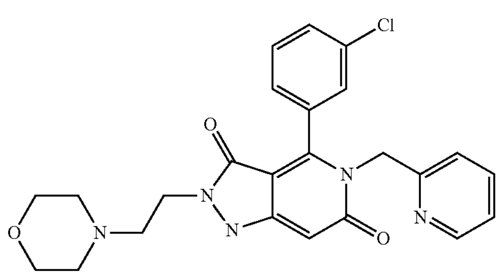 [SMILES: O=c1c2c(-c3cccc(Cl)c3)n(Cc3ccccn3)c(=O)cc2[nH]n1CCN1CCOCC1] | 4-(3-chlorophenyl)-2-(2-morpholin-4-ylethyl)-5-(pyridin-2-ylmethyl)-1H-pyrazolo[4,3-c]pyridine-3,6(2H,5H)-dione | MS (ESI+): 467.2 | Ex. 17, Scheme 2 |
| 55 | 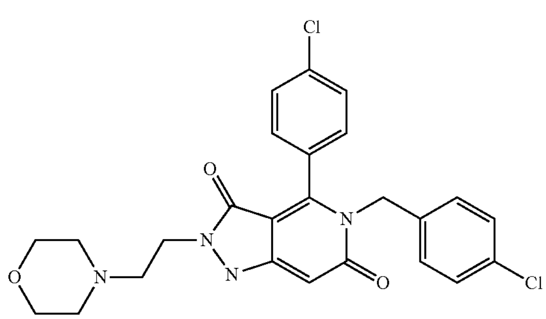 [SMILES: O=c1c2c(-c3ccc(Cl)cc3)n(Cc3ccc(Cl)cc3)c(=O)cc2[nH]n1CCN1CCOCC1] | 5-(4-chlorobenzyl)-4-(4-chlorophenyl)-2-(2-morpholin-4-ylethyl)-1H-pyrazolo[4,3-c]pyridine-3,6(2H,5H)-dione | MS (ESI+): 500.7 | Ex. 17, Scheme 2 |

TABLE 1-continued

| Compound | Structure | Name | Data | Method |
|---|---|---|---|---|
| 56 | 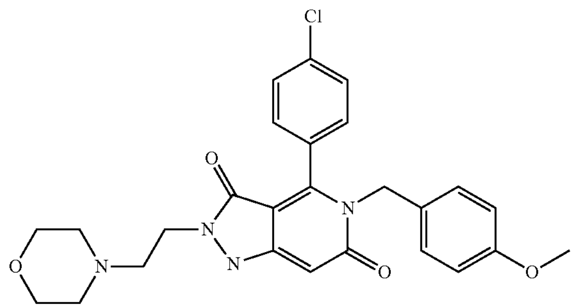 [SMILES: COc1ccc(Cn2c(-c3ccc(Cl)cc3)c3c(=O)n(CCN4CCOCC4)[nH]c3cc2=O)cc1] | 4-(4-chlorophenyl)-5-(4-methoxybenzyl)-2-(2-morpholin-4-ylethyl)-1H-pyrazolo[4,3-c]pyridine-3,6(2H,5H)-dione | MS (ESI+): 496.1 | Ex. 17, Scheme 2 |
| 57 | 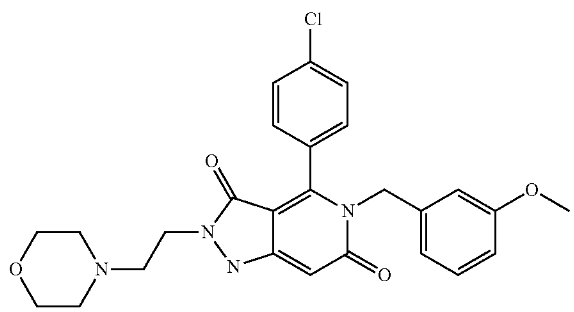 [SMILES: COc1cccc(Cn2c(-c3ccc(Cl)cc3)c3c(=O)n(CCN4CCOCC4)[nH]c3cc2=O)c1] | 4-(4-chlorophenyl)-5-(3-methoxybenzyl)-2-(2-morpholin-4-ylethyl)-1H-pyrazolo[4,3-c]pyridine-3,6(2H,5H)-dione | MS (ESI+): 496.2 | Ex. 17, Scheme 2 |
| 58 | 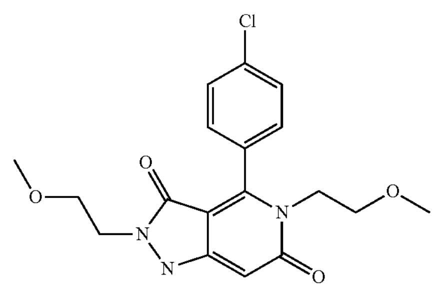 | 4-(4-chlorophenyl)-2,5-bis(2-methoxyethyl)-1H-pyrazolo[4,3-c]pyridine-3,6(2H,5H)-dione | MS (ESI+): 378.9 | Ex. 17, Scheme 2 |
| 59 | 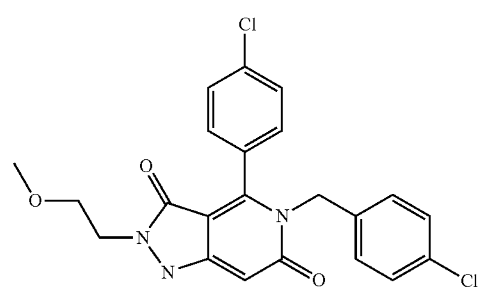 [SMILES: COCCn1[nH]c2cc(=O)n(Cc3ccc(Cl)cc3)c(-c3ccc(Cl)cc3)c2c1=O] | 5-(4-chlorobenzyl)-4-(4-chlorophenyl)-2-(2-methoxy ethyl)-1H-pyrazolo[4,3-c]pyridine-3,6(2H,5H)-dione | MS (ESI+): 445.8 | Ex. 17, Scheme 2 |
| 60 | 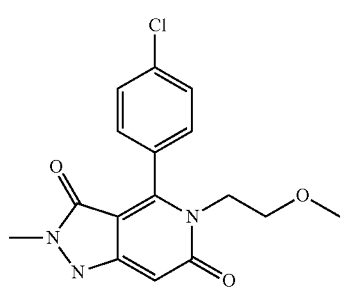 | 4-(4-chlorophenyl)-5-(2-methoxyethyl)-2-methyl-1H-pyrazolo[4,3-c]pyridine-3,6-(2H,5H)-dione | MS (ESI+): 334.9 | Ex. 17, Scheme 2 |

TABLE 1-continued

| Compound | Structure | Name | Data | Method |
|---|---|---|---|---|
| 61 | 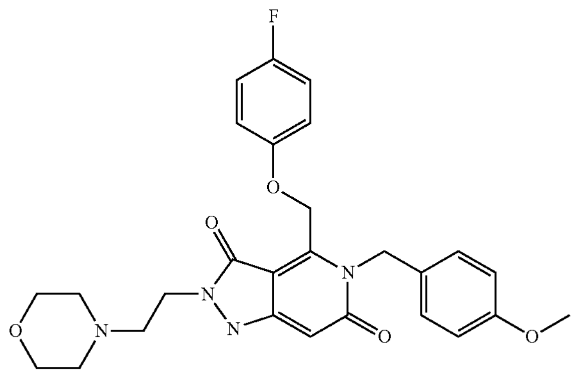 [SMILES: COc1ccc(Cn2c(COc3ccc(F)cc3)c3c(=O)n(CCN4CCOCC4)[nH]c3cc2=O)cc1] | 4-[(4-fluorophenoxy)methyl]-5-(4-methoxybenzyl)-2-(2-morpholin-4-ylethyl)-1H-pyrazolo[4,3-c]pyridine-3,6-(2H,5H)-dione | MS (ESI+): 509.7 | Ex. 17, Scheme 2 |
| 62 | 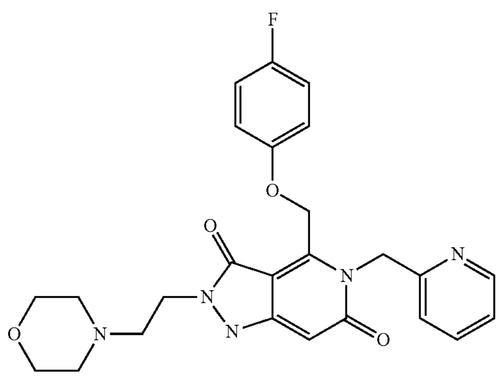 [SMILES: O=c1c2c(COc3ccc(F)cc3)n(Cc3ccccn3)c(=O)cc2[nH]n1CCN1CCOCC1] | 4-[(4-fluorophenoxy)methyl]-2-(2-morpholin-4-ylethyl)-5-(pyridin-2-ylmethyl)-1H-pyrazolo[4,3-c]pyridine-3,6(2H,5H)-dione | MS (ESI+): 480.6 | Ex. 17, Scheme 2 |
| 63 | 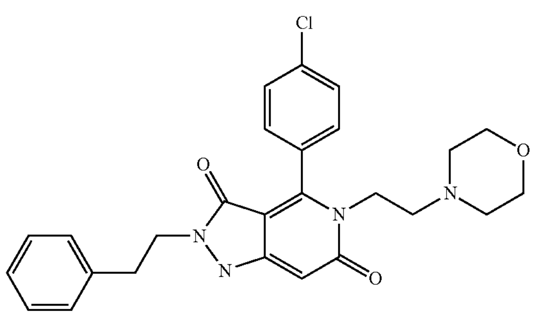 [SMILES: O=c1c2c(-c3ccc(Cl)cc3)n(CCN3CCOCC3)c(=O)cc2[nH]n1CCc1ccccc1] | 4-(4-chlorophenyl)-5-(2-morpholin-4-ylethyl)-2-(2-phenylethyl)-1H-pyrazolo[4,3-c]pyridine-3,6(2H,5H)-dione | MS (ESI+): 480.1 | Ex. 17, Scheme 2 |
| 64 | 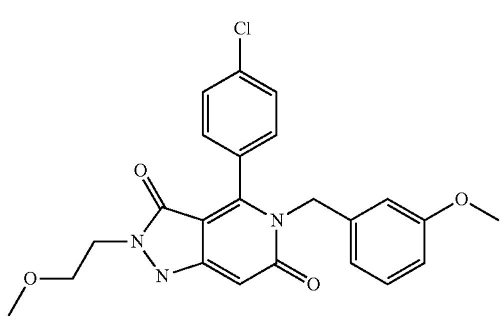 | 4-(4-chlorophenyl)-5-(3-methoxybenzyl)-2-(2-methoxyethyl)-1H-pyrazolo[4,3-c]pyridine-3,6(2H,5H)-dione | MS (ESI+): 441.1 | Ex. 17, Scheme 2 |

TABLE 1-continued

| Compound | Structure | Name | Data | Method |
|---|---|---|---|---|
| 65 | 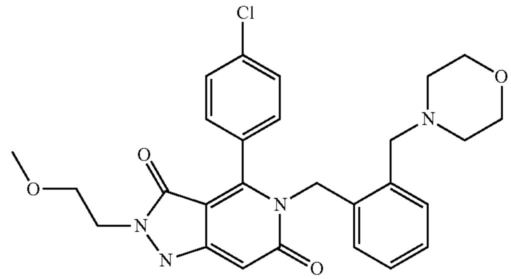 [SMILES: COCCn1[nH]c2cc(=O)n(Cc3ccccc3CN3CCOCC3)c(-c3ccc(Cl)cc3)c2c1=O] | 4-(4-chlorophenyl)-2-(2-methoxyethyl)-5-[2-(morpholin-4-ylmethyl)benzyl]-1H-pyrazolo[4,3-c]pyridine-3,6(2H,5H)-dione | MS (ESI+): 510.2 | Ex. 17, Scheme 2 |
| 66 | 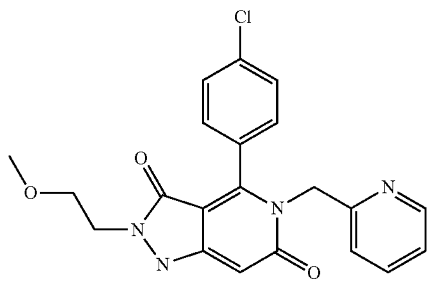 [SMILES: COCCn1[nH]c2cc(=O)n(Cc3ccccn3)c(-c3ccc(Cl)cc3)c2c1=O] | 4-(4-chlorophenyl)-2-(2-methoxyethyl)-5-(pyridin-2-ylmethyl)-1H-pyrazolo[4,3-c]pyridine-3,6(2H,5H)-dione | MS (ESI+): 411.9 | Ex. 17, Scheme 2 |
| 67 | 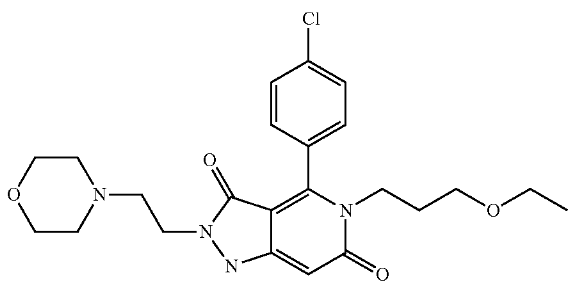 [SMILES: CCOCCCn1c(-c2ccc(Cl)cc2)c2c(=O)n(CCN3CCOCC3)[nH]c2cc1=O] | 4-(4-chlorophenyl)-5-(3-ethoxypropyl)-2-(2-morpholin-4-ylethyl)-1H-pyrazolo[4,3-c]pyridine-3,6(2H,5H)-dione | MS (ESI+): 462.0 | Ex. 17, Scheme 2 |
| 68 | 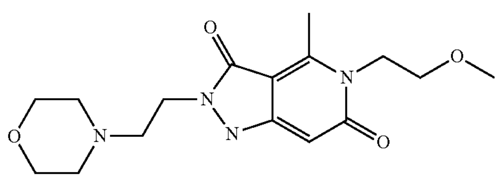 [SMILES: COCCn1c(C)c2c(=O)n(CCN3CCOCC3)[nH]c2cc1=O] | 5-(2-methoxyethyl)-4-methyl-2-(2-morpholin-4-ylethyl)-1H-pyrazolo[4,3-c]pyridine-3,6(2H,5H)-dione | MS (ESI+): 337.5 | Ex. 1, Scheme 1 |
| 69 | 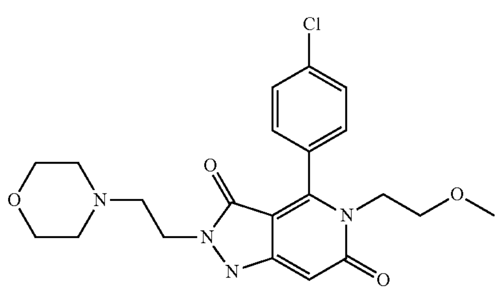 [SMILES: COCCn1c(-c2ccc(Cl)cc2)c2c(=O)n(CCN3CCOCC3)[nH]c2cc1=O] | 4-(4-chlorophenyl)-5-(2-methoxyethyl)-2-(2-morpholin-4-ylethyl)-1H-pyrazolo[4,3-c]pyridine-3,6(2H,5H)-dione | MS (ESI+): 433.9 | Ex. 17, Scheme 2 |
| 70 | 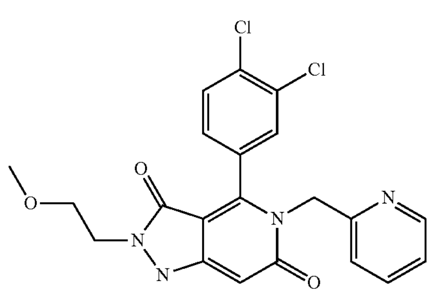 [SMILES: COCCn1[nH]c2cc(=O)n(Cc3ccccn3)c(-c3ccc(Cl)c(Cl)c3)c2c1=O] | 4-(3,4-dichlorophenyl)-2-(2-methoxyethyl)-5-(pyridin-2-ylmethyl)-1H-pyrazolo[4,3-c]pyridine-3,6(2H,5H)-dione | MS (ESI+): 446.4 | Ex. 17, Scheme 2 |

TABLE 1-continued

| Compound | Structure | Name | Data | Method |
|---|---|---|---|---|
| 71 | 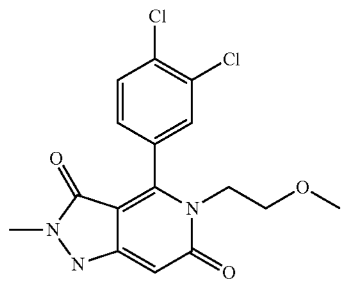 | 4-(3,4-dichlorophenyl)-5-(2-methoxyethyl)-2-methyl-1H-pyrazolo[4,3-c]pyridine-3,6-(2H,5H)-dione | MS (ESI+): 369.7 | Ex. 17, Scheme 2 |
| 72 | 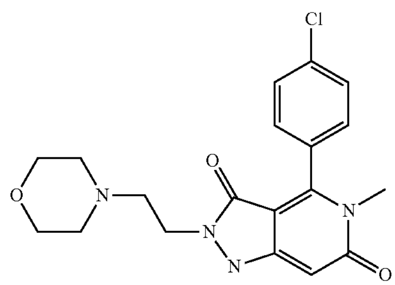 [SMILES: Cn1c(-c2ccc(Cl)cc2)c2c(=O)n(CCN3CCOCC3)[nH]c2cc1=O] | 4-(4-chlorophenyl)-5-methyl-2-(2-morpholin-4-ylethyl)-1H-pyrazolo[4,3-c]pyridine-3,6(2H,5H)-dione | MS (ESI+): 390.1 | Ex. 17, Scheme 2 |
| 73 | 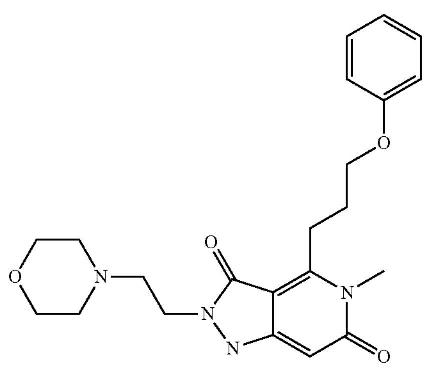 [SMILES: Cn1c(CCCOc2ccccc2)c2c(=O)n(CCN3CCOCC3)[nH]c2cc1=O] | 5-methyl-2-(2-morpholin-4-ylethyl)-4-(3-phenoxy propyl)-1H-pyrazolo[4,3-c]pyridine-3,6(2H,5H)-dione | MS (ESI+): 413.5 | Ex. 17, Scheme 2 |
| 74 | 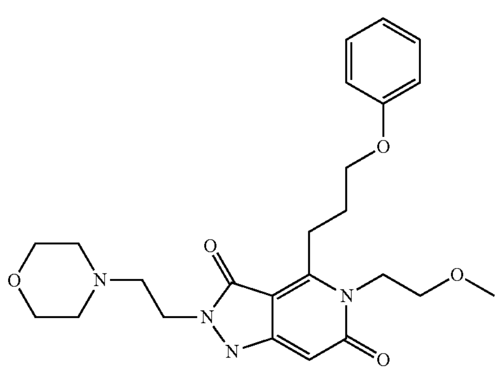 [SMILES: COCCn1c(CCCOc2ccccc2)c2c(=O)n(CCN3CCOCC3)[nH]c2cc1=O] | 5-(2-methoxyethyl)-2-(2-morpholin-4-ylethyl)-4-(3-phenoxypropyl)-1H-pyrazolo[4,3-c]pyridine-3,6(2H,5H)-dione | MS (ESI+): 457.6 | Ex. 17, Scheme 2 |

TABLE 1-continued

| Compound | Structure | Name | Data | Method |
|---|---|---|---|---|
| 75 | 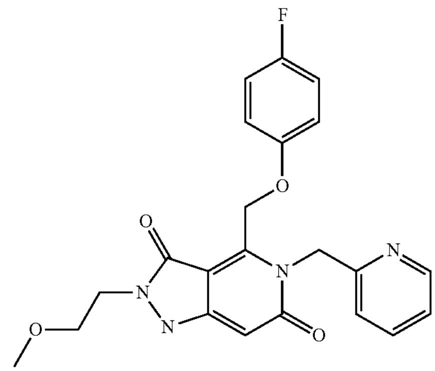 [SMILES: COCCn1[nH]c2cc(=O)n(Cc3ccccn3)c(COc3ccc(F)cc3)c2c1=O] | 4-[(4-fluorophenoxy)methyl]-2-(2-methoxyethyl)-5-(pyridin-2-ylmethyl)-1H-pyrazolo[4,3-c]pyridine-3,6(2H,5H)-dione | MS (ESI+): 425.5 | Ex. 17, Scheme 2 |
| 76 | 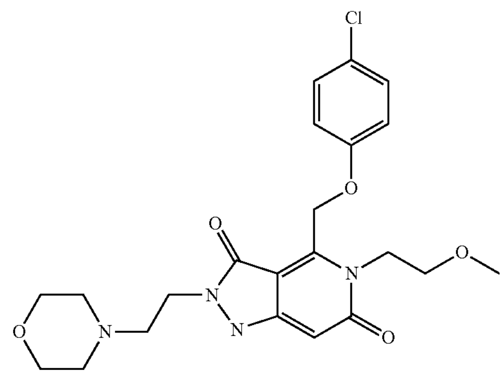 | 4-[(4-chlorophenoxy)methyl]-5-(2-methoxyethyl)-2-(2-morpholin-4-ylethyl)-1H-pyrazolo[4,3-c]pyridine-3,6(2H,5H)-dione | MS (ESI+): 464.1 | Ex. 17, Scheme 2 |
| 77 | 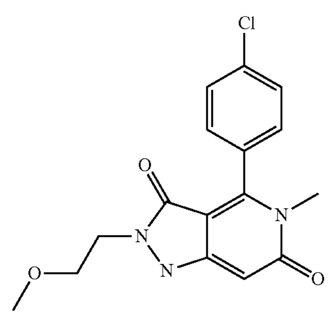 | 4-(4-chlorophenyl)-2-(2-methoxyethyl)-5-methyl-1H-pyrazolo[4,3-c]pyridine-3,6(2H,5H)-dione | MS (ESI+): 334.9 | Ex. 17, Scheme 2 |
| 78 | 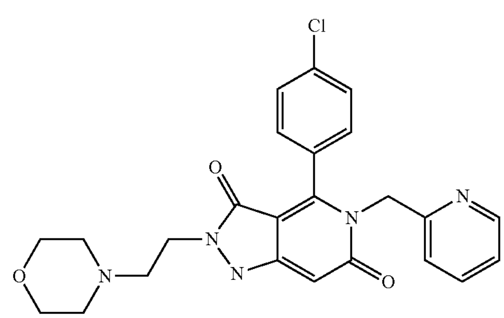 [SMILES: O=c1c2c(-c3ccc(Cl)cc3)n(Cc3ccccn3)c(=O)cc2[nH]n1CCN1CCOCC1] | 4-(4-chlorophenyl)-2-(2-morpholin-4-ylethyl)-5-(pyridine-2-ylmethyl)-1H-pyrazolo[4,3-c]pyridine-3,6-(2H,5H)-dione | MS (ESI+): 466.8 | Ex. 17, Scheme 2 |

TABLE 1-continued

| Compound | Structure | Name | Data | Method |
|---|---|---|---|---|
| 79 | 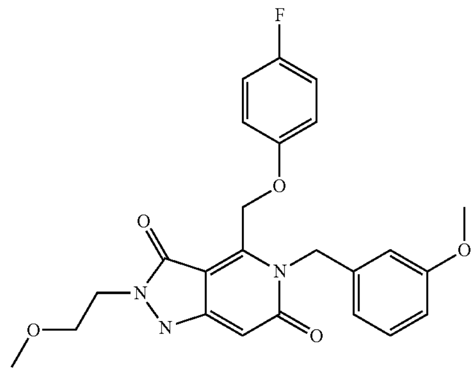 | 4-[(4-fluorophenoxy)methyl]-5-(3-methoxybenzyl)-2-(2-methoxyethyl)-1H-pyrazolo[4,3-c]pyridine-3,6(2H,5H)-dione | MS (ESI+): 454.6 | Ex. 17, Scheme 2 |
| 80 | 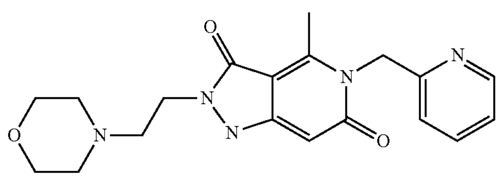 [SMILES: Cc1c2c(=O)n(CCN3CCOCC3)[nH]c2cc(=O)n1Cc1ccccn1] | 4-methyl-2-(2-morpholin-4-ylethyl)-5-(pyridin-2-yl methyl)-1H-pyrazolo[4,3-c]pyridine-3,6(2H,5H)-dione | MS (ESI+): 370.5 | Ex. 1, Scheme 1 |
| 81 | 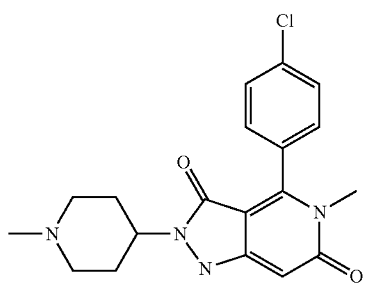 | 4-(4-chlorophenyl)-5-methyl-2-(1-methylpiperidin-4-yl)-1H-pyrazolo[4,3-c]pyridine-3,6(2H,5H)-dione | MS (ESI+): 373.9 | Ex. 17, Scheme 2 |
| 82 | 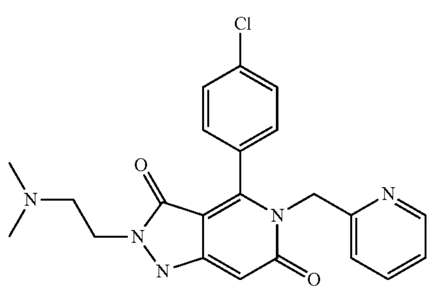 [SMILES: CN(C)CCn1[nH]c2cc(=O)n(Cc3ccccn3)c(-c3ccc(Cl)cc3)c2c1=O] | 4-(4-chlorophenyl)-2-[2-(dimethylamino)ethyl]-5-(pyridin-2-ylmethyl)-1H-pyrazolo[4,3-c]pyridine-3,6(2H,5H)-dione | MS (ESI+): 425.3 | Ex. 17, Scheme 2 |
| 83 | 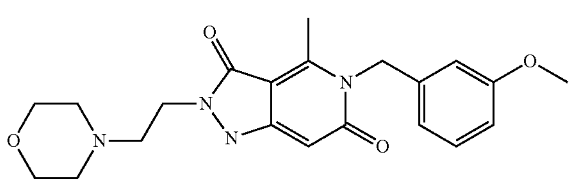 [SMILES: COc1cccc(Cn2c(C)c3c(=O)n(CCN4CCOCC4)[nH]c3cc2=O)c1] | 5-(3-methoxybenzyl)-4-methyl-2-(2-morpholin-4-ylethyl)-1H-pyrazolo[4,3-c]pyridine-3,6(2H,5H)-dione | MS (ESI+): 399.6 | Ex. 1, Scheme 1 |

TABLE 1-continued

| Compound | Structure | Name | Data | Method |
|---|---|---|---|---|
| 84 | 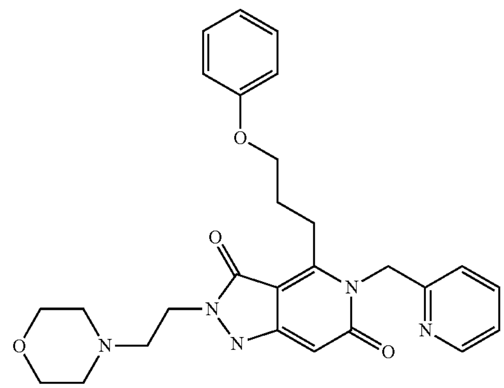 [SMILES: O=c1c2c(CCCOc3ccccc3)n(Cc3ccccn3)c(=O)cc2[nH]n1CCN1CCOCC1] | 2-(2-morpholin-4-ylethyl)-4-(3-phenoxypropyl)-5-(pyridine-2-ylmethyl)-1H-pyrazolo[4,3-c]pyridine-3,6(2H,5H)-dione | MS (ESI+): 490.7 | Ex. 17, Scheme 2 |
| 85 | 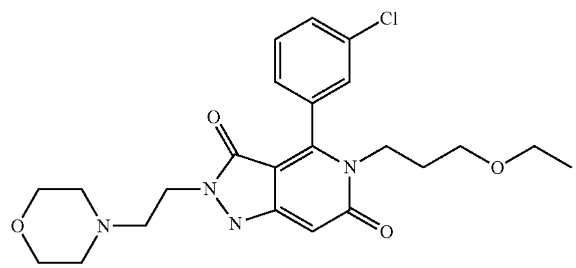 [SMILES: CCOCCCn1c(-c2cccc(Cl)c2)c2c(=O)n(CCN3CCOCC3)[nH]c2cc1=O] | 4-(3-chlorophenyl)-5-(3-ethoxypropyl)-2-(2-morpholin-4-ylethyl)-1H-pyrazolo[4,3-c]pyridine-3,6(2H,5H)-dione | MS (ESI+): 462.0 | Ex. 17, Scheme 2 |
| 86 | 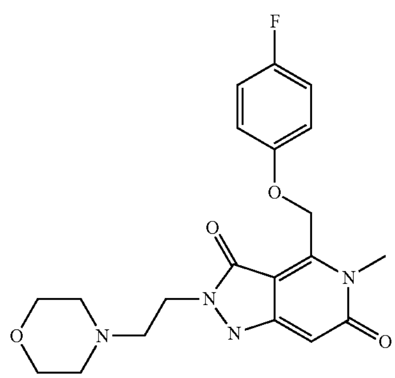 [SMILES: Cn1c(COc2ccc(F)cc2)c2c(=O)n(CCN3CCOCC3)[nH]c2cc1=O] | 4-[(4-fluorophenoxy)methyl]-5-methyl-2-(2-morpholin-4-ylethyl)-1H-pyrazolo[4,3-c]pyridine-3,6(2H,5H)-dione | MS (ESI+): 403.5 | Ex. 17, Scheme 2 |
| 87 | 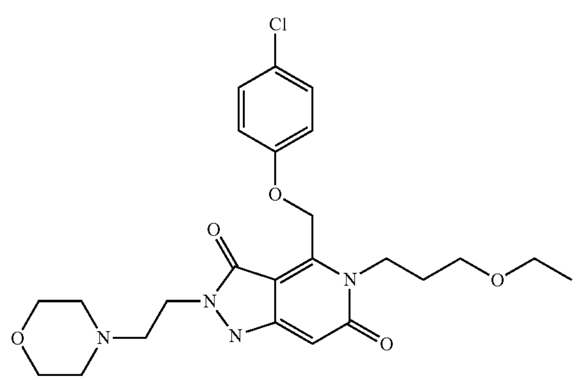 [SMILES: CCOCCCn1c(COc2ccc(Cl)cc2)c2c(=O)n(CCN3CCOCC3)[nH]c2cc1=O] | 4-[(4-chlorophenoxy)methyl]-5-(3-ethoxypropyl)-2-(2-morpholin-4-ylethyl)-1H-pyrazolo[4,3-c]pyridine-3,6(2H,5H)-dione | MS (ESI+): 492.0 | Ex. 17, Scheme 2 |

TABLE 1-continued

| Compound | Structure | Name | Data | Method |
|---|---|---|---|---|
| 88 | 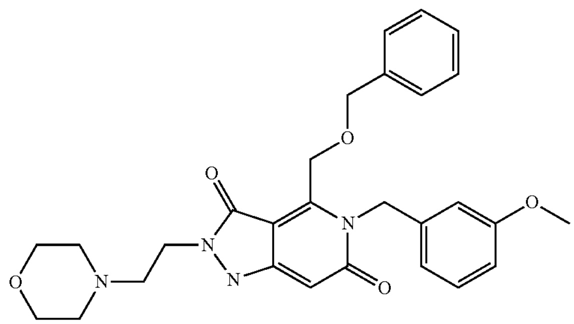 [SMILES: COc1cccc(Cn2c(COCc3ccccc3)c3c(=O)n(CCN4CCOCC4)[nH]c3cc2=O)c1] | 4-[(benzyloxy)methyl]-5-(3-methoxybenzyl)-2-(2-morpholin-4-ylethyl)-1H-pyrazolo[4,3-c]pyridine-3,6(2H,5H)-dione | MS (ESI+): 505.6 | Ex. 17, Scheme 2 |
| 89 | 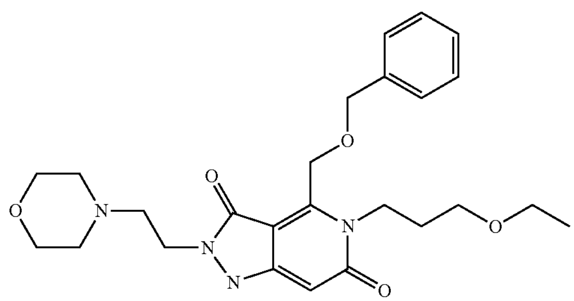 | 4-[(benzyloxy)methyl]-5-(3-ethoxypropyl)-2-(2-morpholin-4-ylethyl)-1H-pyrazolo[4,3-c]pyridine-3,6(2H,5H)-dione | MS (ESI+): 417.7 | Ex. 17, Scheme 2 |
| 90 | 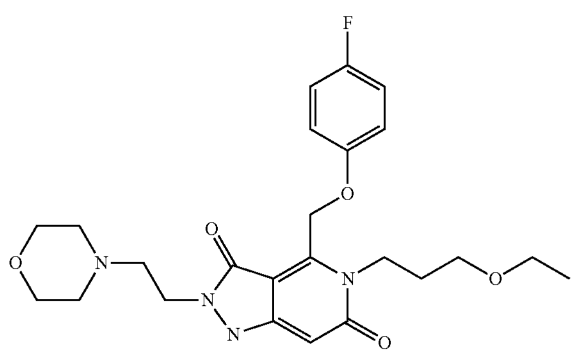 [SMILES: CCOCCCn1c(COc2ccc(F)cc2)c2c(=O)n(CCN3CCOCC3)[nH]c2cc1=O] | 5-(3-ethoxypropyl)-4-[(4-fluorophenoxy)methyl]-2-(2-morpholin-4-ylethyl)-1H-pyrazolo[4,3-c]pyridine-3,6(2H,5H)-dione | MS (ESI+): 475.6 | Ex. 17, Scheme 2 |
| 91 | 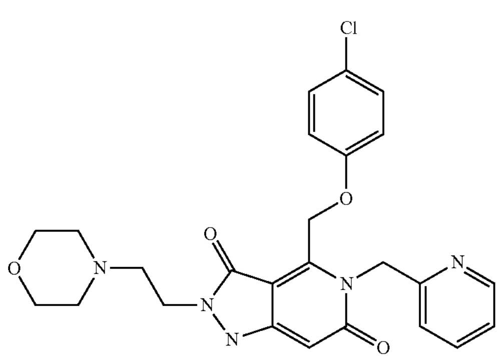 [SMILES: O=c1c2c(COc3ccc(Cl)cc3)n(Cc3ccccn3)c(=O)cc2[nH]n1CCN1CCOCC1] | 4-[(4-chlorophenoxy)methyl]-2-(2-morpholin-4-ylethyl)-5-(pyridin-2-ylmethyl)-1H-pyrazolo[4,3-c]pyridine-3,6(2H,5H)-dione | MS (ESI+): 497.0 | Ex. 17, Scheme 2 |

TABLE 1-continued

| Compound | Structure | Name | Data | Method |
|---|---|---|---|---|
| 92 | 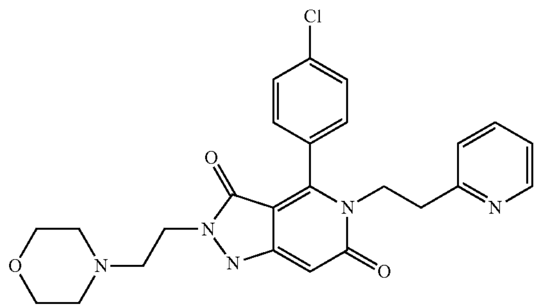 [SMILES: O=c1c2c(-c3ccc(Cl)cc3)n(CCc3ccccn3)c(=O)cc2[nH]n1CCN1CCOCC1] | 4-(4-chlorophenyl)-2-(2-morpholin-4-ylethyl)-5-(2-pyridin-2-ylethyl)-1H-pyrazolo[4,3-c]pyridine-3,6(2H,5H)-dione | MS (ESI+): 481.2 | Ex. 17, Scheme 2 |
| 93 | 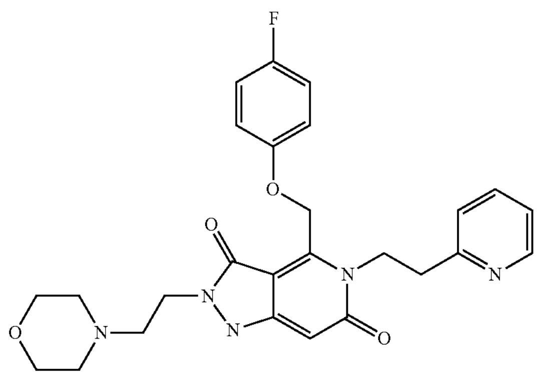 [SMILES: O=c1c2c(COc3ccc(F)cc3)n(CCc3ccccn3)c(=O)cc2[nH]n1CCN1CCOCC1] | 4-[(4-fluorophenoxy)methyl]-2-(2-morpholin-4-ylethyl)-5-(2-pyridin-2-ylethyl)-1H-pyrazolo[4,3-c]pyridine-3,6(2H,5H)-dione | MS (ESI+): 494.6 | Ex. 17, Scheme 2 |
| 94 | 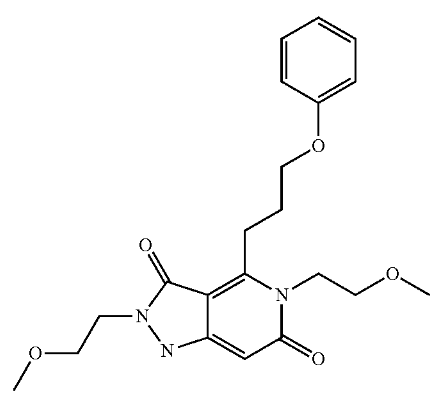 | 2,5-bis(2-methoxyethyl)-4-(3-phenoxypropyl)-1H-pyrazolo[4,3-c]pyridine-3,6(2H,5H)-dione | MS (ESI+): 402.5 | Ex. 17, Scheme 2 |
| 95 | 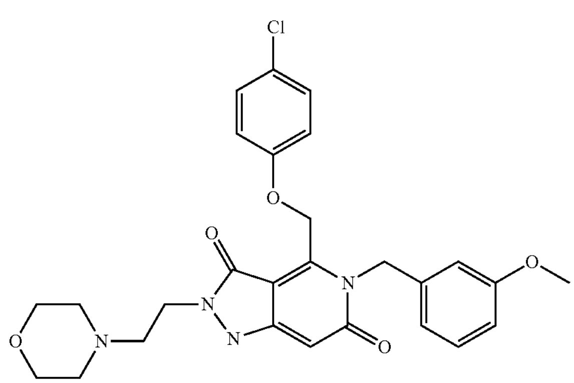 [SMILES: COc1cccc(Cn2c(COc3ccc(Cl)cc3)c3c(=O)n(CCN4CCOCC4)[nH]c3cc2=O)c1] | 4-[(4-chlorophenoxy)methyl]-5-(3-methoxybenzyl)-2-(2-morpholin-4-ylethyl)-1H-pyrazolo[4,3-c]pyridine-3,6(2H,5H)-dione | MS (ESI+): 526.4 | Ex. 17, Scheme 2 |

TABLE 1-continued

| Compound | Structure | Name | Data | Method |
|---|---|---|---|---|
| 96 | 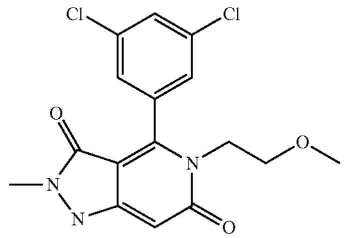 | 4-(3,5-dichlorophenyl)-5-(2-methoxyethyl)-2-methyl-1H-pyrazolo[4,3-c]pyridine-3,6(2H,5H)-dione | MS (ESI+): 369.8 | Ex. 17, Scheme 2 |
| 97 | 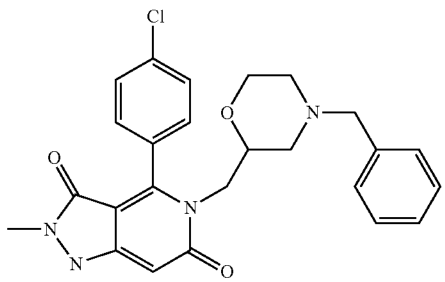 [SMILES: Cn1[nH]c2cc(=O)n(CC3CN(Cc4ccccc4)CCO3)c(-c3ccc(Cl)cc3)c2c1=O] | 5-[(4-benzylmorpholin-2-yl)methyl]-4-(4-chlorophenyl)-2-methyl-1H-pyrazolo[4,3-c]pyridine-3,6(2H,5H)-dione | MS (ESI+): 466.1 | Ex. 17, Scheme 2 |
| 98 | 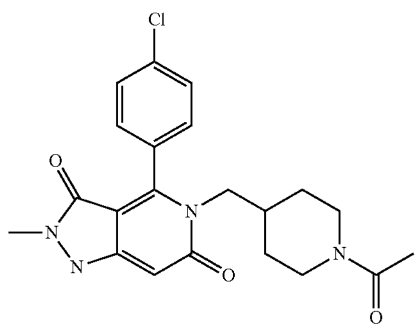 [SMILES: CC(=O)N1CCC(Cn2c(-c3ccc(Cl)cc3)c3c(=O)n(C)[nH]c3cc2=O)CC1] | 5-[1-acetylpiperidin-4-yl)methyl]-4-(4-chlorophenyl)-2-methyl-1H-pyrazolo[4,3-c]pyridine-3,6(2H,5H)-dione | MS (ESI+): 415.9 | Ex. 17, Scheme 2 |
| 99 | 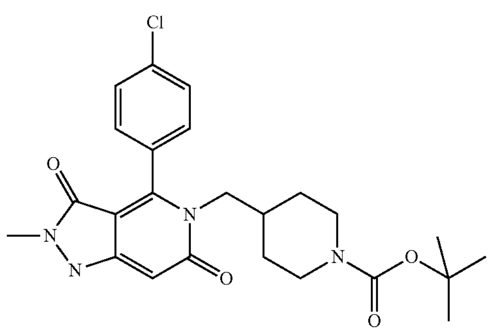 [SMILES: Cn1[nH]c2cc(=O)n(CC3CCN(C(=O)OC(C)(C)C)CC3)c(-c3ccc(Cl)cc3)c2c1=O] | tert-butyl 4-{[4-(4-chloro phenyl)-2-methyl-3,6-dioxo-1,2,3,6-tetrahydro-5H-pyrazolo[4,3-c]pyridin-5-yl]methyl}piperidine-1-carboxylate | MS (ESI+): 474.2 | Ex. 17, Scheme 2 |
| 100 | 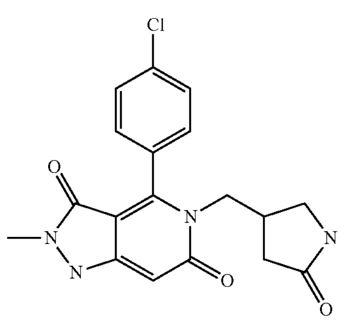 [SMILES: Cn1[nH]c2cc(=O)n(CC3CNC(=O)C3)c(-c3ccc(Cl)cc3)c2c1=O] | 4-(4-chlorophenyl)-2-methyl-5-[(5-oxopyrrolidin-3-yl)methyl]-1H-pyrazolo[4,3-c]pyridine-3,6(2H,5H)-dione | MS (ESI+): 373.7 | Ex. 17, Scheme 2 |

Example 18

Measurement of Levels of Reactive Oxygen Species in Different Cell Cultures

The activity of the compounds according to the invention may be tested for their activity in the inhibition or reduction of formation of reactive oxygen species (ROS) from oxygen in cells. The activity of the compounds is tested in the following cell cultures by different techniques such as nitroblue tetrazolium, Amplex Red, Chemiluminescence (Luminol) and 2',7'-dichlorodihydrofluorescein diacetate ($H_2$DCF-DA) according to the protocols detailed below.

Human Microglia Cell Line

Human microglia cell line (HMC3, human microglia clone 3) (Janabi et al., 1995, *Neurosci. Lett.* 195:105) were cultured in MEM (Eagle's minimum essential medium) containing 10% FBS with 50 U/ml penicillin G sodium 50 µg/ml streptomycin sulfate, and incubated at 37° C. for 24 hours. IFN-γ (human IFN-γ, Roche. 11 040 596 001) was added to the culture medium for a final concentration of 10 ng/ml 24 h, before detection of $O_2^-$ formation.

Human Umbilical Vein Endothelial Cells (HUVEC)

HUVEC are cultured in endothelial basal medium supplemented with hydrocortisone (1 µg/mL, CalbioChem), bovine brain extract (12 µg/mL), gentamicin (50 µg/mL, CalbioChem), amphotericin B (50 ng/mL, CalBioChem EGF (10 ng/mL, and 10% FCS until the fourth passage. When the fifth passage was started, cells were cultured with a lower concentration of FCS (2%) in the absence of EGF, if not indicated otherwise. All experiments were done with cells of the fifth passage. The cells were incubated with OxLDL (oxidized low-density lipoprotein) or its buffer as control for 24 h, before detection of $O_2^-$ formation.

HL-60 Cells

Human acute myeloid leukemia cell line HL-60 was cultured in RPMI 1640 (Invitrogen) supplemented with 10% heat-inactivated calf serum, 2 mM glutamine, 100 U/mL penicillin (Sigma), and 100 µg streptomycin (Sigma) at 37° C. under a humidified atmosphere of 5% $CO_2$. HL60 differentiation to the neutrophil phenotype was triggered by adding $Me_2$SO (final concentration 1.25% v/v for 6 days) to the culture medium.

1. Nitroblue Tetrazolium (NBT)

Intracellular and extracellular superoxide was measured by a colorimetric technique using a quantitative nitroblue tetrazolium (NBT) test. SOD-inhibitable conversion of NBT to formazan, a fine blue precipitate, in the presence of superoxide anion was measured using Fluostar Optima spectrometer (BMG labtech). Following incubation with appropriate stimuli, cells were trypsinized (1× Trypsin-EDTA), collected by centrifugation, and washed with PBS to remove medium. 5×10$^5$ cells were plated on 48-well plates and incubated in Hank's balanced salt solution containing 0.5 mg/mL NBT with or without 800 U/mL SOD in the presence or absence of compounds according to the invention. As a control, DPI was included at a final concentration of 10 µM. After 2.5 h, cells were fixed and washed with methanol to remove non reduced NBT. The reduced formazan was then dissolved in 230 µl of 2M potassium hydroxide and in 280 µl of dimethylsulfoxide. The absorption was measured at 630 nm. For calculation, the absorbance at 630 nm was normalized for each individual well. The mean of the four blank values was subtracted from each corrected value for each time point. NOX activities were expressed as % of the activity in control cells. Residual activity of DPI-treated cells was usually <10%.

2. Amplex Red

Extracellular hydrogen peroxide was measured using Amplex UltraRed (Molecular Probes). Cells were trypsinized (1× Trypsin-EDTA), collected by centrifugation, and resuspended in HBSS supplemented with 1% glucose. Cells were seeded into black 96-well plates at a density of 50,000 cells in 200 µl testing buffer (HBSS 1% glucose containing 0.005 U/mL horseradish peroxidase (Roche) and 50 µM Amplex Red in the presence or absence of compounds according to the invention. As a control, DPI was included at a final concentration of 10 µM The plates were placed in the fluorescent Optima Fluorescent plate reader and kept at 37° C. during 20 min. Fluorescence was measured for 15 min hours with excitation and emission wavelengths of 544 nm and 590 nm respectively. NOX activities were expressed as % of the activity in control cells. Residual activity of DPI-treated cells was usually <10%.

The Table 2 below summarizes the percentage of inhibition of NOX activity as measured by Amplex Red using DMSO-differentiated HL60 cells as described above:

TABLE 2

| Compound No. | Inhibition (%) |
| --- | --- |
| (1) | 67 |
| (2) | 61 |
| (3) | 63 |
| (4) | 65 |
| (5) | 48 |
| (6) | 74 |
| (8) | 79 |
| (10) | 77 |
| (13) | 56 |
| (15) | 72 |
| (16) | 74 |
| (18) | 75 |
| (19) | 73 |
| (20) | 75 |
| (21) | 74 |
| (24) | 79 |
| (28) | 78 |
| (30) | 77 |
| (35) | 72 |
| (44) | 78 |
| (48) | 91 |
| (51) | 76 |
| (58) | 95 |
| (74) | 95 |
| (77) | 90 |
| (83) | 89 |
| (86) | 87 |
| (89) | 86 |
| (94) | 90 |
| (97) | 89 |
| (98) | 92 |
| (100) | 90 |

The Table 3 below summarizes the $IC_{50}$ of NOX activity as measured by Amplex Red using DMSO-differentiated HL60 cells as described above:

TABLE 3

| Compound No. | $IC_{50}$ (µM) |
| --- | --- |
| (1) | <5 |
| (2) | <5 |
| (3) | <5 |
| (4) | <5 |
| (5) | <5 |
| (6) | <5 |
| (8) | <5 |
| (10) | <5 |
| (13) | <5 |

TABLE 3-continued

| Compound No. | IC$_{50}$ (μM) |
|---|---|
| (15) | <5 |
| (16) | <5 |
| (18) | <5 |
| (19) | <5 |
| (20) | <5 |
| (21) | <5 |
| (24) | <5 |
| (28) | <5 |
| (30) | <5 |
| (35) | <5 |
| (44) | <5 |
| (48) | <5 |
| (51) | <5 |
| (58) | <5 |
| (74) | <5 |
| (77) | <5 |
| (83) | <5 |
| (86) | <5 |
| (89) | <5 |
| (94) | <5 |

3. Chemiluminescence (Luminol)

ROS was measured using the chemiluminescent probe luminol. Cells were cultured and plated as for Amplex Red except that the Amplex Red agent was replaced by 10 μg/mL luminol (Sigma 09235). Light emission was recorded continuously at 37° C. for 60 minutes using the luminescence function of the FluoStar Optima fluorescent plate reader. The mean of the four blank values was subtracted from each corrected value for each time point. NOX activities were expressed as % of the activity in control cells. Residual activity of DPI-treated cells was usually <10%.

4. 2',7'-dichlorodihydrofluorescein diacetate (H$_2$DCF-DA)

HUVEC were plated on coverslips and made quiescent overnight in 0.5% BSA before stimulation with TGF-β. Cells were loaded for 10 minutes with 5 μM CM-H2DCFDA in phenol-red-free medium in the dark and then treated with TGF-β (R&D Systems) in the presence or absence of compounds according to the invention. Cells were then visualized by immunofluorescence microscopy after fixation and staining of the nuclei with DAPI or examined live using confocal microscopy. DCF fluorescence was visualized at an excitation wavelength of 488 nm and emission at 515 to 540 nm. To avoid photo-oxidation of the indicator dye, images were collected with a single rapid scan using identical parameters for all samples. For calculation, the absorbance at 540 nm was normalized to absorbance at 540 nm for each individual well. The mean of the four blank values was subtracted from each corrected value for each time point. NOX activities were expressed as % of the activity in control cells. Residual activity of DPI-treated cells was usually <10%.

Example 19

Blood Pressure Measurement in Spontaneous Hypertensive Rats (SHR)

In order to test the ability of compounds according to the invention to prevent or treat stroke, the following assay is carried out.

SHR at 11 weeks of age with systolic blood pressure above 170 mmHg are used. Compound according to the invention are administered orally to rats at a dose of about 3, 10, 30 and 100 mg/kg between 10:00 and 12:00 h. Mean, systolic and diastolic blood pressure and heart rate are monitored 2, 4, 6, 8 and 24 hours after the first administration of a compound according to the invention in order to perform a kinetic analysis over one day. After that, blood pressure is monitored every two days for two weeks, in the morning at 24 h time point and at the half life of the compound.

After the last injection, a 24 hour time point is monitored. The animals are controlled for an additional week without treatment in order to monitor the compound withdrawal. The animals are treated once a day for a period of two weeks by gavage with a special needle adapted for gavage at 5 ml/kg. Before using the animals, they are acclimated for two days and further trained during one week. The blood pressure is measured in awaken rats by tail-cuff plethysmography (Codas 6, Kent). Animals are included into groups after training for several days and if SBP variability was ≤40 mm Hg, i.e. +/−20 mm Hg. Baseline measurements were performed at least on two days before the experiment. Before the beginning of the experiment, animals are randomized in order to constitute homogeneous groups.

Example 20

Bleomycine-Induced Lung Injury in Mice

In order to test the ability of compounds according to the invention to prevent or treat respiratory disorder or disease, the following assay is carried out.

In order to produce pulmonary lesion which are comparable to those in respiratory disorder or disease such as idiopathic pulmonary fibrosis, animals receive endotracheally a single sublethal dose of bleomycine (BLM) (2.5 U/kg body weight dissolved in 0.25 ml of 0.9% NaCl). Control animals are subjected to the same protocol but received the same volume of intratracheal saline instead of BLM. Tracheal instillation is carried out under ketamin (80 mg/kg of body weight, i.p.) and xylazine (20 mg/kg de body weight, i.p.) anesthesia.

2 weeks days after endotracheal BLM or saline, the animals are killed by a lethal injection of sodium pentobarbital followed by exsanguination of abdominal aorta. Bronchoalveolar lavage is performed and lungs are weighed and processed separately for biochemical (homogenate right lung, n=10) and histological (left lung, n=10) studies as indicated below. The animals are randomly divided into four groups: control-saline (n=8) and control+BLM (n=10); Compound Dose 1+BLM (n=10) and Compound Dose 2+BLM (N=10). Treatments vehicle or compounds are administered for 2 weeks.

Mice are treated by daily oral administration of compound according to the invention or saline/control starting on day 0 for two weeks. Whole lung accumulation of acid-soluble collagen is analyzed by Sircol assay.

Example 21

Animal Models of Cancer

In order to test the ability of compounds according to the invention to treat cancers, in particular to reduce tumour growth and/or angiogenesis, the following assays are carried out.

In Vivo Angiogenesis Assay 7 to 10 weeks old C57BL6/J females are injected subcutaneously with 400 μl of Matrigel growth factor reduced complemented with 500 ng/ml of angiogenic factor (b-FGF or VEGF). One week after the graft, mice are scanned using MicroCT (Skyscan). Mice are injected retro-orbitally with a tracer (400 μl iodated liposomes) to visualize the vessel density. Scan picture are then reconstituted with Recon program and the density of grey in the plug is counted in all the slide of the plug. Compounds according to the invention are administered per oral route at the appropriate doses 1 and 2, once-a-day for 10 days. Results are expressed in grey density, which is correlated to vessel density. Matrigel plug are also frozen and stained for CD31 to visualize vessels.

Tumor Growth Assay $5.10^5$ Lewis Lung Carcinoma cells (LLC1) are injected subcutaneously in the back of mice. Mice are treated with a compound according to the invention at 40 mg/kg everyday per os. When the control tumor reaches about 1 cm length, mice are sacrificed and tumor are recovered, weighed and frozen. For therapeutic assay, mice are injected with LLC1 cells since tumours tumors have grown about 0.5 cm mice are treated and tumor size is assessed every day. After sacrifice, tumor are frozen and sections of tumor are stained with anti-CD31 antibody and ROS level is analyzed.

The invention claimed is:

1. A method for the inhibiting, arresting the development of, relieving the symptoms of and/or causing regression of the symptoms of a patient suffering from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, disorders of the gastrointestinal system, angiogenesis and angiogenesis-dependent conditions, the method comprising administering a pyrazolo pyridine derivative according to Formula (I):

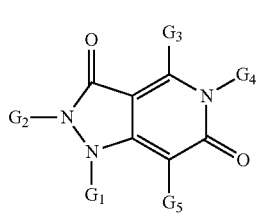

(I)

wherein $G_1$ is selected from H; optionally substituted acyl; optionally substituted acyl $C_1$-$C_6$ alkyl; optionally substituted alkyl $C_3$-$C_8$-cycloalkyl alkyl; optionally substituted heterocycloalkyl alkyl; optionally substituted aryl alkyl; and optionally substituted heteroaryl alkyl; $G_2$ is selected from —$CHR^1R^2$ and a saturated ring system selected from optionally substituted $C_3$-$C_8$-cycloalkyl and optionally substituted heterocycloalkyl; $R^1$ and $R^2$ are independently selected from H; optionally substituted alkoxy; optionally substituted alkoxy $C_1$-$C_6$ alkyl; optionally substituted amino; optionally substituted aminoalkyl; optionally substituted acyl; $C_1$-$C_6$ alkyl; optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; or —$CHR^1R^2$ form together a ring selected from optionally substituted $C_3$-$C_8$-cycloalkyl and optionally substituted heterocycloalkyl; $G_3$ is selected from H; optionally substituted amino; optionally substituted aminoalkyl; optionally substituted aminocarbonyl; optionally substituted alkoxy; optionally substituted alkoxy $C_1$-$C_6$ alkyl; optionally substituted carbonyl; optionally substituted $C_1$-$C_6$ alkyl; optionally substituted $C_2$-$C_6$ alkenyl; optionally substituted $C_2$-$C_6$ alkynyl; optionally substituted aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; $G_4$ is selected from H; optionally substituted acyl; optionally substituted acyl amino; optionally substituted acyl $C_1$-$C_6$ alkyl; optionally substituted $C_1$-$C_6$ alkyl; optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; $G_5$ is selected from H; optionally substituted $C_1$-$C_6$ alkyl; optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; or a tautomer, geometrical isomer, optically active form as enantiomer, diastereomer and racemate forms or a pharmaceutically acceptable salt thereof, to a patient in need of treatment of said disease or condition.

2. The method according to claim 1, wherein said disease or condition is selected from atherosclerosis, endothelial dysfunction, hypertension, cardiovascular complications of Type I or Type II diabetes, intimal hyperplasia, coronary heart disease, cerebral, coronary or arterial vasospasm, heart failure, congestive heart failure, peripheral artery disease, restenosis, trauma caused by a stent, stroke, ischemic attack, vascular complications after organ transplantation, myocardial infarction, hypertension, formation of atherosclerotic plaques, platelet aggregation, angina pectoris, aneurysm, aortic dissection, ischemic heart disease, cardiac hypertrophy, pulmonary embolus, thrombotic events, deep vein thrombosis, injury caused after ischemia by restoration of blood flow or oxygen delivery as in organ transplantation, open heart surgery, angioplasty, hemorrhagic shock, angioplasty of ischemic heart, brain, liver, kidney, retina and bowel, bronchial asthma, bronchitis, allergic rhinitis, adult respiratory syndrome, cystic fibrosis, lung viral infection (influenza), pulmonary hypertension, idiopathic pulmonary fibrosis, chronic obstructive pulmonary diseases (COPD), hay fever, asthma, obesity, metabolic syndrome, Type II diabetes, psoriasis, eczema, dermatitis, wound healing, scar formation, osteoporosis, osteoporasis, osteosclerosis, periodontitis, hyperparathyroidism, Alzheimer's disease, Parkinson's disease, Huntington's disease, amyotrophic lateral sclerosis, epilepsy, muscular dystrophy, leukoencephalopathies, leukodystrophies, multiple sclerosis, progressive multifocal leukoencephalopathy (PML), myelopathies, diabetic nephropathy, renal failure, glomerulonephritis, nephrotoxicity of aminoglycosides and platinum compounds, hyperactive bladder, chronic kidney diseases or disorders, erectile dysfunction, fertility disorders, prostatic hypertrophy, benign prostatic hypertrophy, cataract, diabetic cataract, re-opacification of the lens post cataract surgery, diabetic, retinopathy, presbyacusis, tinnitus, Meniere's disease, utriculolithiasis, vestibular migraine, noise induced hearing loss, drug induced hearing loss (ototoxicity), inflammatory bowel disease, sepsis, septic shock, adult respiratory distress syndrome, pancreatitis, shock induced by trauma, bronchial asthma, allergic rhinitis, rheumatoid arthritis, chronic rheumatoid arthritis, arteriosclerosis, intracerebral hemorrhage, cerebral infarction, heart failure, myocardial infarction, psoriasis, cystic fibrosis, stroke, acute bronchitis, chronic bronchitis, acute bronchiolitis, chronic bronchiolitis, osteoarthritis, gout, myelitis, ankylosing spondylitis, Reuter syndrome, psoriatic arthritis, spondylarthritis, juvenile arthritis or juvenile ankylosing spondylitis, reactive arthritis, infectious arthritis or arthritis after infection, gonococcal arthritis, syphilitic arthritis, Lyme disease, arthritis induced by "angiitis syndrome," polyarteritis nodosa, anaphylactic angiitis, Luegenec granulomatosis, rheumatoid polymyalgia, articular cell rheumatism, calcium crystal deposition arthritis, pseudogout, non-arthritic rheumatism, bursitis, tendosynovitis, epicondyle inflammation (tennis elbow), carpal tunnel syndrome, disorders by repetitive use (typing), mixed form of arthritis, neuropathic arthropathy, hemorrhagic arthritis, vascular peliosis, hypertrophic osteoarthropathy, multicentric reticulohistiocytosis, arthritis, blood pigmentation, sickle cell disease, hemoglobin abnormality, hyperlipoproteinemia, dysgammaglobulinemia, hyperparathyroidism, acromegaly, familial Mediterranean fever, Bechet's disease, systemic autoimmune disease erythematosus, multiple sclerosis and Crohn's disease, relapsing polychondritis, chronic inflammatory bowel diseases (IBD), liver fibrosis, alcohol induced fibrosis, steatosis, non-alcoholic steatohepatitis, rheumatic arthritis, chronic rheumatoid arthritis, chlamydial arthritis, chronic absorptive arthritis, chylous arthritis, arthritis based on bowel disease, filarial arthritis, gonorrheal arthritis, gouty arthritis, hemophilic arthritis, hypertrophic arthritis, juvenile chronic arthritis, Lyme arthritis, neonatal foal arthritis, nodular arthritis, ochronotic arthritis, psoriatic arthritis, suppurative arthritis, hyperalgesia, inflammatory pain, fibrosarcoma, myxosarcoma, liposarcoma, chondrosarcoma, osteogenic sarcoma, chordoma, angiosarcoma, endothelium sarcoma, lymphangiosarcoma, lymphangioendothelioma, periosteoma, mesothelioma, Ewing's tumor, leiomyosarcoma, rhabdomyosarcoma, colon carcinoma, pancreatic cancer, breast cancer, ovarian cancer, renal cancer, prostatic carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, cholangiocarcinoma, choriocarcinoma, seminoma, embryonal carcinoma, Wilms' tumor, cervical cancer, orchioncus, lung cancer, small-cell lung cancer, lung adenocarcinoma, bladder cancer, epithelial cancer, gastric mucosa disorders, ischemic bowel disease management, enteritis/colitis, cancer chemotherapy, neutropenia, sprouting angiogenesis, intussusceptive angiogenesis, vasculogenesis, arteriogenesis and lymphangiogenesis.

3. The method according to claim 1, wherein said disease or condition is selected from atherosclerosis, hypertension, cardiovascular complications of Type I or Type II diabetes, intimal hyperplasia, coronary heart disease, cerebral, coronary or arterial vasospasm, endothelial dysfunction, heart failure, congestive heart failure, peripheral artery disease, restenosis, trauma caused by a stent, stroke, ischemic attack, vascular complications after organ transplantation, myocardial infarction, hypertension, formation of atherosclerotic plaques, platelet aggregation, angina pectoris, aneurysm, aortic dissection, ischemic heart disease, cardiac hypertrophy, pulmonary embolus, thrombotic events, deep vein thrombosis, injury caused after ischemia by restoration of blood flow or oxygen delivery as in organ transplantation, open heart surgery, angioplasty, hemorrhagic shock, angioplasty of ischemic heart, brain, liver, kidney, retina and bowel.

4. The method according to claim 1, wherein said disease or condition is selected from bronchial asthma, bronchitis, allergic rhinitis, adult respiratory syndrome, cystic fibrosis, lung viral infection (influenza), pulmonary hypertension, idiopathic pulmonary fibrosis and chronic obstructive pulmonary diseases (COPD).

5. The method according to claim 1, wherein said disease or condition is obesity, metabolic syndrome or Type II diabetes.

6. The method according to claim 1, wherein said disease or condition is osteoporosis, osteoporasis, osteosclerosis, periodontitis, or hyperparathyroidism.

7. The method according to claim 1, wherein said disease or condition is diabetic nephropathy, renal failure, glomerulonephritis, nephrotoxicity of aminoglycosides and platinum compounds or hyperactive bladder.

8. The method according to claim 1, wherein said disease or condition is erectile dysfunction, fertility disorders, prostatic hypertrophy or benign prostatic hypertrophy.

9. The method according to claim 1, wherein said disease or condition is cataracts, re-opacification of the lens post cataract surgery, or diabetic retinopathy.

10. The method according to claim 1, wherein said disease or condition is inflammatory bowel disease, sepsis, septic shock, adult respiratory distress syndrome, pancreatitis, shock induced by trauma, bronchial asthma, allergic rhinitis, rheumatoid arthritis, chronic rheumatoid arthritis, arteriosclerosis, intracerebral hemorrhage, cerebral infarction, heart failure, myocardial infarction, psoriasis, cystic fibrosis, stroke, acute bronchitis, chronic bronchitis, acute bronchiolitis, chronic bronchiolitis, osteoarthritis, gout, myelitis, ankylosing spondylitis, Reuter syndrome, psoriatic arthritis, spondylarthritis, juvenile arthritis or juvenile ankylosing spondylitis, reactive arthritis, infectious arthritis or arthritis after infection, gonococcal arthritis, syphilitic arthritis, Lyme disease, arthritis induced by "angiitis syndrome," polyarteritis nodosa, anaphylactic angiitis, Luegenec granulomatosis, rheumatoid polymyalgia, articular cell rheumatism, calcium crystal deposition arthritis, pseudogout, non-arthritic rheumatism, bursitis, tendosynovitis, epicondyle inflammation (tennis elbow), carpal tunnel syndrome, disorders by repetitive use (typing), mixed form of arthritis, neuropathic arthropathy, hemorrhagic arthritis, vascular peliosis, hypertrophic osteoarthropathy, multicentric reticulohistiocytosis, arthritis, blood pigmentation, sickle cell disease, hemoglobin abnormality, hyperlipoproteinemia, dysgammaglobulinemia, hyperparathyroidism, acromegaly, familial Mediterranean fever, Bechet's disease, systemic autoimmune disease erythematosus, multiple sclerosis and Crohn's disease, relapsing polychondritis or chronic inflammatory bowel diseases (IBD).

11. The method according to claim 1, wherein said disease or condition is liver fibrosis, alcohol induced fibrosis, steatosis or non-alcoholic steatohepatitis.

12. The method according to claim 1, wherein said disease or condition is pulmonary fibrosis.

13. The method according to claim 1, wherein said disease or condition is inflammatory pain.

14. The method according to claim 1, wherein said disease or condition is fibrosarcoma, myxosarcoma, liposarcoma, chondrosarcoma, osteogenic sarcoma, chordoma, angiosarcoma, endothelium sarcoma, lymphangiosarcoma, lymphangioendothelioma, periosteoma, mesothelioma, Ewing's tumor, leiomyosarcoma, rhabdomyosarcoma, colon carcinoma, pancreatic cancer, breast cancer, ovarian cancer, renal cancer, prostatic carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, cholangiocarcinoma, choriocarcinoma, seminoma, embryonal carcinoma, Wilms' tumor, cervical cancer, orchioncus, lung cancer, small-cell lung cancer, lung adenocarcinoma, bladder cancer or epithelial cancer.

15. The method according to claim 14, wherein the pyrazolo pyridine derivative is administered in combination with a co-agent useful in the treatment of cancer.

16. A method for inhibiting angiogenesis in a patient suffering from angiogenesis or angiogenesis dependent disorder, wherein the method comprises administering an angiogenesis inhibitory dose of a compound of Formula (I)

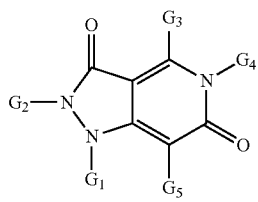

(I)

wherein $G_1$ is selected from H; optionally substituted acyl; optionally substituted acyl $C_1$-$C_6$ alkyl; optionally substituted alkyl; optionally substituted $C_3$-$C_8$-cycloalkyl alkyl; optionally substituted heterocycloalkyl alkyl; optionally substituted aryl alkyl; and heteroaryl alkyl; $G_2$ is selected from H; optionally substituted $C_1$-$C_6$ alkyl; optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; optionally substituted heteroaryl; optionally substituted alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; heterocycloalkyl; optionally substituted alkyl $C_3$-$C_8$-cycloalkyl; $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; $G_3$ is selected from —(CH$_2$)$_n$—R$^1$ and —(CH$_2$)$_p$—R$^5$; R$^1$ is selected from —NR$^2$R$^3$; —OR$^4$; optionally substituted heterocycloalkyl; optionally substituted heteroaryl; —CHR$^6$R$^7$; optionally substituted acyl and —C(O)NR$^2$R$^3$; R$^2$ and R$^3$ are independently selected from H; optionally substituted $C_1$-$C_6$ alkyl; optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; optionally substituted heteroaryl; optionally substituted alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl or NR$^2$R$^3$ form a ring selected from optionally substituted heteroaryl and optionally substituted heterocycloalkyl; R$^4$ is selected from H; optionally substituted alkoxy $C_1$-$C_6$ alkyl; optionally substituted $C_1$-$C_6$ alkyl; optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; optionally substituted heteroaryl; optionally substituted alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; R$^5$ is selected from H; optionally substituted alkoxy; optionally substituted alkoxy $C_1$-$C_6$ alkyl; optionally substituted $C_1$-$C_6$ alkyl; optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; optionally substituted heteroaryl; alkyl heteroaryl; optionally substituted heteroaryl $C_1$-$C_6$ alkyl; optionally substituted $C_2$-$C_6$ alkenyl aryl; aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; R$^6$ and R$^7$ are independently selected from optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; optionally substituted heteroaryl; optionally substituted alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl or —CHR$^6$R$^7$ forms an optionally substituted ring selected from optionally substituted heteroaryl, optionally substituted cycloalkyl and optionally substituted heterocycloalkyl; n is an integer selected from 0 to 5; p is an integer selected from 3 to 5; $G_4$ is selected from H; optionally substituted acyl; acyl amino; optionally substituted acyl $C_1$-$C_6$ alkyl; optionally substituted $C_1$-$C_6$ alkyl; optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; $G_5$ is selected from H; optionally substituted $C_1$-$C_6$ alkyl; optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; or a tautomer, geometrical isomer, optically active form as enantiomer, diastereomer and racemate forms or a pharmaceutically acceptable salt thereof, in a patient in need thereof.

17. The method according to claim 1, wherein $G_1$ is H.

18. The method according to claim 1, wherein $G_2$ is —CHR$^1$R$^2$; R$^1$ and R$^2$ are as defined in claim 1.

19. The method according to claim 1, wherein $G_2$ is a saturated ring system selected from optionally substituted $C_3$-$C_8$-cycloalkyl and optionally substituted heterocycloalkyl.

20. The method according to claim 1, wherein $G_5$ is H.

21. The method according to claim 1, the pyrazolo pyridine derivative is selected from the following compounds:

2-benzyl-4-methyl-5-(pyridin-2-ylmethyl)-1H-pyrazolo[4,3-c]pyridine-3,6(2H,5H)-dione;
2-(4-chlorobenzyl)-4-methyl-5-(pyridin-2-ylmethyl)-1H-pyrazolo[4,3-c]pyridine-3,6 (2H,5H)-dione;
2-benzyl-4-methyl-5-[3-(trifluoromethoxy)phenyl]-1H-pyrazolo[4,3-c]pyridine-3,6 (2H,5H)-dione;
2,4-dimethyl-5-(pyridin-2-ylmethyl)-1H-pyrazolo[4,3-c]pyridine-3,6(2H,5H)-dione;
2,4,5-trimethyl-1H-pyrazolo[4,3-c]pyridine-3,6(2H,5H)-dione;
5-(furan-2-ylmethyl)-2,4-dimethyl-1H-pyrazolo[4,3-c]pyridine-3,6(2H,5H)-dione;
5-(4-chlorobenzyl)-2,4-dimethyl-1H-pyrazolo[4,3-c]pyridine-3,6(2H,5H)-dione;
4-butyl-5-(4-chlorobenzyl)-2-methyl-1H-pyrazolo[4,3-c]pyridine-3,6(2H,5H)-dione;
4-butyl-2-methyl-5-(pyridin-2-ylmethyl)-1H-pyrazolo[4,3-c]pyridine-3,6(2H,5H)-dione;
5-(4-chlorobenzyl)-4-methyl-2-(2-morpholin-4-ylethyl)-1H-pyrazolo[4,3-c]pyridine-3,6 (2H,5H)-dione;
2-benzyl-4-butyl-5-(3,5-dimethoxybenzyl)-1H-pyrazolo[4,3-c]pyridine-3,6(2H,5H)-dione;
2-benzyl-4-butyl-5-(pyridin-2-ylmethyl)-1H-pyrazolo[4,3-c]pyridine-3,6(2H,5H)-dione;
2-cyclohexyl-4-methyl-5-[2-(morpholin-4-ylmethyl)benzyl]-1H-pyrazolo[4,3-c]pyridine-3,6(2H,5H)-dione;
2,4-dimethyl-5-(2-pyridin-2-ylethyl)-1H-pyrazolo[4,3-c]pyridine-3,6(2H,5H)-dione;
2-(2-methoxyethyl)-4-methyl-5-(2-pyridin-2-ylethyl)-1H-pyrazolo[4,3-c]pyridine-3,6 (2H,5H)-dione;
2,4-dimethyl-5-(2-morpholin-4-ylethyl)-1H-pyrazolo[4,3-c]pyridine-3,6(2H,5H)-dione;
5-(2-methoxyethyl)-4-methyl-2-(2-phenylethyl)-1H-pyrazolo[4,3-c]pyridine-3,6 (2H,5H)-dione;
2-(2-methoxyethyl)-4-methyl-5-[2-(morpholin-4-ylmethyl)benzyl]-1H-pyrazolo[4,3-c]pyridine-3,6(2H,5H)-dione;
N-{3-[2-(2-methoxyethyl)-4-methyl-3,6-dioxo-1,2,3,6-tetrahydro-5H-pyrazolo[4,3-c]pyridin-5-yl]phenyl}acetamide;
2-(2-methoxyethyl)-4-methyl-5-(2-morpholin-4-yl-2-oxoethyl)-1H-pyrazolo[4,3-c]pyridine-3,6(2H,5H)-dione;
2-benzyl-4-(3-methoxybenzyl)-5-(pyridin-2-ylmethyl)-1H-pyrazolo[4,3-c]pyridine-3,6 (2H,5H)-dione;
2-benzyl-4-(3-methoxybenzyl)-5-(2-methoxyethyl)-1H-pyrazolo[4,3-c]pyridine-3,6 (2H,5H)-dione;
2-(2,5-dichlorobenzyl)-5-(2-methoxyethyl)-4-methyl-1H-pyrazolo[4,3-c]pyridine-3,6 (2H,5H)-dione;
2-[2-(4-chlorophenoxy)ethyl]-4-methyl-5-(pyridin-2-ylmethyl)-1H-pyrazolo[4,3-c]pyridine-3,6(2H,5H)-dione;
2-(2,5-dichlorobenzyl)-4-methyl-5-(2-morpholin-4-ylethyl)-1H-pyrazolo[4,3-c]pyridine-3,6(2H,5H)-dione;
2-(2,5-dichlorobenzyl)-4-methyl-5-[2-(morpholin-4-ylmethyl)benzyl]-1H-pyrazolo[4,3-c]pyridine-3,6(2H,5H)-dione;
5-(3,5-dimethoxybenzyl)-2-(2-methoxyethyl)-4-methyl-1H-pyrazolo[4,3-c]pyridine-3,6 (2H,5H)-dione;
N-(3-{[4-methyl-3,6-dioxo-2-(2-phenylethyl)-1,2,3,6-tetrahydro-5H-pyrazolo[4,3-c]pyridin-5-yl]methyl}phenyl)acetamide;
4-methyl-5-(2-morpholin-4-ylethyl)-2-(2-phenylethyl)-1H-pyrazolo[4,3-c]pyridine-3,6(2H,5H)-dione;
4-methyl-5-[2-(morpholin-4-ylmethyl)benzyl]-2-(2-phenylethyl)-1H-pyrazolo[4,3-c]pyridine-3,6(2H,5H)-dione;
2-(2-methoxyethyl)-4-methyl-5-(pyridin-2-ylmethyl)-1H-pyrazolo[4,3-c]pyridine-3,6 (2H,5H)-dione;
N-[2-(2-benzyl-4-methyl-3,6-dioxo-1,2,3,6-tetrahydro-5H-pyrazolo[4,3-c]pyridin-5-yl)ethyl]-4-fluorobenzamide;
N-[3-(2-benzyl-4-methyl-3,6-dioxo-1,2,3,6-tetrahydro-5H-pyrazolo[4,3-c]pyridin-5-yl)phenyl]acetamide;
N-(3-{[2-(2-chloro-4-fluorobenzyl)-4-methyl-3,6-dioxo-1,2,3,6-tetrahydro-5H-pyrazolo[4,3-c]pyridin-5-yl]methyl}phenyl)acetamide;
5-[2-(4-benzylpiperazin-1-yl)-2-oxoethyl]-2-(2-methoxyethyl)-4-methyl-1H-pyrazolo[4,3-c]pyridine-3,6(2H,5H)-dione;
2-(2,5-dichlorobenzyl)-4-methyl-5-(pyridin-2-ylmethyl)-1H-pyrazolo[4,3-c]pyridine-3,6(2H,5H)-dione;
2-(2-chloro-4-fluorobenzyl)-4-methyl-5-[2-(morpholin-4-ylmethyl)benzyl]-1H-pyrazolo[4,3-c]pyridine-3,6 (2H,5H)-dione;

2-(2,5-dichlorobenzyl)-4-methyl-5-(2-morpholin-4-yl-2-oxoethyl)-1H-pyrazolo[4,3-c]pyridine-3,6(2H,5H)-dione;
4-methyl-2-(2-phenylethyl)-5-(pyridin-2-ylmethyl)-1H-pyrazolo[4,3-c]pyridine-3,6 (2H,5H)-dione;
2-(2-chloro-4-fluorobenzyl)-4-methyl-5-(pyridin-2-ylmethyl)-1H-pyrazolo[4,3-c]pyridine-3,6(2H,5H)-dione;
4-fluoro-N-{2-[2-(2-methoxyethyl)-4-methyl-3,6-dioxo-1,2,3,6-tetrahydro-5H-pyrazolo[4,3-c]pyridin-5-yl]ethyl}benzamide;
5-[2-(4-benzylpiperazin-1-yl)-2-oxoethyl]-2-(2-chloro-4-fluorobenzyl)-4-methyl-1H-pyrazolo[4,3-c]pyridine-3,6(2H,5H)-dione;
5-benzyl-4-methyl-2-(1-methylpiperidin-4-yl)-1H-pyrazolo[4,3-c]pyridine-3,6 (2H,5H)-dione;
4-methyl-2-(2-methylpropyl)-5-(pyridin-3-ylmethyl)-1H-pyrazolo[4,3-c]pyridine-3,6 (2H,5H)-dione;
4-methyl-2-(2-methylpropyl)-5-(2-morpholin-4-ylethyl)-1H-pyrazolo[4,3-c]pyridine-3,6(2H,5H)-dione;
5-(2,5-dichlorobenzyl)-4-methyl-2-(2-methylpropyl)-1H-pyrazolo[4,3-c]pyridine-3,6 (2H,5H)-dione;
5-(2,4-dichlorobenzyl)-4-methyl-2-(2-methylpropyl)-1H-pyrazolo[4,3-c]pyridine-3,6 (2H,5H)-dione;
5-(2,3-dihydro-1H-inden-1-yl)-4-methyl-2-(2-methylpropyl)-1H-pyrazolo[4,3-c]pyridine-3,6(2H,5H)-dione;
4-(3-chlorophenyl)-5-(2-morpholin-4-ylethyl)-2-(2-phenylethyl)-1H-pyrazolo[4,3-c]pyridine-3,6(2H,5H)-dione;
2-benzyl-4-(3-chlorophenyl)-5-(2-methoxyethyl)-1H-pyrazolo[4,3-c]pyridine-3,6 (2H,5H)-dione;
5-(4-chlorobenzyl)-4-[(4-fluorophenoxy)methyl]-2-(2-morpholin-4-ylethyl)-1H-pyrazolo[4,3-c]pyridine-3,6 (2H,5H)-dione;
4-[(4-fluorophenoxy)methyl]-5-(2-methoxyethyl)-2-(2-morpholin-4-ylethyl)-1H-pyrazolo[4,3-c]pyridine-3,6 (2H,5H)-dione;
5-(4-chlorobenzyl)-4-(3-chlorophenyl)-2-(2-morpholin-4-ylethyl)-1H-pyrazolo[4,3-c]pyridine-3,6(2H,5H)-dione;
4-(3-chlorophenyl)-2-(2-morpholin-4-ylethyl)-5-(pyridin-2-ylmethyl)-1H-pyrazolo[4,3-c]pyridine-3,6(2H,5H)-dione;
5-(4-chlorobenzyl)-4-(4-chlorophenyl)-2-(2-morpholin-4-ylethyl)-1H-pyrazolo[4,3-c]pyridine-3,6(2H,5H)-dione;
4-(4-chlorophenyl)-5-(4-methoxybenzyl)-2-(2-morpholin-4-ylethyl)-1H-pyrazolo[4,3-c]pyridine-3,6(2H,5H)-dione;
4-(4-chlorophenyl)-5-(3-methoxybenzyl)-2-(2-morpholin-4-ylethyl)-1H-pyrazolo[4,3-c]pyridine-3,6(2H,5H)-dione;
4-(4-chlorophenyl)-2,5-bis(2-methoxyethyl)-1H-pyrazolo[4,3-c]pyridine-3,6 (2H,5H)-dione;
5-(4-chlorobenzyl)-4-(4-chlorophenyl)-2-(2-methoxyethyl)-1H-pyrazolo[4,3-c]pyridine-3,6(2H,5H)-dione;
4-(4-chlorophenyl)-5-(2-methoxyethyl)-2-methyl-1H-pyrazolo[4,3-c]pyridine-3,6 (2H,5H)-dione;
4-[(4-fluorophenoxy)methyl]-5-(4-methoxybenzyl)-2-(2-morpholin-4-ylethyl)-1H-pyrazolo[4,3-c]pyridine-3,6 (2H,5H)-dione;
4-[(4-fluorophenoxy)methyl]-2-(2-morpholin-4-ylethyl)-5-(pyridin-2-ylmethyl)-1H-pyrazolo[4,3-c]pyridine-3,6(2H,5H)-dione;
4-(4-chlorophenyl)-5-(2-morpholin-4-ylethyl)-2-(2-phenylethyl)-1H-pyrazolo[4,3-c]pyridine-3,6(2H,5H)-dione;
4-(4-chlorophenyl)-5-(3-methoxybenzyl)-2-(2-methoxyethyl)-1H-pyrazolo[4,3-c]pyridine-3,6(2H,5H)-dione;
4-(4-chlorophenyl)-2-(2-methoxyethyl)-5-[2-(morpholin-4-ylmethyl)benzyl]-1H-pyrazolo[4,3-c]pyridine-3,6 (2H,5H)-dione;
4-(4-chlorophenyl)-2-(2-methoxyethyl)-5-(pyridin-2-ylmethyl)-1H-pyrazolo[4,3-c]pyridine-3,6(2H,5H)-dione;
4-(4-chlorophenyl)-5-(3-ethoxypropyl)-2-(2-morpholin-4-ylethyl)-1H-pyrazolo[4,3-c]pyridine-3,6(2H,5H)-dione;
5-(2-methoxyethyl)-4-methyl-2-(2-morpholin-4-ylethyl)-1H-pyrazolo[4,3-c]pyridine-3,6(2H,5H)-dione;
4-(4-chlorophenyl)-5-(2-methoxyethyl)-2-(2-morpholin-4-ylethyl)-1H-pyrazolo[4,3-c]pyridine-3,6(2H,5H)-dione;
4-(3,4-dichlorophenyl)-2-(2-methoxyethyl)-5-(pyridin-2-ylmethyl)-1H-pyrazolo[4,3-c]pyridine-3,6(2H,5H)-dione;
4-(3,4-dichlorophenyl)-5-(2-methoxyethyl)-2-methyl-1H-pyrazolo[4,3-c]pyridine-3,6 (2H,5H)-dione;
4-(4-chlorophenyl)-5-methyl-2-(2-morpholin-4-ylethyl)-1H-pyrazolo[4,3-c]pyridine-3,6(2H,5H)-dione;
5-methyl-2-(2-morpholin-4-ylethyl)-4-(3-phenoxypropyl)-1H-pyrazolo[4,3-c]pyridine-3,6(2H,5H)-dione;
5-(2-methoxyethyl)-2-(2-morpholin-4-ylethyl)-4-(3-phenoxypropyl)-1H-pyrazolo[4,3-c]pyridine-3,6(2H,5H)-dione;
4-[(4-fluorophenoxy)methyl]-2-(2-methoxyethyl)-5-(pyridin-2-ylmethyl)-1H-pyrazolo[4,3-c]pyridine-3,6(2H,5H)-dione;
4-[(4-chlorophenoxy)methyl]-5-(2-methoxyethyl)-2-(2-morpholin-4-ylethyl)-1H-pyrazolo[4,3-c]pyridine-3,6 (2H,5H)-dione;
4-(4-chlorophenyl)-2-(2-methoxyethyl)-5-methyl-1H-pyrazolo[4,3-c]pyridine-3,6 (2H,5H)-dione;
4-(4-chlorophenyl)-2-(2-morpholin-4-ylethyl)-5-(pyridin-2-ylmethyl)-1H-pyrazolo[4,3-c]pyridine-3,6(2H,5H)-dione;
4-[(4-fluorophenoxy)methyl]-5-(3-methoxybenzyl)-2-(2-methoxyethyl)-1H-pyrazolo[4,3-c]pyridine-3,6(2H,5H)-dione;
4-methyl-2-(2-morpholin-4-ylethyl)-5-(pyridin-2-ylmethyl)-1H-pyrazolo[4,3-c]pyridine-3,6(2H,5H)-dione;
4-(4-chlorophenyl)-5-methyl-2-(1-methylpiperidin-4-yl)-1H-pyrazolo[4,3-c]pyridine-3,6 (2H,5H)-dione;
4-(4-chlorophenyl)-2-[2-(dimethylamino)ethyl]-5-(pyridin-2-ylmethyl)-1H-pyrazolo[4,3-c]pyridine-3,6(2H,5H)-dione;
5-(3-methoxybenzyl)-4-methyl-2-(2-morpholin-4-ylethyl)-1H-pyrazolo[4,3-c]pyridine-3,6(2H,5H)-dione;
2-(2-morpholin-4-ylethyl)-4-(3-phenoxypropyl)-5-(pyridin-2-ylmethyl)-1H-pyrazolo[4,3-c]pyridine-3,6(2H,5H)-dione;
4-(3-chlorophenyl)-5-(3-ethoxypropyl)-2-(2-morpholin-4-ylethyl)-1H-pyrazolo[4,3-c]pyridine-3,6(2H,5H)-dione;
4-[(4-fluorophenoxy)methyl]-5-methyl-2-(2-morpholin-4-ylethyl)-1H-pyrazolo[4,3-c]pyridine-3,6(2H,5H)-dione;
4-[(4-chlorophenoxy)methyl]-5-(3-ethoxypropyl)-2-(2-morpholin-4-ylethyl)-1H-pyrazolo[4,3-c]pyridine-3,6 (2H,5H)-dione;
4-[(benzyloxy)methyl]-5-(3-methoxybenzyl)-2-(2-morpholin-4-ylethyl)-1H-pyrazolo[4,3-c]pyridine-3,6(2H,5H)-dione;

4-[(benzyloxy)methyl]-5-(3-ethoxypropyl)-2-(2-morpholin-4-ylethyl)-1H-pyrazolo[4,3-c]pyridine-3,6(2H,5H)-dione;

5-(3-ethoxypropyl)-4-[(4-fluorophenoxy)methyl]-2-(2-morpholin-4-ylethyl)-1H-pyrazolo[4,3-c]pyridine-3,6(2H,5H)-dione;

4-[(4-chlorophenoxy)methyl]-2-(2-morpholin-4-ylethyl)-5-(pyridin-2-ylmethyl)-1H-pyrazolo[4,3-c]pyridine-3,6(2H,5H)-dione;

4-(4-chlorophenyl)-2-(2-morpholin-4-ylethyl)-5-(2-pyridin-2-ylethyl)-1H-pyrazolo[4,3-c]pyridine-3,6(2H,5H)-dione;

4-[(4-fluorophenoxy)methyl]-2-(2-morpholin-4-ylethyl)-5-(2-pyridin-2-ylethyl)-1H-pyrazolo[4,3-c]pyridine-3,6(2H,5H)-dione;

2,5-bis(2-methoxyethyl)-4-(3-phenoxypropyl)-1H-pyrazolo[4,3-c]pyridine-3,6 (2H,5H)-dione;

4-[(4-chlorophenoxy)methyl]-5-(3-methoxybenzyl)-2-(2-morpholin-4-ylethyl)-1H-pyrazolo[4,3-c]pyridine-3,6(2H,5H)-dione;

4-(3,5-dichlorophenyl)-5-(2-methoxyethyl)-2-methyl-1H-pyrazolo[4,3-c]pyridine-3,6(2H,5H)-dione;

5-[(4-benzylmorpholin-2-yl)methyl]-4-(4-chlorophenyl)-2-methyl-1H-pyrazolo[4,3-c]pyridine-3,6(2H,5H)-dione;

5-[(1-acetylpiperidin-4-yl)methyl]-4-(4-chlorophenyl)-2-methyl-1H-pyrazolo[4,3-c]pyridine-3,6(2H,5H)-dione;

tert-butyl 4-{[4-(4-chloro phenyl)-2-methyl-3,6-dioxo-1,2,3,6-tetrahydro-5H-pyrazolo[4,3-c]pyridin-5-yl]methyl}piperidine-1-carboxylate; and 4-(4-chlorophenyl)-2-methyl-5-[(5-oxopyrrolidin-3-yl)methyl]-1H-pyrazolo[4,3-c]pyridine-3,6(2H,5H)-dione.

22. The method according to claim 1, wherein said method arrests the development of or relieves the symptoms of acute myeloid leukemia, lung cancer, prostate cancer, pulmonary hypertension, COPD, lung carcinoma or prostatic carcinoma.

23. The method according to claim 1, wherein said method arrests the development of or relieves the symptoms a cardiovascular disorder, respiratory disorder, metabolism disorder, skin disorder, bone disorder, neuroinflammatory and/or neurodegenerative disorder, kidney disease, reproduction disorder, disease affecting the eye and/or the lens and/or condition affecting the inner ear, inflammatory disorder, liver disease, pain, cancer, allergic disorder, traumatism, septic, hemorrhagic and anaphylactic shock, disorder of the gastrointestinal system, angiogenesis and angiogenesis-dependent conditions.

\* \* \* \* \*

UNITED STATES PATENT AND TRADEMARK OFFICE
CERTIFICATE OF CORRECTION

PATENT NO. : 9,006,238 B2
APPLICATION NO. : 13/755617
DATED : April 14, 2015
INVENTOR(S) : Patrick Page et al.

It is certified that error appears in the above-identified patent and that said Letters Patent is hereby corrected as shown below:

Specification

Column 47,
Compound 42, Column "Structure",

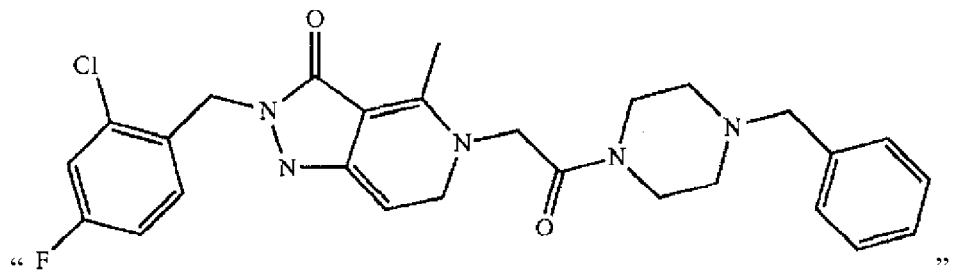

" should read

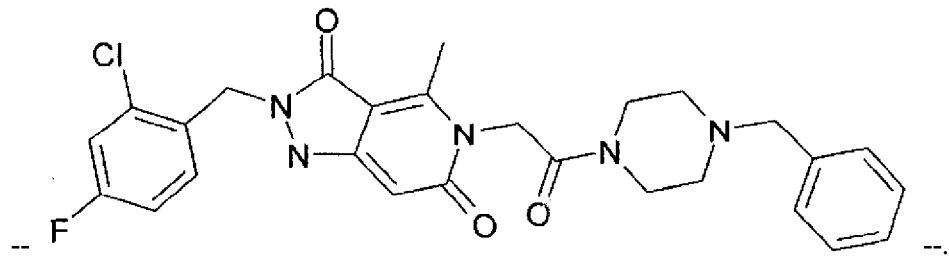

--.

Column 54,
Table 1, Compound 60, Column "Name",
"4-(4-chlorophenyl)-5-(2-methoxyethyl)-2-methyl-1H-pyrazolo[4,3-c]pyridine-3,6-(2H,5H)-dione" should read --4-(4-chlorophenyl)-5-(2-methoxyethyl)-2-methyl-1H-pyrazolo[4,3-c]pyridine-3,6(2H,5H)-dione--.

Signed and Sealed this
Eighth Day of March, 2016

Michelle K. Lee
*Director of the United States Patent and Trademark Office*

CERTIFICATE OF CORRECTION (continued)
U.S. Pat. No. 9,006,238 B2

Specification

Column 56,
Table 1, Compound 61, Column "Name",
"4-[(4-fluorophenoxy)methyl]-5-(4-methoxybenzyl)-2-(2-morpholin-4-ylethyl)-1H-pyrazolo[4,3-c]pyridine-3,6-(2H,5H)-dione" should read --4-[(4-fluorophenoxy)methyl]-5-(4-methoxybenzyl)-2-(2-morpholin-4-ylethyl)-1H-pyrazolo[4,3-c]pyridine-3,6(2H,5H)-dione--.

Column 60,
Table 1, Compound 71, Column "Name",
"4-(3,4-dichlorophenyl)-5-(2-methoxyethyl)-2-methyl-1H-pyrazolo[4,3-c]pyridine-3,6-(2H,5H)-dione" should read --4-(3,4-dichlorophenyl)-5-(2-methoxyethyl)-2-methyl-1H-pyrazolo[4,3-c]pyridine-3,6(2H,5H)-dione--.

Column 62,
Table 1, Compound 78, Column "Name",
"4-(4-chlorophenyl)-2-(2-morpholin-4-ylethyl)-5-(pyridine-2-ylmethyl)-1H-pyrazolo[4,3-c]pyridine-3,6-(2H,5H)-dione" should read -4-(4-chlorophenyl)-2-(2-morpholin-4-ylethyl)-5-(pyridine-2-ylmethyl)-1H-pyrazolo[4,3-c]pyridine-3,6(2H,5H)-dione--.

Column 68,
Table 1, Compound 89, Column "Data", "417.7" should read --471.7--.

Column 72,
Table 1, Compound 98, Column "Name",
"5-[1-acetylpiperidin-4-yl)methyl]-4-(4-chlorophenyl)-2-methyl-1H-pyrazolo[4,3-c]pyridine-3,6(2H,5H)-dione" should read --5-[(1-acetylpiperidin-4-yl)methyl]-4-(4-chlorophenyl)-2-methyl-1H-pyrazolo[4,3-c]pyridine-3,6(2H,5H)-dione--.